United States Patent
Koch

(10) Patent No.: US 9,775,321 B2
(45) Date of Patent: Oct. 3, 2017

(54) INBRED CORN LINE BC106

(71) Applicants: Limagrain Europe SA, Saint-Beauzire (FR); KWS SAAT AG, Einbeck (DE)

(72) Inventor: Thomas C. Koch, Westfield, IN (US)

(73) Assignees: Limagrain Europe S.A., Saint-Beauzire (FR); KWS SAAT AE, Einbeck (DE)

( * ) Notice: Subject to any disclaimer, the term of this patent is extended or adjusted under 35 U.S.C. 154(b) by 0 days.

(21) Appl. No.: 15/202,824

(22) Filed: Jul. 6, 2016

(65) Prior Publication Data

US 2016/0338304 A1  Nov. 24, 2016

Related U.S. Application Data

(63) Continuation of application No. 14/740,760, filed on Jun. 16, 2015, now Pat. No. 9,462,779, which is a continuation of application No. 13/856,840, filed on Apr. 4, 2013, now abandoned.

(60) Provisional application No. 61/620,398, filed on Apr. 4, 2012.

(51) Int. Cl.
*A01H 5/10* (2006.01)
*C12N 15/82* (2006.01)
*A01H 1/02* (2006.01)

(52) U.S. Cl.
CPC .............. *A01H 5/10* (2013.01); *A01H 1/02* (2013.01); *C12N 15/8241* (2013.01); *C12N 15/8242* (2013.01); *C12N 15/8245* (2013.01); *C12N 15/8247* (2013.01); *C12N 15/8271* (2013.01); *C12N 15/8273* (2013.01); *C12N 15/8274* (2013.01); *C12N 15/8275* (2013.01); *C12N 15/8277* (2013.01); *C12N 15/8278* (2013.01); *C12N 15/8279* (2013.01); *C12N 15/8281* (2013.01); *C12N 15/8283* (2013.01); *C12N 15/8286* (2013.01); *C12N 15/8289* (2013.01)

(58) Field of Classification Search
None
See application file for complete search history.

(56) References Cited

U.S. PATENT DOCUMENTS 7,109,404 B2 * 9/2006 Jenison ................... A01H 5/10
                                                          435/412

OTHER PUBLICATIONS

Shou et al 2004 (Journal of Experimental Botany 55:399 p. 1013-1019).*

* cited by examiner

*Primary Examiner* — Matthew Koegh
(74) *Attorney, Agent, or Firm* — Cooley LLP

(57) ABSTRACT

Inbred corn lines, designated BB202, AB8, AB18, AB19, BB84, BB85, BB95, BB98, BB201, BC106, BC137, CB20, or MN26, are disclosed. The invention relates to the seeds of inbred corn line BB202, AB8, AB18, AB19, BB84, BB85, BB95, BB98, BB201, BC106, BC137, CB20, or MN26, to the plants and plant parts of inbred corn line BB202, AB8, AB18, AB19, BB84, BB85, BB95, BB98, BB201, BC106, BC137, CB20, or MN26 and to methods for producing a corn plant, either inbred or hybrid, by crossing inbred corn line BB202, AB8, AB18, AB19, BB84, BB85, BB95, BB98, BB201, BC106, BC137, CB20, or MN26 with itself or another corn line. The invention also relates to products produced from the seeds, plants, or parts thereof, of inbred corn line BB202, AB8, AB18, AB19, BB84, BB85, BB95, BB98, BB201, BC106, BC137, CB20, or MN26 and/or of the hybrids produced using the inbred as a parent. The invention further relates to methods for producing a corn plant containing in its genetic material one or more transgenes and to the transgenic plants produced by that method and to methods for producing other inbred corn lines derived from inbred corn line BB202, AB8, AB18, AB19, BB84, BB85, BB95, BB98, BB201, BC106, BC137, CB20, or MN26.

30 Claims, No Drawings

INBRED CORN LINE BC106

CROSS-REFERENCE TO RELATED APPLICATIONS

This application is a continuation of U.S. patent application Ser. No. 14/740,760, filed Jun. 16, 2015, which is a continuation of U.S. patent application Ser. No. 13/856,840, filed Apr. 4, 2013, now abandoned, which claims the benefit of U.S. Provisional Patent Application Ser. No. 61/620,398, filed Apr. 4, 2012, each of which is hereby incorporated by reference in its entirety for all purposes.

FIELD OF THE INVENTION

The present invention relates to new and distinctive corn inbred lines (Zea mays, also known as maize), designated BB202, AB8, AB18, AB19, BB84, BB85, BB95, BB98, BB201, BC106, BC137, CB20, or MN26.

BACKGROUND OF THE INVENTION

The disclosures, including the claims, figures and/or drawings, of each and every patent, patent application, and publication cited herein are hereby incorporated herein by reference in their entireties.

The following description includes information that may be useful in understanding the present invention. It is not an admission that any of the information provided herein is prior art or relevant to the presently claimed inventions, or that any publication specifically or implicitly referenced is prior art.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, better stalks and roots, tolerance to drought and heat, reduction of grain moisture at harvest as well as better agronomic quality. With mechanical harvesting of many crops, uniformity of plant characteristics such as germination and stand establishment, growth rate, maturity and plant and ear height is important.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection, and backcross breeding.

The complexity of inheritance influences choice of breeding method. Backcross breeding is used to transfer one or a few favorable genes for a heritable trait into a desirable cultivar. This approach has been used extensively for breeding disease-resistant cultivars; nevertheless, it is also suitable for the adjustment and selection of morphological characters, color characteristics and simply inherited quantitative characters such as earliness, plant height or seed size and shape. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested per se and in hybrid combination and compared to appropriate standards in environments representative of the commercial target area(s) for three or more years. The best lines are candidates for use as parents in new commercial cultivars; those still deficient in a few traits may be used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a focus on clear objectives.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of corn breeding is to develop new, unique and superior corn inbred lines and hybrids. The breeder initially selects and crosses two or more parental lines, followed by repeated self pollination or selfing and selection, producing many new genetic combinations. Another method used to develop new, unique and superior corn inbred lines and hybrids occurs when the breeder selects and crosses two or more parental lines, followed by haploid induction and chromosome doubling that results in the development of dihaploid inbred lines. The breeder can theoretically generate billions of different genetic combinations via crossing, selfing and mutations and the same is true for the utilization of the dihaploid breeding method.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures or dihaploid breeding procedures), and with millions of different possible genetic combinations being generated. A breeder of ordinary skill in the art cannot predict the final resulting lines he develops, except possibly in a very gross and general fashion. This unpredictability results in the expenditure of large research funds to develop a superior new corn inbred line.

The development of commercial corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes or through the dihaploid breeding method followed by the selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars. Similarly, the development of new inbred lines through the dihaploid system requires the selection of the best inbreds followed by four to five years of testing in hybrid combinations in replicated plots.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., R. W. Allard, 1960, *Principles of Plant Breeding*, John Wiley and Son; Briggs, F. N. and Knowles, P. F. 1967. *Introduction to Plant Breeding*. Reinhold Publishing Corporation; N. W. Simmonds, 1979, Principles of Crop Improvement, Longman Group Limited; W. R. Fehr, 1987, Principles of Crop Development, Macmillan Publishing Co.; N. F. Jensen, 1988, Plant Breeding Methodology, John Wiley & Sons).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization.

The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny. A double-cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Hybrid corn seed is typically produced by a male sterility system or by incorporating manual or mechanical detasseling. Alternate strips of two corn inbreds are planted in a field, and the pollen-bearing tassels are removed from one of the inbreds (female). Providing that there is sufficient isolation from sources of foreign corn pollen, the ears of the detasseled inbred will be fertilized only from the other inbred (male), and the resulting seed is therefore hybrid and will form hybrid plants.

The laborious, and occasionally unreliable, detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in corn plants, since only the female provides cytoplasm to the fertilized seed. CMS plants are fertilized with pollen from another inbred that is not male-sterile. Pollen from the second inbred may or may not contribute genes that make the hybrid plants male-fertile. Seed from detasseled fertile corn and CMS produced seed of the same hybrid can be blended to insure that adequate pollen loads are available for fertilization when the hybrid plants are grown.

There are several methods of conferring genetic male sterility available, such as multiple mutant genes at separate locations within the genome that confer male sterility, as disclosed in U.S. Pat. Nos. 4,654,465 and 4,727,219 to Brar et al. These and all patents referred to are incorporated by reference. In addition to these methods, Albertsen et al., U.S. Pat. No. 5,432,068, have developed a system of nuclear male sterility which includes: identifying a gene which is critical to male fertility, silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.

There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see, Fabinjanski, et al. EPO 89/0301053.8 publication number 329,308 and PCT application PCT/CA90/00037 published as WO 90/08828).

Another version useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, G. R., U.S. Pat. No. 4,936,904). Application of the gametocide, timing of the application, and genotype often limit the usefulness of the approach.

Corn is an important and valuable field crop. Thus, a continuing goal of plant breeders is to develop stable, high yielding corn hybrids that are agronomically sound. The reasons for this goal are obviously to maximize the amount of ears or kernels produced on the land used and to supply food for both humans and animals. To accomplish this goal, the corn breeder must select and develop corn plants that have the traits that result in superior parental lines for producing hybrids.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above-described problems have been reduced or eliminated, while other embodiments are directed to other improvements.

According to the invention, there is provided inbred corn line designated BB202, AB8, AB18, AB19, BB84, BB85, BB95, BB98, BB201, BC106, BC137, CB20, or MN26. This invention thus relates to the seeds of inbred corn line BB202, AB8, AB18, AB19, BB84, BB85, BB95, BB98, BB201, BC106, BC137, CB20, or MN26, to the plants or parts thereof of inbred corn line BB202, AB8, AB18, AB19, BB84, BB85, BB95, BB98, BB201, BC106, BC137, CB20, or MN26, to plants or parts thereof having all the physiological and morphological characteristics of inbred corn line BB202, AB8, AB18, AB19, BB84, BB85, BB95, BB98, BB201, BC106, BC137, CB20, or MN26 and to plants or parts thereof having all the physiological and morphological characteristics of inbred corn line BB202, AB8, AB18, AB19, BB84, BB85, BB95, BB98, BB201, BC106, BC137, CB20, or MN26 listed in Table 1, including but not limited to as determined at the 5% significance level when grown in the same environmental conditions.

The invention also relates to variants, mutants and trivial modifications of the seed or plant of inbred corn line BB202, AB8, AB18, AB19, BB84, BB85, BB95, BB98, BB201, BC106, BC137, CB20, or MN26. Parts of the inbred corn plant of the present invention are also provided, such as e.g., pollen obtained from an inbred plant and an ovule of the inbred plant. Variants, mutants and trivial modifications of the seed or plant of the corn line of the present invention can be generated by methods available to one skilled in the art, including but not limited to, mutagenesis (e.g., chemical mutagenesis, radiation mutagenesis, transposon mutagenesis, insertional mutagenesis, signature tagged mutagenesis, site-directed mutagenesis, and natural mutagenesis), knockouts/knock-ins, antisense and RNA interference. For more information of mutagenesis in plants, such as agents, protocols, see Acquaah et al. (Principles of plant genetics and breeding, Wiley-Blackwell, 2007, ISBN 1405136464, 9781405136464, which is herein incorporated by reference in its entity).

The invention also relates to a mutagenized population of inbred corn line BB202, AB8, AB18, AB19, BB84, BB85, BB95, BB98, BB201, BC106, BC137, CB20, or MN26, and methods of using such populations. In some embodiments, the mutagenized population can be used in screening for new corn lines which comprises one or more or all of the morphological and physiological characteristics of inbred corn line BB202, AB8, AB18, AB19, BB84, BB85, BB95, BB98, BB201, BC106, BC137, CB20, or MN26. In some embodiments, the new corn lines obtained from the screening process comprise all of the morphological and physiological characteristics of inbred corn line BB202, AB8, AB18, AB19, BB84, BB85, BB95, BB98, BB201, BC106, BC137, CB20, or MN26, and one or more additional or different morphological and physiological characteristics that the inbred corn line BB202, AB8, AB18, AB19, BB84, BB85, BB95, BB98, BB201, BC106, BC137, CB20, or MN26 does not have.

The mutagenized population of the present invention can be used in Targeting Induced Local Lesions in Genomes (TILLING) screening method, which combines a standard and efficient technique of mutagenesis with a chemical mutagen (e.g., Ethyl methanesulfonate (EMS)) with a sensitive DNA screening-technique that identifies single base mutations (also called point mutations) in a target gene. Detailed description on methods and compositions on TILLING® can be found in Till et al. (Discovery of induced point mutations in maize genes by TILLING, BMC Plant Biology 2004, 4:12), Weil et al., (TILLING in Grass Species, Plant Physiology January 2009 vol. 149 no. 1 158-164), Comai, L. and S. Henikoff ("TILLING: practical single-nucleotide mutation discovery." Plant J 45(4): 684-94), McCallum et al., (Nature Biotechnology, 18: 455-457, 2000), McCallum et al., (Plant Physiology, 123: 439-442, 2000), Colbert et al., (Plant Physiol. 126(2): 480-484, 2001), U.S. Pat. No. 5,994,075, U.S. Patent Application Publication No. 2004/0053236A1, and International Patent Application Publication Nos. WO 2005/055704 and WO 2005/048692, each of which is hereby incorporated by reference for all purposes.

The plants and seeds of the present invention include those that may be of an essentially derived variety as defined in section 41(3) of the Plant Variety Protection Act, i.e., a variety that:

(i) is predominantly derived from inbred corn line BB202, AB8, AB18, AB19, BB84, BB85, BB95, BB98, BB201, BC106, BC137, CB20, or MN26, or from a variety that is predominantly derived from inbred corn line BB202, AB8, AB18, AB19, BB84, BB85, BB95, BB98, BB201, BC106, BC137, CB20, or MN26, while retaining the expression of the essential characteristics that result from the genotype or combination of genotypes of inbred corn line BB202, AB8, AB18, AB19, BB84, BB85, BB95, BB98, BB201, BC106, BC137, CB20, or MN26;

(ii) is clearly distinguishable from inbred corn line BB202, AB8, AB18, AB19, BB84, BB85, BB95, BB98, BB201, BC106, BC137, CB20, or MN26; and (iii) except for differences that result from the act of derivation, conforms to the initial variety in the expression of the essential characteristics that result from the genotype or combination of genotypes of the initial variety.

In another aspect, the present invention provides regenerable cells for use in tissue culture of inbred corn plant corn line BB202, AB8, AB18, AB19, BB84, BB85, BB95, BB98, BB201, BC106, BC137, CB20, or MN26. The tissue culture will preferably be capable of regenerating plants having all the physiological and morphological characteristics of the foregoing inbred corn plant. Preferably, the cells of such tissue cultures will be embryos, ovules, meristematic cells, seeds, callus, pollen, leaves, anthers, roots, root tips, silk, flowers, kernels, ears, cobs, husks, stalks or the like. Protoplasts produced from such tissue culture are also included in the present invention. The corn shoots, roots and whole plants regenerated from the tissue cultures are also part of the invention.

Also included in this invention are methods for producing a corn plant produced by crossing the inbred corn line BB202, AB8, AB18, AB19, BB84, BB85, BB95, BB98, BB201, BC106, BC137, CB20, or MN26 with itself or another corn line. When crossed with itself, i.e., crossed with another inbred corn line BB202, AB8, AB18, AB19, BB84, BB85, BB95, BB98, BB201, BC106, BC137, CB20, or MN26 plant or self-pollinated, the inbred line corn line BB202, AB8, AB18, AB19, BB84, BB85, BB95, BB98, BB201, BC106, BC137, CB20, or MN26 will be conserved (e.g., as an inbred). When crossed with another, different corn line, an $F_1$ hybrid seed is produced. $F_1$ hybrid seeds and plants produced by growing said hybrid seeds are included in the present invention. A method for producing an $F_1$ hybrid corn seed comprising crossing inbred corn line BB202, AB8, AB18, AB19, BB84, BB85, BB95, BB98, BB201, BC106, BC137, CB20, or MN26 corn plant with a different corn plant and harvesting the resultant hybrid corn seed are also part of the invention. The hybrid corn seed produced by the method comprising crossing inbred corn line BB202, AB8, AB18, AB19, BB84, BB85, BB95, BB98, BB201, BC106, BC137, CB20, or MN26 corn plant with a different corn plant and harvesting the resultant hybrid corn seed are included in the invention, as are included the hybrid corn plant or parts thereof, seeds included, produced by growing said hybrid corn seed.

In another embodiment, this invention relates to a method for producing the inbred corn line BB202, AB8, AB18, AB19, BB84, BB85, BB95, BB98, BB201, BC106, BC137, CB20, or MN26 from a collection of seeds, the collection containing both inbred corn line BB202, AB8, AB18, AB19, BB84, BB85, BB95, BB98, BB201, BC106, BC137, CB20, or MN26 seeds and hybrid seeds having inbred corn line BB202, AB8, AB18, AB19, BB84, BB85, BB95, BB98, BB201, BC106, BC137, CB20, or MN26 as a parental line. Such a collection of seeds might be a commercial bag of seeds. Said method comprises planting the collection of seeds. When planted, the collection of seeds will produce inbred corn line BB202, AB8, AB18, AB19, BB84, BB85, BB95, BB98, BB201, BC106, BC137, CB20, or MN26 plants from inbred corn line BB202, AB8, AB18, AB19, BB84, BB85, BB95, BB98, BB201, BC106, BC137, CB20, or MN26 seeds and hybrid plants from hybrid seeds. The plants having all the physiological and morphological characteristics of corn inbred line BB202, AB8, AB18, AB19, BB84, BB85, BB95, BB98, BB201, BC106, BC137, CB20, or MN26 or having a decreased vigor compared to the other plants grown from the collection of seeds are identified as inbred corn line BB202, AB8, AB18, AB19, BB84, BB85, BB95, BB98, BB201, BC106, BC137, CB20, or MN26 parent plant. Said decreased vigor is due to the inbreeding depression effect and can be identified for example by a less vigorous appearance for vegetative and/or reproductive characteristics including shorter plant height, small ear size, ear and kernel shape, ear color or other characteristics. As previously mentioned, if the inbred corn line BB202, AB8, AB18, AB19, BB84, BB85, BB95, BB98, BB201, BC106, BC137, CB20, or MN26 is self-pollinated, the inbred corn line BB202, AB8, AB18, AB19, BB84, BB85, BB95, BB98, BB201, BC106, BC137, CB20, or MN26 will be preserved, therefore, the next step is controlling pollination of the inbred parent plants in a manner which preserves the homozygosity of said inbred corn line BB202, AB8, AB18, AB19, BB84, BB85, BB95, BB98, BB201, BC106, BC137, CB20, or MN26 parent plant and the final step is to harvest the resultant seed.

This invention also relates to methods for producing other inbred corn lines derived from inbred corn line BB202, AB8, AB18, AB19, BB84, BB85, BB95, BB98, BB201, BC106, BC137, CB20, or MN26 and to the inbred corn lines derived by the use of those methods.

In another aspect, the present invention provides transformed inbred corn line BB202, AB8, AB18, AB19, BB84, BB85, BB95, BB98, BB201, BC106, BC137, CB20, or MN26 or parts thereof that have been transformed so that its genetic material contains one or more transgenes, preferably operably linked to one or more regulatory elements. Also, the invention provides methods for producing a corn plant containing in its genetic material one or more transgenes, preferably operably linked to one or more regulatory elements, by crossing transformed inbred corn line BB202, AB8, AB18, AB19, BB84, BB85, BB95, BB98, BB201, BC106, BC137, CB20, or MN26 with either a second plant of another corn line, or a non-transformed corn plant of the inbred corn line BB202, AB8, AB18, AB19, BB84, BB85, BB95, BB98, BB201, BC106, BC137, CB20, or MN26, so that the genetic material of the progeny that results from the cross contains the transgene(s), preferably operably linked to one or more regulatory elements. The invention also provides methods for producing a corn plant that contains in its genetic material one or more transgene(s), wherein the method comprises crossing the inbred corn line BB202, AB8, AB18, AB19, BB84, BB85, BB95, BB98, BB201, BC106, BC137, CB20, or MN26 with a second plant of another corn line which contains one or more transgene(s) operably linked to one or more regulatory element(s) so that the genetic material of the progeny that results from the cross contains the transgene(s) operably linked to one or more regulatory element(s). Transgenic corn plants, or parts thereof produced by the method are in the scope of the present invention.

More specifically, the invention comprises methods for producing corn plants or seeds with at least one trait selected from the group consisting of male sterile, male fertile, herbicide resistant, insect resistant, disease resistant, water stress tolerant corn plants or seeds, or corn plants or seeds with modified, in particular decreased, phytate content, with modified waxy and/or amylose starch content, with modified protein content, with modified oil content or profile, with increased digestibility or with increased nutritional quality. Said methods comprise transforming the inbred corn line BB202, AB8, AB18, AB19, BB84, BB85, BB95, BB98, BB201, BC106, BC137, CB20, or MN26 corn plant with nucleic acid molecules that confer, for example, male sterility, male fertility, herbicide resistance, insect resistance, disease resistance, water stress tolerance, or that can modify the phytate, the waxy and/or amylose starches, the protein or the oil contents, the digestibility or the nutritional qualities, respectively. The transformed corn plants or seeds obtained from the provided methods, including, for example, those corn plants or seeds with male sterility, male fertility, herbicide resistance, insect resistance, disease resistance, water stress tolerance, modified phytate, waxy and/or amylose starches, protein or oil contents, increased digestibility and increased nutritional quality are included in the present invention. Plants may display one or more of the above listed traits. For the present invention and the skilled artisan, disease is understood to be fungal disease, viral disease, bacterial disease or other plant pathogenic diseases and disease resistant plant encompasses plants resistant to fungal, viral, bacterial and other plant pathogens.

Also included in the invention are methods for producing a corn plant or seed containing in its genetic material one or more transgenes involved with fatty acid metabolism, carbohydrate metabolism, and starch content such as waxy starch or increased amylose starch. The transgenic corn plants or seeds produced by these methods are also part of the invention.

In another aspect, the present invention provides for methods of introducing one or more desired trait(s) into the inbred corn line BB202, AB8, AB18, AB19, BB84, BB85, BB95, BB98, BB201, BC106, BC137, CB20, or MN26 and plants or seeds obtained from such methods. The desired trait(s) may be, but not exclusively, a single gene, preferably a dominant but also a recessive allele. Preferably, the transferred gene or genes will confer such traits as male sterility, herbicide resistance, insect resistance, resistance for bacterial, fungal, or viral disease, male fertility, water stress tolerance, enhanced nutritional quality, modified waxy content, modified amylose content, modified protein content, modified oil content, enhanced plant quality, enhanced digestibility and industrial usage. The gene or genes may be naturally occurring maize gene(s) or transgene(s) introduced through genetic engineering techniques. The method for introducing the desired trait(s) is preferably a backcrossing process making use of a series of backcrosses to the inbred corn line BB202, AB8, AB18, AB19, BB84, BB85, BB95, BB98, BB201, BC106, BC137, CB20, or MN26 during which the desired trait(s) is maintained by selection.

When using a transgene, the trait is generally not incorporated into each newly developed line such as inbred corn line BB202, AB8, AB18, AB19, BB84, BB85, BB95, BB98, BB201, BC106, BC137, CB20, or MN26 by direct transformation. Rather, the more typical method used by breeders of ordinary skill in the art to incorporate the transgene is to take a line already carrying the transgene and to use such line as a donor line to transfer the transgene into the newly developed line. The same would apply for a naturally occurring trait (e.g., a native trait, such as but not limited to drought tolerance or improved nitrogen utilization) or one arising from spontaneous or induced mutations. The backcross breeding process comprises the following steps: (a) crossing inbred corn line BB202, AB8, AB18, AB19, BB84, BB85, BB95, BB98, BB201, BC106, BC137, CB20, or MN26 plants with plants of another line that comprise the desired trait(s), (b) selecting the $F_1$ progeny plants that have the desired trait(s); (c) crossing the selected $F_1$ progeny plants with the inbred corn line BB202, AB8, AB18, AB19, BB84, BB85, BB95, BB98, BB201, BC106, BC137, CB20, or MN26 plants to produce backcross progeny plants; (d) selecting for backcross progeny plants that have the desired trait(s) and physiological and morphological characteristics of corn inbred corn line BB202, AB8, AB18, AB19, BB84, BB85, BB95, BB98, BB201, BC106, BC137, CB20, or MN26 to produce selected backcross progeny plants; and (e) repeating steps (c) and (d) one, two, three, four, five, six, seven, eight, nine or more times in succession to produce selected, second, third, fourth, fifth, sixth, seventh, eighth, ninth or higher backcross progeny plants that comprise the desired trait(s) and all the physiological and morphological characteristics of corn inbred line corn line BB202, AB8, AB18, AB19, BB84, BB85, BB95, BB98, BB201, BC106, BC137, CB20, or MN26 as listed in Table 1A to 1S, including but not limited to at a 5% significance level when grown in the same environmental conditions. The corn plants or seeds produced by the methods are also part of the invention. Backcrossing breeding methods, well known to one skilled in the art of plant breeding will be further developed in subsequent parts of the specification.

In another aspect of the invention, inbred corn line BB202, AB8, AB18, AB19, BB84, BB85, BB95, BB98, BB201, BC106, BC137, CB20, or MN26 may be used as a parent, or a single gene conversion or a transgenic inbred corn line of BB202, AB8, AB18, AB19, BB84, BB85, BB95, BB98, BB201, BC106, BC137, CB20, or MN26, such as BB202, AB8, AB18, AB19, BB84, BB85, BB95, BB98, BB201, BC106, BC137, CB20, or MN26 MON89034 may be used as a parent and may be crossed with another corn line. Preferably, the single gene conversions or transgenic inbred lines will confer such traits, herbicide resistance, insect resistance, resistance for bacterial, fungal, or viral disease, male fertility, water stress tolerance, enhanced nutritional quality, modified waxy content, modified amylose content, modified protein content, modified oil content, enhanced plant quality, enhanced digestibility and industrial usage. The gene or genes may be naturally occurring maize gene(s) (e.g., native traits) or transgene(s) introduced through genetic engineering techniques. The hybrid corn plants or seeds having inbred corn line BB202, AB8, AB18, AB19, BB84, BB85, BB95, BB98, BB201, BC106, BC137, CB20, or MN26 or a single gene conversion or a transgenic inbred corn line BB202, AB8, AB18, AB19, BB84, BB85, BB95, BB98, BB201, BC106, BC137, CB20, or MN26 as a parental line and having another, different, corn line as a second parental line as discussed above are comprised in the present invention.

Any DNA sequence(s), whether from a different species or from the same species that is inserted into the genome using transformation is referred to herein collectively as "transgenes." In some embodiments of the invention, a transformed variant of BB202, AB8, AB18, AB19, BB84, BB85, BB95, BB98, BB201, BC106, BC137, CB20, or MN26 may contain at least one transgene but could contain at least 1, 2, 3, 4, 5, 6, 7, 8, 9, or 10 transgenes. In another embodiment of the invention, a transformed variant of another corn line used as the other parental line may contain at least one transgene but could contain at least 1, 2, 3, 4, 5, 6, 7, 8, 9, or 10 transgenes, such as LH287, MON810, and MON89034.

In an embodiment of this invention is a method of making a backcross conversion of inbred corn line BB202, AB8, AB18, AB19, BB84, BB85, BB95, BB98, BB201, BC106, BC137, CB20, or MN26, comprising the steps of crossing a plant of corn inbred corn line BB202, AB8, AB18, AB19, BB84, BB85, BB95, BB98, BB201, BC106, BC137, CB20, or MN26 with a donor plant comprising a mutant gene or transgene conferring a desired trait, selecting an $F_1$ progeny plant comprising the mutant gene or transgene conferring the desired trait, and backcrossing the selected $F_1$ progeny plant to a plant of inbred corn line BB202, AB8, AB18, AB19, BB84, BB85, BB95, BB98, BB201, BC106, BC137, CB20, or MN26. This method may further comprise the step of obtaining a molecular marker profile of inbred corn line BB202, AB8, AB18, AB19, BB84, BB85, BB95, BB98, BB201, BC106, BC137, CB20, or MN26 and using the molecular marker profile to select for a progeny plant with the desired trait and the molecular marker profile of inbred corn line BB202, AB8, AB18, AB19, BB84, BB85, BB95, BB98, BB201, BC106, BC137, CB20, or MN26. In the same manner, this method may be used to produce an $F_1$ hybrid seed by adding a final step of crossing the desired trait conversion of inbred corn line BB202, AB8, AB18, AB19, BB84, BB85, BB95, BB98, BB201, BC106, BC137, CB20, or MN26 with a different corn plant to make $F_1$ hybrid corn seed comprising a mutant gene or transgene conferring the desired trait.

In some embodiments of the invention, the number of loci that may be backcrossed into inbred corn line BB202, AB8, AB18, AB19, BB84, BB85, BB95, BB98, BB201, BC106, BC137, CB20, or MN26 is at least 1, 2, 3, 4, or 5. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted locus.

In a preferred embodiment, the present invention provides methods for increasing and producing inbred corn line BB202, AB8, AB18, AB19, BB84, BB85, BB95, BB98, BB201, BC106, BC137, CB20, or MN26 seed, whether by crossing a first inbred parent corn plant with a second inbred parent corn plant and harvesting the resultant corn seed, wherein both said first and second inbred corn plant are the inbred corn line BB202, AB8, AB18, AB19, BB84, BB85, BB95, BB98, BB201, BC106, BC137, CB20, or MN26 or by planting an inbred corn seed of the inbred corn line BB202, AB8, AB18, AB19, BB84, BB85, BB95, BB98, BB201, BC106, BC137, CB20, or MN26, growing an inbred corn line BB202, AB8, AB18, AB19, BB84, BB85, BB95, BB98, BB201, BC106, BC137, CB20, or MN26 plant from said seed, controlling a self pollination of the plant where the pollen produced by the grown inbred corn line BB202, AB8, AB18, AB19, BB84, BB85, BB95, BB98, BB201, BC106, BC137, CB20, or MN26 plant pollinates the ovules produced by the very same inbred corn line BB202, AB8, AB18, AB19, BB84, BB85, BB95, BB98, BB201, BC106, BC137, CB20, or MN26 grown plant and harvesting the resultant seed.

The invention further provides methods for developing corn plants in a corn plant breeding program using plant breeding techniques including recurrent selection, backcrossing, pedigree breeding, molecular marker (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites, etc.) enhanced selection, genetic marker enhanced selection and transformation. Corn seeds, plants, and parts thereof produced by such breeding methods are also part of the invention.

In addition, any and all products made using the corn seeds, plants and parts thereof obtained from inbred corn line BB202, AB8, AB18, AB19, BB84, BB85, BB95, BB98, BB201, BC106, BC137, CB20, or MN26 or from any corn line produced using inbred corn line BB202, AB8, AB18, AB19, BB84, BB85, BB95, BB98, BB201, BC106, BC137, CB20, or MN26 as a direct or indirect parent are also part of the invention. Examples of such corn products include but are not limited to corn meal, corn flour, corn starch, corn syrup, corn sweetener and corn oil. The origin of the corn used in such corn products can be determined by tracking the source of the corn used to make the products and/or by using protein (isozyme, ELISA, etc.) and/or DNA (RFLP, PCR, SSR, SNP, EST, etc.) testing.

In addition to the exemplary aspects and embodiments described above, further aspects and embodiments will become apparent by study of the following descriptions.

Definitions

In the description and tables which follow, a number of terms are used. In order to provide a clear and consistent understanding of the specification and claims, including the scope to be given such terms, the following definitions are provided:

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

BT1-1, BT1. BT1-1 refers to MON810, also known as MON810Bt or BT1, is the designation given by the Monsanto Company (St. Louis, Mo.) for the transgenic event that, when expressed in maize, produces an endotoxin that is efficacious against the European corn borer, *Ostrinia nubilalis* and certain other Lepidopteran larvae.

Collection of seeds. In the context of the present invention a collection of seeds will be a grouping of seeds mainly containing similar kind of seeds, for example hybrid seeds having the inbred line of the invention as a parental line, but that may also contain, mixed together with this first kind of seeds, a second, different kind of seeds, of one of the inbred parent lines, for example the inbred line of the present invention. A commercial bag of hybrid seeds having the inbred line of the invention as a parental line and containing also the inbred line seeds of the invention would be, for example such a collection of seeds.

CL. CL, also known as Clearfield is commercial denomination given to the gene that, when present in maize, allows the use of imidazolinone herbicides as a weed control agent for both grasses (i.e., monocotyledons) and broadleaves (i.e., dicotyledons).

Daily heat unit value. The daily heat unit value (also referred to as growing degree unit, or GDU) is calculated as follows: (the maximum daily temperature+the minimum daily temperature)/2 minus 50. All temperatures are in degrees Fahrenheit. The maximum temperature threshold is 86 degrees, if temperatures exceed this, 86 is used. The minimum temperature threshold is 50 degrees, if temperatures go below this, 50 is used. For each hybrid, it takes a certain number of GDUs to reach various stages of plant development. GDUs are a way of measuring plant maturity. GDUs can also relate to stages of growth for an inbred line.

Decreased vigor. A plant having a decreased vigor in the present invention is a plant that, compared to other plants has a less vigorous appearance for vegetative and/or reproductive characteristics including shorter plant height, small ear size, ear and kernel shape, ear color or other characteristics.

Dropped ears. This is a measure of the number of dropped ears per plot, and represents the percentage of plants that dropped an ear prior to harvest.

Dry down. This is the rate at which a hybrid will reach acceptable harvest moisture.

Ear height. The ear height is a measure from the ground to the upper ear node attachment, and is measured in centimeters.

Essentially all of the physiological and morphological characteristics. A plant having essentially all of the physiological and morphological characteristics means a plant having the physiological and morphological characteristics of the recurrent parent, except for the characteristics derived from the converted gene.

GDU pollen. The number of heat units from planting until 50% of the plants in the inbred or hybrid are shedding pollen.

GDU silk. The GDU silk (=heat unit silk) is the number of growing degree units (GDU) or heat units required for an inbred line or hybrid to reach silk emergence from the time of planting.

Harvest aspect. This is a visual rating given the day of harvest or the previous day. Hybrids are rated 1 (poorest) to 9 (best) with poorer scores given for poor plant health, visible signs of fungal infection, poor plant intactness characterized by missing leaves, tassels, or other vegetative parts, or a combination of these traits.

Herbicide resistant or tolerant. A plant containing any herbicide-resistant gene or any DNA molecule or construct (or replicate thereof) which is not naturally occurring in the plant which results in increase tolerance to any herbicide including, imidazoline, sulfonylurea, glyphosate, glufosinate, L-phosphinothricin, triazine and benzonitrile. For purposes of this definition, a DNA molecule or construct shall be considered to be naturally occurring if it exists in a plant at a high enough frequency to provide herbicide resistance without further selection and/or if it has not been produced as a result of tissue culture selection, mutagenesis, genetic engineering using recombinant DNA techniques or other in vitro or in vivo modification to the plant.

Inbreeding depression. The inbreeding depression is the loss of performance of the inbreds due to the effect of inbreeding, i.e., due to the mating of relatives or to self-pollination. It increases the homozygous recessive alleles leading to plants which are weaker and smaller and having other less desirable traits.

Late plant greenness. Similar to a stay green rating. This is a visual assessment given at around the dent stage but typically a few weeks before harvest to characterize the degree of greenness left in the leaves. Plants are rated from 1 (poorest) to 9 (best) with poorer scores given for plants that have more non-green leaf tissue typically due to early senescence or from disease.

MN RM. This represents the Minnesota Relative Maturity Rating (MN RM) for the hybrid and is based on the harvest moisture of the grain relative to a standard set of checks of previously determined MN RM rating. Regression analysis is used to compute this rating.

Moisture. The moisture is the actual percentage moisture of the grain at harvest.

Plant cell. Plant cell, as used herein includes plant cells whether isolated, in tissue culture, or incorporated in a plant or plant part.

Plant habit. This is a visual assessment assigned during the late vegetative to early reproductive stages to characterize the plant's leaf habit. It ranges from decumbent with leaves growing horizontally from the stalk to a very upright leaf habit, with leaves growing near vertically from the stalk.

Plant height. This is a measure of the height of the hybrid from the ground to the tip of the tassel, and is measured in centimeters.

Plant intactness. This is a visual assessment assigned to a hybrid or inbred at or close to harvest to indicate the degree that the plant has suffered disintegration through the growing season. Plants are rated from 1 (poorest) to 9 (best) with poorer scores given for plants that have more of their leaf blades missing.

Plant part. As used herein, the term "plant part" includes any part of the plant including but not limited to leaves, stems, roots, seeds, grains, embryos, pollens, ovules, flowers, ears, cobs, husks, stalks, root tips, anthers, silk, tissue, cells and the like.

Pollen shed. This is a visual rating assigned at flowering to describe the abundance of pollen produced by the anthers. Inbreds are rated 1 (poorest) to 9 (best) with the best scores for inbreds with tassels that shed more pollen during anthesis.

Post-anthesis root lodging. This is a percentage plants that root lodge after anthesis: plants that lean from the vertical axis at an approximately 30° angle or greater.

Pre-anthesis brittle snapping. This is a percentage of "snapped" plants following severe winds prior to anthesis.

Pre-anthesis root lodging. This is a percentage plants that root lodge prior to anthesis: plants that lean from the vertical axis at an approximately 30° angle or greater.

Predicted RM. This trait for a hybrid, predicted relative maturity (RM), is based on the harvest moisture of the grain. The relative maturity rating is based on a known set of checks and utilizes conventional maturity such as the Comparative Relative Maturity Rating System or its similar, the Minnesota Relative Maturity Rating System.

Quantitative trait loci (QTL). Quantitative trait loci refer to genetic loci that control to some degree numerically representable traits that are usually continuously distributed.

RBDHV, CCR1, CRW2-1. RBDHV, CCR1 or CRW2-1 refers to MON88017, also known as MON88017CCR1, is the transgenic event that, when expressed in maize, allows the use of glyphosate as a weed control agent. In addition, this event produces an endotoxin that is efficacious against the corn root worm, *Diabrotica virgifera*, and certain other Coleopteran larvae.

Regeneration. Regeneration refers to the development of a plant from tissue culture.

RMQKZ, RMQKC, RMQKD. RMQKZ, RMQKC, or RMQKD refers to a combination of Mon88017 (see below) and Mon89034 transgenes for insect resistance and gyphosate tolerance. Mon89034 is a transgenic event expressed in maize, that produces an endotoxin that is efficacious against the European corn borer, *Ostrinia nubilalis* and certain other Lepidopteran larvae.

RHTTZ, RR2. RHTZZ and RR2 refers to MON603, also known as MON603RR2, better known as NK603, is the designation for the transgenic event that, when expressed in maize, allows the use of glyphosate as a weed control agent on the crop. Another transgenic event, GA21, when expressed in maize, also allows the use of glyphosate as a weed control agent on the crop.

Root lodging. The root lodging is the percentage of plants that root lodge; i.e., those that lean from the vertical axis at an approximate 30° angle or greater would be counted as root lodged.

Seed quality. This is a visual rating assigned to the kernels of the inbred. Kernels are rated 1 (poorest) to 9 (best) with poorer scores given for kernels that are very soft and shriveled with splitting of the pericarp visible and better scores for fully formed kernels.

Seedling vigor. This is the vegetative growth after emergence at the seedling stage, approximately five leaves.

Silking ability. This is a visual assessment given during flowering. Plants are rated on the amount and timing of silk production. Plants are rated from 1 (poorest) to 9 (best) with poorer scores given for plants that produce very little silks that are delayed past pollen shed.

Single gene converted. Single gene converted or conversion plants refers to plants which are developed by a plant breeding technique called backcrossing wherein essentially all the morphological and physiological characteristics of an inbred are recovered in addition to the single gene transferred into the inbred via the backcrossing technique or via genetic engineering. This also includes multiple transference of single genes.

Stalk lodging. This is the percentage of plants that stalk lodge, i.e., stalk breakage, as measured by either natural lodging or pushing the stalks and determining the percentage of plants that break off below the ear. This is a relative rating of a hybrid to other hybrids for standability.

Standability. A term referring to the how well a plant remains upright towards the end of the growing season. Plants with excessive stalk breakage and/or root lodging would be considered to have poor standability.

Stay green. Stay green is the measure of plant health near the time of black layer formation (physiological maturity). A high score indicates better late-season plant health.

Transgenic. Where an inbred line has been converted to contain one or more transgenes by single gene conversion or by direct transformation.

Variety. A plant variety as used by one skilled in the art of plant breeding means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International Convention for the Protection of New Varieties of Plants).

Yield (Bushels/Acre). The yield is the actual yield of the grain at harvest adjusted to 15.5% moisture.

ZKDDZ. ZKDDZ refers to MON810, also known as MON810Bt or BT1, is the designation given by the Monsanto Company (St. Louis, Mo.) for the transgenic event that, when expressed in maize, produces an endotoxin that is efficacious against the European corn borer, *Ostrinia nubilalis* and certain other Lepidopteran larvae.

AM1—Optimum® AcreMax® 1 Insect Protection System with an integrated corn rootworm refuge solution includes HXX, LL, RR2. Optimum AcreMax 1 products contain the LibertyLink® gene and can be sprayed with Liberty® herbicide HR—contains HX1—Contains the Herculex® insect Protection gene which provides protection against European corn borer, southwestern corn borer, black cutworm, fall armyworm, western bean cutworm, lesser corn stalk borer, southern corn stalk borer, and sugarcane borer; and suppresses corn earworm. LL—Contains the LibertyLink® gene for resistance to Liberty® herbicide RR2—Contains the Roundup Ready® Corn 2 trait that provides crop safety for over-the-top applications of labeled glyphosate herbicides.

RIB Refuge-in-the-Bag technology offers simpler refuge management and effective insect protection.

HXRW—The Herculex® RW insect protection trait contains proteins that provide enhanced resistance against western corn rootworm, northern corn rootworm and Mexican corn rootworm. HXX—Herculex® XTRA contains the Herculex I and Herculex RW genes ZNYKZ—VT PRO, contains mon 89034 for insect control.

RBDHZ—VTRR2, Yieldgard VT Rootworm (mon 88017) with Roundup Ready 2 for applications of glyphosate herbicides.

RPGJZ—VT2P, genuity VT Double Pro. Contains mon 89034 for insect control and NK603 for Roundup Ready herbicide tolerance.

GJLHZ—VT3P/HX1, genuity VT Triple Pro/Herculex 1. Contains mon 88017, mon 89034, & TC1507 for insect control. Includes NK603 for Roundup Ready herbicide tolerance and PAT for Glufosinate herbicide tolerance.

LMSLZ—+HXT, Herculex1/Herculex Rootworm Corn. Contains D59122-7 & TC1507 for insect control. Includes PAT for Glufosinate herbicide tolerance.

LFWMZ—HXcrw, Herculex Rootworm Corn. Contains D59122-7 for insect control. Includes PAT for Glufosinate herbicide tolerance.

GT—GA21, glyphosate tolerance

RW—Agrisure corn rootworm protection. Contains MIR604

CB/LL/RW—Agrisure corn borer & corn rootworm protection. Contains BT11, MIR604 for insect control and PAT for Glufosinate herbicide tolerance.

DETAILED DESCRIPTION OF THE INVENTION

Inbred corn line BB202, AB8, AB18, AB19, BB84, BB85, BB95, BB98, BB201, BC106, BC137, CB20, or MN26 is a corn inbred with superior characteristics, and provides very good parental lines in crosses for producing first generation ($F_1$) hybrid corn. Inbred corn line BB202, AB8, AB18, AB19, BB84, BB85, BB95, BB98, BB201, BC106, BC137, CB20, or MN26 is best adapted to the East, Central, South and Western regions of the United States Corn Belt in the zones that are commonly referred to as Zones 5, 6 and 7. Hybrids that are adapted to these maturity zones can be grown on a significant number of acres as it relates to the total of the USA corn acres. Heterotic background and relative maturity of the line are shown below:

| Line | Heterotic Background | Relative Maturity |
|------|---------------------|-------------------|
| BB202 | B73, B14 | 109 |

BB202, AB8, AB18, AB19, BB84, BB85, BB95, BB98, BB201, BC106, BC137, CB20, or MN26 is an inbred corn line with high yield potential in hybrids. Hybrids with inbred corn line BB202, AB8, AB18, AB19, BB84, BB85, BB95, BB98, BB201, BC106, BC137, CB20, or MN26 as one parental line produce uniform, consistent sized ears with a high kernel row number and heavy, hard-textured kernels. Often these hybrid combinations result in plants which are appreciably better than average for stalk strength, grain yield, and test weight when compared to inbred lines of similar maturity and geographical adaptability. Some of the criteria used to select ears in various generations include: yield, yield to harvest moisture ratio, stalk quality, root quality, disease tolerance with emphasis on grey leaf spot, test weight, late season plant greenness, late season plant intactness, ear retention, ear height, pollen shedding ability, silking ability, and corn borer tolerance. During the development and selection of the line, crosses were made to inbred testers for the purpose of estimating the line's general and specific combining ability, and evaluations were run by the Ames, Iowa Research Station. The inbred was evaluated further as a line and in numerous crosses by the Ames station and other research stations across the Corn Belt. The inbred has proven to have an excellent combining ability in hybrid combinations.

Inbred corn line BB202, AB8, AB18, AB19, BB84, BB85, BB95, BB98, BB201, BC106, BC137, CB20, or MN26 has shown uniformity and stability for the traits, within the limits of environmental influence for the traits. These lines have been increased with continued observation for uniformity of plant type. Inbred corn line BB202, AB8, AB18, AB19, BB84, BB85, BB95, BB98, BB201, BC106, BC137, CB20, or MN26 has the following morphologic and other characteristics (based primarily on data collected at Ames, Iowa).

TABLE 1A - BB202 VARIETY DESCRIPTION INFORMATION

General Plant Information:

Type: BB202 is a yellow, dent corn inbred
Region where developed: Ames, Iowa
Maturity: 109 RM

| | Heat Units |
|---|---|
| From planting to 50% of plants in silk: | 1509 |
| From planting to 50% of plants in pollen: | 1481 |

Plant:

Plant height to tassel tip: 225.0 cm
Ear height to base of top ear: 61.0 cm
Average length of top ear internode: 14.7 cm
Average number of tillers: 0
Average number of ears per stalk: 2
Anthocyanin of brace roots: Faint, banded
Leaf:

Width of ear node leaf: 8.9 cm
Length of ear node leaf: 117.6 cm
Number of leaves above top ear: 6.0
Leaf angle (from 2nd leaf above ear at anthesis to stalk above leaf): 10.0°
Leaf color: Greenish yellow Munsell 5GY 4/4
Leaf sheath pubescence (Rated on scale from 1 = none to 9 = like peach fuzz): 3
Marginal waves (Rated on scale from 1 = none to 9 = many): 5
Longitudinal creases (Rated on scale from 1 = none to 9 = many): 4
Tassel:

Number of lateral branches: 9.0
Branch angle from central spike: 48°
Tassel length (from top leaf collar to tassel top): 40.0 cm
Pollen shed (Rated on scale from 0 = male sterile to 9 = heavy shed): 8
Anther color: Greenish yellow Munsell 2.5 GY 7/10
Glume color: Greenish yellow Munsell 5 GY 5/6
Tassel glume bands color: Absent
Ear (Unhusked Data):

Silk color (3 days after emergence): Greenish yellow Munsell 2.5 GY 8.5/8
Fresh husk color (25 days after 50% silking): Green yellow Munsell 5 GY 7/8
Dry husk color (65 days after 50% silking): Yellow brown Munsell 2.5 Y 9/2
Position of ear: ___
Husk tightness (Rated on scale from 1 = very loose to 9 = very tight): ___
Husk extension at harvest: 54.8 mm
Ear (Husked Ear Data):

Ear length: 15.5 cm
Ear diameter at mid-point: 3.9 cm

-continued

Ear weight: 113.6 g
Number of kernel rows: 14.7
Row alignment: Straight
Ear taper: Slight
Kernel (Dried):

Kernel length: 11.0 mm
Kernel width: 7.5 mm
Kernel thickness: 4.2 mm
Hard endosperm color: Yellow red Munsell 7.5YR 5/8
Endosperm type: Dent
Weight per 100 kernels (unsized sample): 23.8 g
Cob:

Cob diameter at mid-point: 20.3 mm
Cob color: Red Munsell 5R 5/8
Agronomic Traits:

Dropped ears (at 65 days after anthesis): ___%
Pre-anthesis brittle snapping: 0%
Pre-anthesis root lodging: 0%

TABLE 1B - AB8 VARIETY DESCRIPTION INFORMATION

General Plant Information:

Type: AB8 is a yellow, dent corn inbred
Region where developed: Chatham, Ontario, Canada
Maturity:

| | Heat Units |
|---|---|
| From planting to 50% of plants in silk: | 1200 |
| From planting to 50% of plants in pollen: | 1190 |

Plant:

Plant height to tassel tip: 245.3 cm
Ear height to base of top ear: 93 cm
Average length of top ear internode: 15.9 cm
Average number of tillers: 0.1
Average number of ears per stalk: 1.9
Anthocyanin of brace roots: Absent
Leaf:

Width of ear node leaf: 9.66 cm
Length of ear node leaf: 68.4 cm
Number of leaves above top ear: 6.5
Leaf angle (from 2nd leaf above ear at anthesis to stalk above leaf): 30.5°
Leaf color: Munsell 2.5GY 5/2
Leaf sheath pubescence (Rated on scale from 1 = none to 9 = like peach fuzz): 2
Marginal waves (Rated on scale from 1 = none to 9 = many): 4.5
Longitudinal creases (Rated on scale from 1 = none to 9 = many): 5.5
Tassel:

Number of lateral branches: 5.4
Branch angle from central spike: 24.5°
Tassel length (from top leaf collar to tassel top): 34.1 cm
Pollen shed (Rated on scale from 0 = male sterile to 9 = heavy shed): 7
Anther color: Munsell 7.5 YR 8/4
Glume color: Munsell 5 R 4/10
Tassel glume bands color: Absent
Ear (Unhusked Data):

Silk color (3 days after emergence): Munsell 2.5 GY 8/10
Fresh husk color (25 days after 50% silking): Munsell 7.5 GY 7/8
Dry husk color (65 days after 50% silking): Munsell 2.5GY 7/6
Position of ear: Down
Husk tightness (Rated on scale from 1 = very loose to 9 = very tight): 4
Husk extension at harvest: 51 mm
Ear (Husked Ear Data):

Ear length: 12.7 cm
Ear diameter at mid-point: 3.8 cm
Ear weight: 109.4 g
Number of kernel rows: 18
Row alignment: Straight
Ear taper: Round Kernel (Dried):

Kernel length: 14.8 mm
Kernel width: 6.4 mm
Kernel thickness: 3.2 mm
Hard endosperm color: Munsell 2.5 Y 8/10
Endosperm type: Dent
Weight per 100 kernels (unsized sample): 23.0 g
Cob:

Cob diameter at mid-point: 35.4 mm
Cob color: White
Agronomic Traits:

Dropped ears (at 65 days after anthesis): 0%
Pre-anthesis brittle snapping: 0%
Pre-anthesis root lodging: 0%

TABLE 1C - AB18 VARIETY DESCRIPTION INFORMATION

General Plant Information:

Type: AB18 is a yellow, dent corn inbred
Region where developed: Chatham, Ontario, Canada
Maturity:

| | Heat Units |
|---|---|
| From planting to 50% of plants in silk: | 1125 |
| From planting to 50% of plants in pollen: | 1125 |

Plant:

Plant height to tassel tip: 250.0 cm
Ear height to base of top ear: 83.5 cm
Average length of top ear internode: 15.5 cm
Average number of tillers: 0
Average number of ears per stalk: 2.0
Anthocyanin of brace roots: Absent
Leaf:

Width of ear node leaf: 9.4 cm
Length of ear node leaf: 92.4 cm
Number of leaves above top ear: 7.0
Leaf angle (from 2nd leaf above ear at anthesis to stalk above leaf): 18°
Leaf color: Munsell 5GY 3/4
Leaf sheath pubescence (Rated on scale from 1 = none to 9 = like peach fuzz): 3
Marginal waves (Rated on scale from 1 = none to 9 = many): 7
Longitudinal creases (Rated on scale from 1 = none to 9 = many): 5
Tassel:

Number of lateral branches: 7.8
Branch angle from central spike: 51°
Tassel length (from top leaf collar to tassel top): 44.2 cm
Pollen shed (Rated on scale from 0 = male sterile to 9 = heavy shed): 7
Anther color: Munsell 5 YR 8/2
Glume color: Munsell 5 GY 7/8
Tassel glume bands color: Absent
Ear (Unhusked Data):

Silk color (3 days after emergence): Munsell 2.5 GY 8/12
Fresh husk color (25 days after 50% silking): Munsell 5GY 6/6
Dry husk color (65 days after 50% silking): Munsell 5Y 8/6
Position of ear: vertical down
Husk tightness (Rated on scale from 1 = very loose to 9 = very tight): 7
Husk extension at harvest: 51 mm
Ear (Husked Ear Data):

Ear length: 14.7 cm
Ear diameter at mid-point: 4.4 cm
Ear weight: 139.1 g
Number of kernel rows: 14
Row alignment: Straight
Ear taper: None
Kernel (Dried):

Kernel length: 13.8 mm
Kernel width: 8.1 mm
Kernel thickness: 4.2 mm
Hard endosperm color: Munsell 2.5 Y 8/10
Endosperm type: Dent
Weight per 100 kernels (unsized sample): 30.2 g
Cob:

Cob diameter at mid-point: 23.9 mm
Cob color: Red, Munsell 2.5 YR 4/6
Agronomic Traits:

Dropped ears (at 65 days after anthesis): 0%
Pre-anthesis brittle snapping: 0%
Pre-anthesis root lodging: 0%

TABLE 1D - AB19 VARIETY DESCRIPTION INFORMATION

General Plant Information:

Type: AB19 is a yellow dent corn inbred
Region where developed: Morris, Minnesota
Maturity:

| | Heat Units: |
|---|---|
| From planting to 50% of plants in silk: | 1323.4 |
| From planting to 50% of plants in pollen: | 1315.6 |

Plant:

Plant height to tassel tip: 197.0 cm
Ear height to base of top ear: 70.5 cm
Average length of top ear internode: 15.1 cm
Average number of tillers: 0
Average number of ears per stalk: 2
Anthocyanin of brace roots: yes
Leaf:

Width of ear node leaf: 8.5 cm
Length of ear node leaf: 74.65 cm
Number of leaves above top ear: 6.3 (average of 10 plants)
Leaf angle (from $2^{nd}$ leaf above ear at anthesis to stalk above leaf): 30-45°
Leaf color: 5GY 5/4
Leaf sheath pubescence (rated on scale from 1 = none, to 9 = like peach fuzz): 2
Marginal waves (rated on scale from 1 = none, to 9 = many): 3
Longitudinal creases (rated on scale from 1 = none, to 9 = many): 3
Tassel:

Number of lateral branches: 8.0
Branch angle from central spike: 15-20°
Tassel length (from base of tassel to tassel top): 40.9 cm
Pollen shed (rated on scale from 0 = male sterile, to 9 = heavy shed): 6
Anther color: 5Y 8/8
Glume color: 2.5GY 7/6-5R 6/8
Tassel glume bands color: Absent
Ear (Unhusked Data):

Silk color (3 days after emergence): 2.5GY 8/8
Fresh husk color (25 days after 50% silking): 2.5GY 7/8
Dry husk color (65 days after 50% silking): 2.5Y 8/4
Position of ear: mostly hanging, some tilting
Husk tightness (rated on scale from 1 = very loose, to 9 = very tight): 2.5
Husk extension at harvest: past the ear
Ear (Husked Ear Data):

Ear length: 14.05 cm
Ear diameter at mid-point: 38.0 mm
Ear weight: 83.8 g
Number of kernel rows: 14.2 (average of 10 plants)
Row alignment: not straight
Shank length: 10.1 cm
Ear taper: tapered
Kernel (Dried):

Kernel length: 7.65 mm
Kernel width: 5.1 mm
Kernel thickness: 3.45 mm
Hard endosperm color: 2.5Y 8/10
Endosperm type: dent
Weight per 100 kernels (unsized sample): 27.0 g -continued Cob:

Cob diameter at mid-point: 20.0 mm
Cob color: 2.5YR 3/6
Argonomic Traits:

Dropped ears (at 65 days after anthesis): 0%
Pre-anthesis brittle snapping: 0%
Pre-anthesis root lodging: 0%
Post-anthesis root lodging (at 65 days after anthesis): 0%

TABLE 1E - BB84 VARIETY DESCRIPTION INFORMATION

General Plant Information:

Type: BB84 is a yellow, dent corn inbred
Region where developed: Lebanon, IN
Maturity: Zone 7

| | Heat Units: |
|---|---|
| From planting to 50% of plants in silk: | 1540.7 |
| From planting to 50% of plants in pollen: | 1515.2 |

Plant:

Plant height to tassel tip: 230.0 cm
Ear height to base of top ear: 92.5 cm
Average length of top ear internode: 31.5 cm
Average number of tillers: 0
Average number of ears per stalk: 2.0
Anthocyanin of brace roots: Absent
Leaf:

Width of ear node leaf: 7.74 cm
Length of ear node leaf: 76.0 cm
Number of leaves above top ear: 5
Leaf angle (from 2nd leaf above ear at anthesis to stalk above leaf): 75°
Leaf color: 7.5GY 4/4
Leaf sheath pubescence (Rated on scale from 1 = none to 9 = like peach fuzz): 2
Marginal waves (Rated on scale from 1 = none to 9 = many): 4
Longitudinal creases (Rated on scale from 1 = none to 9 = many): 6
Tassel:

Number of lateral branches: 5
Branch angle from central spike: 30°
Tassel length (from top leaf collar to tassel top): 37.0 cm
Pollen shed (Rated on scale from 0 = male sterile to 9 = heavy shed): 7
Anther color: N/A
Glume color: 5 GY 6/10
Tassel glume bands color: Absent
Ear (Unhusked Data):

Silk color (3 days after emergence): light green
Fresh husk color (25 days after 50% silking): 2.5GY 6/10
Dry husk color (65 days after 50% silking): 5Y 8/4
Position of ear: Pendent
Husk tightness: 7
Husk extension at harvest: 4 cm
Ear (Husked Ear Data):

Ear length: 16.875 cm
Ear diameter at mid-point: 19 mm
Ear weight: 116.2 g
Number of kernel rows: 14.5
Row alignment: Straight
Shank length: 7.87 cm
Ear taper: cylindrical
Kernel (Dried):

Kernel length: 10.75 mm
Kernel width: N/A
Kernel thickness: 4.25 mm
Hard endosperm color: white
Endosperm type: Hard
Weight per 100 kernels (unsized sample): 25.6
Cob:

Cob diameter at mid-point: 9.5 mm
Cob color: N/A

Agronomic Traits:

Dropped ears (at 65 days after anthesis): N/A
Pre-anthesis brittle snapping: N/A
Pre-anthesis root lodging: N/A
Post-anthesis root lodging (at 65 days after anthesis): N/A

TABLE 1F - BB85 VARIETY DESCRIPTION INFORMATION

General Plant Information:

Type: BB85 is a yellow, dent corn inbred
Region where developed: Lebanon, IN
Maturity: Zone 7

| | Heat Units: |
|---|---|
| From planting to 50% of plants in silk: | 1481.1 |
| From planting to 50% of plants in pollen: | 1448.3 |

Plant:

Plant height to tassel tip: 221.0 cm
Ear height to base of top ear: 60.96 cm
Average length of top ear internode: 10.16 cm
Average number of tillers: 0
Average number of ears per stalk: 2.0
Anthocyanin of brace roots: Absent
Leaf:

Width of ear node leaf: 7.87 cm
Length of ear node leaf: 63.5 cm
Number of leaves above top ear: 7
Leaf angle (from 2nd leaf above ear at anthesis to stalk above leaf): 90°
Leaf color: 7.5GY 3/2
Leaf sheath pubescence (Rated on scale from 1 = none to 9 = like peach fuzz): 1
Marginal waves (Rated on scale from 1 = none to 9 = many): 2
Longitudinal creases (Rated on scale from 1 = none to 9 = many): 6
Tassel:

Number of lateral branches: 5
Branch angle from central spike: 35°
Tassel length (from top leaf collar to tassel top): 38.0 cm
Pollen shed (Rated on scale from 0 = male sterile to 9 = heavy shed): 7
Anther color: 5Y7/10
Glume color: 2.5 GY 8/4
Tassel glume bands color: Absent
Ear (Unhusked Data):

Silk color (3 days after emergence): 5Y 8/6
Fresh husk color (25 days after 50% silking): 7.5GY 8/8
Dry husk color (65 days after 50% silking): 2.5Y 8/4
Position of ear: Pendent
Husk tightness: 8
Husk extension at harvest: 2.54 cm
Ear (Husked Ear Data):

Ear length: 13.5 cm
Ear diameter at mid-point: 28 mm
Ear weight: 145.3 g
Number of kernel rows: 18
Row alignment: Slight Bend
Shank length: 6.5 cm
Ear taper: cylindrical
Kernel (Dried):

Kernel length: 15 mm
Kernel width: N/A
Kernel thickness: 4 mm
Hard endosperm color: white
Endosperm type: Hard
Weight per 100 kernels (unsized sample): 38.2 g
Cob:

Cob diameter at mid-point: 25 mm
Cob color: N/A
Agronomic Traits:

Dropped ears (at 65 days after anthesis): N/A
Pre-anthesis brittle snapping: N/A Pre-anthesis root lodging: N/A
Post-anthesis root lodging (at 65 days after anthesis): N/A

TABLE 1G - BB95 VARIETY DESCRIPTION INFORMATION

General Plant Information:

Type: BB95 is a yellow, dent corn inbred
Region where developed: Lebanon, IN
Maturity: Zone 7

|  | Heat Units: |
|---|---|
| From planting to 50% of plants in silk: | 1481.1 |
| From planting to 50% of plants in pollen: | 1481.1 |

Plant:

Plant height to tassel tip: 213.36 cm
Ear height to base of top ear: 60.96 cm
Average length of top ear internode: 15.24 cm
Average number of tillers: 0
Average number of ears per stalk: 2.0
Anthocyanin of brace roots: Absent
Leaf:

Width of ear node leaf: 7.62 cm
Length of ear node leaf: 80.64 cm
Number of leaves above top ear: 7
Leaf angle (from 2nd leaf above ear at anthesis to stalk above leaf): 45°
Leaf color: 7.5GY 4/4
Leaf sheath pubescence (Rated on scale from 1 = none to 9 = like peach fuzz): 6
Marginal waves (Rated on scale from 1 = none to 9 = many): 4
Longitudinal creases (Rated on scale from 1 = none to 9 = many): 2
Tassel:

Number of lateral branches: 7
Branch angle from central spike: 55°
Tassel length (from top leaf collar to tassel top): 38.0 cm
Pollen shed (Rated on scale from 0 = male sterile to 9 = heavy shed): 7
Anther color: 5Y 7/10
Glume color: 2.5 GY 6/4
Tassel glume bands color: Absent
Ear (Unhusked Data):

Silk color (3 days after emergence): 5Y 8/8
Fresh husk color (25 days after 50% silking): 7.5GY 8/2
Dry husk color (65 days after 50% silking): 2.5Y 7/6
Position of ear: Pendent
Husk tightness: 3
Husk extension at harvest: 2.54 cm
Ear (Husked Ear Data):

Ear length: 15 cm
Ear diameter at mid-point: 40 mm
Ear weight: 121.9 g
Number of kernel rows: 14
Row alignment: Poorly Aligned
Shank length: 10 cm
Ear taper: conico-cylindrical
Kernel (Dried):

Kernel length: 11 mm
Kernel width: N/A
Kernel thickness: 7 mm
Hard endosperm color: Grey
Endosperm type: Dent
Weight per 100 kernels (unsized sample): 28.5 g
Cob:

Cob diameter at mid-point: 25 mm
Cob color: N/A
Agronomic Traits:

Dropped ears (at 65 days after anthesis): N/A
Pre-anthesis brittle snapping: N/A
Pre-anthesis root lodging: N/A
Post-anthesis root lodging (at 65 days after anthesis): N/A

TABLE 1H - BB98 VARIETY DESCRIPTION INFORMATION

General Plant Information:

Type: BB98 is a yellow, dent corn inbred
Region where developed: Ames, Iowa
Maturity:

|  | Heat Units: |
|---|---|
| From planting to 50% of plants in silk: | 1566 |
| From planting to 50% of plants in pollen: | 1647 |

Plant:

Plant height to tassel tip: 220.0 cm
Ear height to base of top ear:
Average length of top ear internode:
Average number of tillers: 0
Average number of ears per stalk: 1.0
Anthocyanin of brace roots: Moderate
Leaf:

Width of ear node leaf: 9.5 cm
Length of ear node leaf:
Number of leaves above top ear:
Leaf angle (from 2nd leaf above ear at anthesis to stalk above leaf): 28°
Leaf color: Medium green
Leaf sheath pubescence (Rated on scale from 1 = none to 9 = like peach fuzz):
Marginal waves (Rated on scale from 1 = none to 9 = many):
Longitudinal creases (Rated on scale from 1 = none to 9 = many):
Tassel:

Number of lateral branches: 7.0
Branch angle from central spike:
Tassel length (from top leaf collar to tassel top):
Pollen shed (Rated on scale from 0 = male sterile to 9 = heavy shed):
Anther color: Yellow
Glume color: Green
Tassel glume bands color: Present
Ear (Unhusked Data):

Silk color (3 days after emergence): Pale green
Fresh husk color (25 days after 50% silking):
Dry husk color (65 days after 50% silking):
Position of ear:
Husk tightness
Husk extension at harvest:
Ear (Husked Ear Data):

Ear length: 12.3 cm
Ear diameter at mid-point:
Ear weight:
Number of kernel rows: 14.7
Row alignment: Straight
Shank length:
Ear taper: Slight
Kernel (Dried):

Kernel length: 11.0 mm
Kernel width:
Kernel thickness:
Hard endosperm color: Yellow
Endosperm type: Dent
Weight per 100 kernels (unsized sample):
Cob:

Cob diameter at mid-point:
Cob color: Red
Agronomic Traits:

Dropped ears (at 65 days after anthesis):
Pre-anthesis brittle snapping:
Pre-anthesis root lodging:
Post-anthesis root lodging (at 65 days after anthesis):

-continued

TABLE 1I - BB201 VARIETY DESCRIPTION INFORMATION

General Plant Information:

Type: BB201 is a yellow, dent corn inbred
Region where developed: Ames, Iowa
Maturity:

| | Heat Units: |
|---|---|
| From planting to 50% of plants in silk: | 1509 |
| From planting to 50% of plants in pollen: | 1481 |

Plant:

Plant height to tassel tip: 203.7 cm
Ear height to base of top ear: 73.7 cm
Average length of top ear internode: 13.8 cm
Average number of tillers: 0.1
Average number of ears per stalk: 3.0
Anthocyanin of brace roots: Faint
Leaf:

Width of ear node leaf: 7.5 cm
Length of ear node leaf: 76.8 cm
Number of leaves above top ear: 6.0
Leaf angle (from 2nd leaf above ear at anthesis to stalk above leaf): 28°
Leaf color: Greenish yellow Munsell 7.5GY 4/4
Leaf sheath pubescence (Rated on scale from 1 = none to 9 = like peach fuzz): 7
Marginal waves (Rated on scale from 1 = none to 9 = many): 8
Longitudinal creases (Rated on scale from 1 = none to 9 = many): 2
Tassel:

Number of lateral branches: 9.0
Branch angle from central spike: 40°
Tassel length (from top leaf collar to tassel top): 28.5 cm
Pollen shed (Rated on scale from 0 = male sterile to 9 = heavy shed): 7
Anther color: Yellow Munsell 10Y 6/8
Glume color: Greenish yellow Munsell 5 GY 5/6
Tassel glume bands color: Absent
Ear (Unhusked Data):

Silk color (3 days after emergence): Greenish yellow Munsell 2.5 GY 8/8
Fresh husk color (25 days after 50% silking): Green yellow Munsell 7.5 GY 5/8
Dry husk color (65 days after 50% silking): Yellow brown Munsell 2.5Y 9/2
Position of ear:
Husk tightness (Rated on scale from 1 = very loose to 9 = very tight):
Husk extension at harvest: 53.2 mm
Ear (Husked Ear Data):

Ear length: 13.0 cm
Ear diameter at mid-point: 3.7 cm
Ear weight: 89 g
Number of kernel rows: 13.7
Row alignment: Slightly crooked
Shank length: 15.8 cm
Ear taper: Slight
Kernel (Dried):

Kernel length: 11.0 mm
Kernel width: 7.3 mm
Kernel thickness: 4.7 mm
Hard endosperm color: Yellow red Munsell 7.5 YR 6/10
Endosperm type: Dent
Weight per 100 kernels (unsized sample): 23.8 g
Cob:

Cob diameter at mid-point: 17.8 mm
Cob color: Red Munsell 10R 6/8
Agronomic Traits:

Dropped ears (at 65 days after anthesis):
Pre-anthesis brittle snapping: 0.0%
Pre-anthesis root lodging: 0.0%
Post-anthesis root lodging (at 65 days after anthesis):

-continued

TABLE 1J - BC106 VARIETY DESCRIPTION INFORMATION

General Plant Information:

Type: BC106 is a yellow, dent corn inbred
Region where developed: Champaign, IL
Maturity:

| | Heat Units: |
|---|---|
| From planting to 50% of plants in silk: | 1409.5 |
| From planting to 50% of plants in pollen: | 1359.5 |

Plant:

Plant height to tassel tip: 200.0 cm
Ear height to base of top ear: 55.0 cm
Average length of top ear internode: 14.0 cm
Average number of tillers: 0
Average number of ears per stalk: 1.0
Anthocyanin of brace roots: Absent
Leaf:

Width of ear node leaf: 7.0 cm
Length of ear node leaf: 70.0 cm
Number of leaves above top ear: 6
Leaf angle (from 2nd leaf above ear at anthesis to stalk above leaf): 25°
Leaf color: 1-5GY4/4
Leaf sheath pubescence (Rated on scale from 1 = none to 9 = like peach fuzz): 4
Marginal waves (Rated on scale from 1 = none to 9 = many): 3
Longitudinal creases (Rated on scale from 1 = none to 9 = many): 2
Tassel:

Number of lateral branches: 8
Branch angle from central spike: 25°
Tassel length (from top leaf collar to tassel top): 43.0 cm
Pollen shed (Rated on scale from 0 = male sterile to 9 = heavy shed): 8
Anther color: 1-10Y8.5/8
Glume color: 1-5GY5/6
Tassel glume bands color: Absent
Ear (Unhusked Data):

Silk color (3 days after emergence): 1-10Y9/8
Fresh husk color (25 days after 50% silking): 1-5GY5/6
Dry husk color (65 days after 50% silking): 1-10Y9-4
Position of ear: Pendent
Husk tightness: 3
Husk extension at harvest: 2
Ear (Husked Ear Data):

Ear length: 17.0 cm
Ear diameter at mid-point: 40.3
Ear weight: 130 g
Number of kernel rows: 14-16
Row alignment: Straight
Shank length: 7 cm
Ear taper: Extreme
Kernel (Dried):

Kernel length: 10.0 mm
Kernel width: 7.3
Kernel thickness: 4.0
Hard endosperm color: 10-YR8/10
Endosperm type: Dent
Weight per 100 kernels (unsized sample): 21.0
Cob:

Cob diameter at mid-point: 19.6
Cob color: Dark Red
Agronomic Traits:

Dropped ears (at 65 days after anthesis):
Pre-anthesis brittle snapping:
Pre-anthesis root lodging:
Post-anthesis root lodging (at 65 days after anthesis):

TABLE 1K - BC137 VARIETY DESCRIPTION INFORMATION

General Plant Information:

Type: BC137 is a yellow, dent corn inbred
Region where developed: Kirkland, Illinois
Maturity:

| | Heat Units: |
|---|---|
| From planting to 50% of plants in silk: | 1549 |
| From planting to 50% of plants in pollen: | 1495 |

Plant:

Plant height to tassel tip: 201.7 cm
Ear height to base of top ear: 68.3 cm
Average length of top ear internode: 13.5 cm
Average number of tillers: 0
Average number of ears per stalk: 1.9
Anthocyanin of brace roots: Absent
Leaf:

Width of ear node leaf: 8.6 cm
Length of ear node leaf: 89.1 cm
Number of leaves above top ear: 5.4
Leaf angle (from 2nd leaf above ear at anthesis to stalk above leaf): 11.5°
Leaf color: Munsell 5GY4/4
Leaf sheath pubescence (Rated on scale from 1 = none to 9 = like peach fuzz): 1
Marginal waves (Rated on scale from 1 = none to 9 = many): 3
Longitudinal creases (Rated on scale from 1 = none to 9 = many): 2
Tassel:

Number of lateral branches: 6.8
Branch angle from central spike: 27.5°
Tassel length (from top leaf collar to tassel top): 46.8 cm
Pollen shed (Rated on scale from 0 = male sterile to 9 = heavy shed): 7
Anther color: Munsell 2.5GY8/6
Glume color: Munsell 5GY7/6
Tassel glume bands color: Absent
Ear (Unhusked Data):

Silk color (3 days after emergence): Munsell 2.5GY8/8
Fresh husk color (25 days after 50% silking): Munsell 5GY7/6
Dry husk color (65 days after 50% silking): Munsell 2.5Y8/8
Position of ear: Upright
Husk tightness (Rated on scale from 1 = very loose to 9 = very tight): 7
Husk extension at harvest: Short
Ear (Husked Ear Data):

Ear length: 14.4 cm
Ear diameter at mid-point: 44.8 cm
Ear weight: 140 g
Number of kernel rows: 16.0
Row alignment: Straight
Shank length: 11.8 cm
Ear taper: Average
Kernel (Dried):

Kernel length: 12.3 mm
Kernel width: 8.2 mm
Kernel thickness: 4.6 mm
Hard endosperm color: Munsell 2.5Y8/10
Endosperm type: Dent
Weight per 100 kernels (unsized sample): 33.3 g
Cob:

Cob diameter at mid-point: 22.2 mm
Cob color: Red Munsell 10R4/6
Agronomic Traits:

Dropped ears (at 65 days after anthesis): 0
Pre-anthesis brittle snapping: 0.0%
Pre-anthesis root lodging: 0.0%
Post-anthesis root lodging (at 65 days after anthesis): 0

TABLE 1L - CB20 VARIETY DESCRIPTION INFORMATION

General Plant Information:

Type: CB20 is a yellow, dent corn inbred
Region where developed: Lebanon, IN
Maturity: Zone 7

| | Heat Units: |
|---|---|
| From planting to 50% of plants in silk: | 1569.5 |
| From planting to 50% of plants in pollen: | 1569.5 |

Plant:

Plant height to tassel tip: 220.98 cm
Ear height to base of top ear: 72.39 cm
Average length of top ear internode: 12.7 cm
Average number of tillers: 0
Average number of ears per stalk: 2.0
Anthocyanin of brace roots: Absent
Leaf:

Width of ear node leaf: 8.89 cm
Length of ear node leaf: 78.74 cm
Number of leaves above top ear: 6
Leaf angle (from 2nd leaf above ear at anthesis to stalk above leaf): 35°
Leaf color: 2.5G 4/2
Leaf sheath pubescence (Rated on scale from 1 = none to 9 = like peach fuzz): 1
Marginal waves (Rated on scale from 1 = none to 9 = many): 3
Longitudinal creases (Rated on scale from 1 = none to 9 = many): 2
Tassel:

Number of lateral branches: 6
Branch angle from central spike: 10°
Tassel length (from top leaf collar to tassel top): 48 cm
Pollen shed (Rated on scale from 0 = male sterile to 9 = heavy shed): 4
Anther color: 5Y 8/12
Glume color: 2.5 GY 5/8
Tassel glume bands color: Absent
Ear (Unhusked Data):

Silk color (3 days after emergence): 2.5GY 8/10
Fresh husk color (25 days after 50% silking): 5GY 7/8
Dry husk color (65 days after 50% silking): 2.5Y 8/6
Position of ear: Pendent
Husk tightness: 7
Husk extension at harvest: 4 cm
Ear (Husked Ear Data):

Ear length: 12.5 cm
Ear diameter at mid-point: 40 mm
Ear weight: 96.9 g
Number of kernel rows: 14
Row alignment: Fairly Straight
Shank length: 11 cm
Ear taper: conico-cylindrical
Kernel (Dried):

Kernel length: 12 mm
Kernel width: N/A
Kernel thickness: 3 mm
Hard endosperm color: Grey
Endosperm type: Dent
Weight per 100 kernels (unsized sample): 30.6 g
Cob:

Cob diameter at mid-point: 25 mm
Cob color: N/A
Agronomic Traits:

Dropped ears (at 65 days after anthesis): N/A
Pre-anthesis brittle snapping: N/A
Pre-anthesis root lodging: N/A
Post-anthesis root lodging (at 65 days after anthesis): N/A -continued

TABLE 1M - MN26 VARIETY DESCRIPTION INFORMATION

General Plant Information:

Type: MN26 is a yellow, dent corn inbred
Region where developed: Kirkland, Illinois
Maturity:

| | Heat Units: |
|---|---|
| From planting to 50% of plants in silk: | 1409 |
| From planting to 50% of plants in pollen: | 1409 |

Plant:

Plant height to tassel tip: 244.9 cm
Ear height to base of top ear: 82.0 cm
Average length of top ear internode: 15.5 cm
Average number of tillers: 0
Average number of ears per stalk: 1.3
Anthocyanin of brace roots:
Leaf:

Width of ear node leaf: 10.1 cm
Length of ear node leaf: 98.0 cm
Number of leaves above top ear: 5.9
Leaf angle (from 2nd leaf above ear at anthesis to stalk above leaf): 13.8°
Leaf color: Munsell 5GY4/4
Leaf sheath pubescence (Rated on scale from 1 = none to 9 = like peach fuzz): 2
Marginal waves (Rated on scale from 1 = none to 9 = many): 6
Longitudinal creases (Rated on scale from 1 = none to 9 = many): 2
Tassel:

Number of lateral branches: 3.6
Branch angle from central spike: 25.3°
Tassel length (from top leaf collar to tassel top): 42.1 cm
Pollen shed (Rated on scale from 0 = male sterile to 9 = heavy shed): 6
Anther color: Munsell 5Y8/6
Glume color: Munsell 2.5GY7/6
Tassel glume bands color: Absent
Ear (Unhusked Data):

Silk color (3 days after emergence): Munsell 2.5GY8/8
Fresh husk color (25 days after 50% silking): Munsell 5GY6/8
Dry husk color (65 days after 50% silking):
Position of ear: Upright
Husk tightness (Rated on scale from 1 = very loose to 9 = very tight): 7
Husk extension at harvest: Medium
Ear (Husked Ear Data):

Ear length: 15.6 cm
Ear diameter at mid-point: 43.3 cm
Ear weight: 119 g
Number of kernel rows: 14.0
Row alignment: Straight
Shank length: 10.2 cm
Ear taper: Average
Kernel (Dried):

Kernel length: 10.7 mm
Kernel width: 8.5 mm
Kernel thickness: 5.0 mm
Hard endosperm color: Munsell 7.5YR6/10
Endosperm type: Dent
Weight per 100 kernels (unsized sample): 32.5 g
Cob:

Cob diameter at mid-point: 24.4 mm
Cob color: Red Munsell 5R6/8
Agronomic Traits:

Dropped ears (at 65 days after anthesis): 0
Pre-anthesis brittle snapping: 0.0%
Pre-anthesis root lodging: 0.0%
Post-anthesis root lodging (at 65 days after anthesis): 0%

Further Embodiments of the Invention

This invention is also directed to methods for producing a corn plant by crossing a first parent corn plant with a second parent corn plant wherein either the first or second parent corn plant is an inbred corn plant of inbred corn line BB202, AB8, AB18, AB19, BB84, BB85, BB95, BB98, BB201, BC106, BC137, CB20, or MN26. Further, both first and second parent corn plants can come from the inbred corn line BB202, AB8, AB18, AB19, BB84, BB85, BB95, BB98, BB201, BC106, BC137, CB20, or MN26. When self-pollinated, or crossed with another inbred corn line BB202, AB8, AB18, AB19, BB84, BB85, BB95, BB98, BB201, BC106, BC137, CB20, or MN26 plant, inbred corn line BB202, AB8, AB18, AB19, BB84, BB85, BB95, BB98, BB201, BC106, BC137, CB20, or MN26 will be stable while when crossed with another, different corn line, an $F_1$ hybrid seed is produced. Such methods of hybridization and self-pollination of corn are well known to those skilled in the art of corn breeding.

An inbred corn line has been produced through several cycles of self-pollination and is therefore to be considered as a homozygous line. An inbred line can also be produced though the dihaploid system which involves doubling the chromosomes from a haploid plant thus resulting in an inbred line that is genetically stable (homozygous) and can be reproduced without altering the inbred line. A hybrid variety is classically created through the fertilization of an ovule from an inbred parental line by the pollen of another, different inbred parental line. Due to the homozygous state of the inbred line, the produced gametes carry a copy of each parental chromosome. As both the ovule and the pollen bring a copy of the arrangement and organization of the genes present in the parental lines, the genome of each parental line is present in the resulting $F_1$ hybrid, theoretically in the arrangement and organization created by the plant breeder in the original parental line.

As long as the homozygosity of the parental lines is maintained, the resulting hybrid cross is stable. The $F_1$ hybrid is then a combination of phenotypic characteristics issued from two arrangement and organization of genes, both created by one skilled in the art through the breeding process.

Still further, this invention also is directed to methods for producing an inbred corn line BB202, AB8, AB18, AB19, BB84, BB85, BB95, BB98, BB201, BC106, BC137, CB20, or MN26-derived corn plant by crossing inbred corn line BB202, AB8, AB18, AB19, BB84, BB85, BB95, BB98, BB201, BC106, BC137, CB20, or MN26 with a second corn plant and growing the progeny seed, and repeating the crossing and growing steps with the inbred corn line BB202, AB8, AB18, AB19, BB84, BB85, BB95, BB98, BB201, BC106, BC137, CB20, or MN26-derived plant from 0 to 7 times. Thus, any such methods using the inbred corn line BB202, AB8, AB18, AB19, BB84, BB85, BB95, BB98, BB201, BC106, BC137, CB20, or MN26 are part of this invention: selfing, backcrosses, hybrid production, crosses to populations, and the like. All plants produced using inbred corn line BB202, AB8, AB18, AB19, BB84, BB85, BB95, BB98, BB201, BC106, BC137, CB20, or MN26 as a parent are within the scope of this invention, including plants derived from inbred corn line BB202, AB8, AB18, AB19, BB84, BB85, BB95, BB98, BB201, BC106, BC137, CB20, or MN26. Advantageously, the inbred corn line is used in crosses with other, different, corn inbreds to produce first generation ($F_1$) corn hybrid seeds and plants with superior characteristics.

It should be understood that the inbred can, through routine manipulation of cytoplasmic or other factors, be produced in a male-sterile form. Such embodiments are also contemplated within the scope of the present claims. As used herein, the term plant includes plant cells, plant protoplasts, plant cell tissue cultures from which corn plants can be regenerated, plant calli, plant clumps and plant cells that are intact in plants or parts of plants, such as embryos, pollen, ovules, flowers, kernels, seeds, ears, cobs, leaves, husks, stalks, roots, root tips, anthers, silk and the like.

Duncan, et al., (*Planta,* 1985, 165:322-332) indicates that 97% of the plants cultured that produced callus were capable of plant regeneration. Subsequent experiments with both inbreds and hybrids produced 91% regenerable callus that produced plants. In a further study in 1988, Songstad, et al. (*Plant Cell Reports,* 7:262-265) reports several media additions that enhance regenerability of callus of two inbred lines. Other published reports also indicated that "nontraditional" tissues are capable of producing somatic embryogenesis and plant regeneration. K. V. Rao et al., (*Maize Genetics Cooperation Newsletter,* 1986, 60:64-65) refer to somatic embryogenesis from glume callus cultures and B. V. Conger, et al. (*Plant Cell Reports,* 1987, 6:345-347) indicate somatic embryogenesis from the tissue cultures of corn leaf segments. Thus, it is clear from the literature that the state of the art is such that these methods of obtaining plants are routinely used and have a very high rate of success.

Tissue culture of corn is also described in European Patent Application, publication 160,390 and in Green and Rhodes, *Maize for Biological Research,* Plant Molecular Biology Association, Charlottesville, Va., 1982, 367-372. Thus, another aspect of this invention is to provide cells which upon growth and differentiation produce corn plants having the physiological and morphological characteristics of inbred corn line BB202, AB8, AB18, AB19, BB84, BB85, BB95, BB98, BB201, BC106, BC137, CB20, or MN26.

The utility of inbred corn line BB202, AB8, AB18, AB19, BB84, BB85, BB95, BB98, BB201, BC106, BC137, CB20, or MN26 also extends to crosses with other species. Commonly, suitable species will be of the family Graminaceae, and especially of the genera *Zea, Tripsacum, Coix, Schlerachne, Polytoca, Chionachne,* and *Trilobachne,* of the tribe *Maydeae.* Potentially suitable for crosses with BB202, AB8, AB18, AB19, BB84, BB85, BB95, BB98, BB201, BC106, BC137, CB20, or MN26 may be the various varieties of grain sorghum, *Sorghum bicolor* (L.) Moench.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Over the last fifteen to twenty years several methods for producing transgenic plants have been developed, and the present invention, in particular embodiments, also relates to transformed versions of the claimed inbred line. An embodiment of the present invention comprises at least one transformation event in inbred corn line BB202, AB8, AB18, AB19, BB84, BB85, BB95, BB98, BB201, BC106, BC137, CB20, or MN26.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed corn plants, using transformation methods as described below to incorporate transgenes into the genetic material of the corn plant(s).

Expression Vectors for Corn Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which, when placed under the control of plant regulatory signals, confers resistance to kanamycin (Fraley et al., *Proc. Natl. Acad. Sci. U.S.A.,* 80:4803 (1983)). Another commonly used selectable marker gene is the hygromycin phosphotransferase gene which confers resistance to the antibiotic hygromycin (Vanden Elzen et al., *Plant Mol. Biol.,* 5:299 (1985)).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant (Hayford et al., *Plant Physiol.* 86:1216 (1988), Jones et al., Mol. Gen. Genet., 210:86 (1987), Svab et al., *Plant Mol. Biol.* 14:197 (1990), and Hille et al., *Plant Mol. Biol.* 7:171 (1986)). Other selectable marker genes confer resistance to herbicides such as glyphosate, glufosinate or bromoxynil (Comai et al., *Nature* 317:741-744 (1985), Gordon-Kamm et al., *Plant Cell* 2:603-618 (1990) and Stalker et al., *Science* 242:419-423 (1988)).

Selectable marker genes for plant transformation that are not of bacterial origin include, for example, mouse dihydrofolate reductase, plant 5-enolpyruvylshikimate-3-phosphate synthase and plant acetolactate synthase (Eichholtz et al., *Somatic Cell Mol. Genet.* 13:67 (1987), Shah et al., *Science* 233:478 (1986), and Charest et al., *Plant Cell Rep.* 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS), beta-galactosidase, luciferase, and chloramphenicol acetyltransferase (Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), and DeBlock et al., *EMBO J.* 3:1681 (1984). Another approach to the identification of relatively rare transformation events has been use of a gene that encodes a dominant constitutive regulator of the *Zea mays* anthocyanin pigmentation pathway (Ludwig et al., *Science* 247:449 (1990)).

In vivo methods for visualizing GUS activity that do not require destruction of plant tissue are also available. However, these in vivo methods for visualizing GUS activity have not proven useful for recovery of transformed cells because of low sensitivity, high fluorescent backgrounds and limitations associated with the use of luciferase genes as selectable markers.

A gene encoding Green Fluorescent Protein (GFP) has been utilized as a marker for gene expression in prokaryotic and eukaryotic cells (Chalfie et al., *Science* 263:802 (1994)). GFP and mutants of GFP may be used as screenable markers.

Expression Vectors for Corn Transformation: Promoters

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain organs, such as leaves, roots, seeds and tissues such as fibers, xylem vessels, tracheids, or sclerenchyma. Such promoters are referred to as "tissue-preferred." Promoters which initiate transcription only in certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter which is active under most environmental conditions.

A. Inducible Promoters—An inducible promoter is operably linked to a gene for expression in corn. Optionally, the inducible promoter is operably linked to a nucleotide sequence encoding a signal sequence which is operably linked to a gene for expression in corn. With an inducible promoter the rate of transcription increases in response to an inducing agent. Any inducible promoter can be used in the instant invention. See Ward et al., *Plant Mol. Biol.* 22:361-366 (1993). Exemplary inducible promoters include, but are not limited to, that from the ACEI system which responds to copper (Mett et al., *Proc. Natl. Acad. Sci. U.S.A.* 90:4567-4571 (1993)); In2 gene from maize which responds to benzenesulfonamide herbicide safeners (Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B. Constitutive Promoters—A constitutive promoter is operably linked to a gene for expression in corn or the constitutive promoter is operably linked to a nucleotide sequence encoding a signal sequence which is operably linked to a gene for expression in corn. Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theon. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3):291-300 (1992)).

The ALS promoter, Xba1/Ncol fragment 5' to the *Brassica napus* ALS3 structural gene (or a nucleotide sequence similarity to said Xba1/Ncol fragment), represents a particularly useful constitutive promoter. See PCT application WO96/30530.

C. Tissue-specific or Tissue-preferred Promoters—A tissue-specific promoter is operably linked to a gene for expression in corn. Optionally, the tissue-specific promoter is operably linked to a nucleotide sequence encoding a signal sequence which is operably linked to a gene for expression in corn. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11):2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Knox, C., et al., *Plant Mol. Biol.* 9:3-17 (1987), Lerner et al., *Plant Physiol.* 91:124-129 (1989), Fontes et al., *Plant Cell* 3:483-496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., *Cell* 39:499-509 (1984), Stiefel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is corn. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology* CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defences are often activated by specific interaction between the product of a disease resistance gene (R) in the plant and the product of a corresponding avirulence (Avr) gene in the pathogen. A plant inbred line can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. *tomato* encodes a protein kinase); Mindrinos et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt alpha-endotoxin gene. Moreover, DNA molecules encoding alpha-endotoxin genes can be purchased from American Type Culture Collection, Manassas, Va., for example, under ATCC Accession Numbers 40098, 67136, 31995 and 31998.

C. A lectin. See, for example, the article by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US 93/06487. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* alpha-amylase inhibitor).

F. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper-accumulation of a monoterpene, a sesquiterpene, a steroid, a hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Numbers 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO 95/18855 (teaches synthetic antimicrobial peptides that confer disease resistance).

M. A membrane permease, a channel former or a channel blocker. For example, see the disclosure of Jaynes et al., *Plant Sci* 89:43 (1993), of heterologous expression of a cecropin-beta, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruseS. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect.

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo-alpha-1, 4-D-polygalacturonases facilitate fungal colonization and plant nutrient release by solubilising plant cell wall homoalpha-1, 4-D-galacturonase. See Lamb et al., *BioTechnology* 10:1436 (1992). The cloning and characterization of a gene which encodes a bean endopolygalacturonase-inhibiting protein is described by Toubart et al., *Plant J.* 2:367 (1992).

R. A developmental-arrestive protein produced in nature by a plant. For example, Logemann et al., *BioTechnology* 10:305 (1992), have shown that transgenic plants expressing the barley ribosome-inactivating gene have an increased resistance to fungal disease.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvylshikimate-3-phosphate synthase (EPSP) and aroA genes, respectively) and other phosphono compounds such as glufosinate (phosphinothricin acetyl transferase (PAT) and *Streptomyces hygroscopicus* (PAT bar genes), and pyridinoxy or phenoxy propionic acids and cyclohexones (ACCase inhibitor-encoding genes). See, for example, U.S. Pat. No. 4,940,835 to Shah et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *BioTechnology* 7:61 (1989), describe the production of transgenic plants that express chimeric bar genes coding for PAT activity. Exemplary of genes conferring resistance to phenoxy propionic acids and cyclohexones, such as sethoxydim and haloxyfop are the ABC5-S1, ABC5-S2 and ABC5-S3 genes described by Marshall et al., *Theor. Appl. Genet.* 83:435 (1992).

C. An herbicide that inhibits photosynthesis, such as a triazine (psbA and gs+ genes) or a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Numbers 53435, 67441, and 67442. Cloning and expression of DNA coding for a glutathione S-transferase is described by Hayes et al., *Biochem. J.* 285:173 (1992).

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knutzon et al., *Proc. Natl. Acad. Sci. U.S.A.* 89:2624 (1992)

B. Increased resistance to high light stress such as photooxidative damages, for example by transforming a plant with a gene coding for a protein of the Early Light Induced Protein family (ELIP) as described in WO 03/074713 in the name of Biogemma.

C. Modified carbohydrate composition effected, for example, by transforming plants with a gene coding for an enzyme that alters the branching pattern of starch. See Shiroza et al., *J. Bact.* 170:810 (1988) (nucleotide sequence of *Streptococcus* mutants fructosyltransferase gene), Steinmetz et al., *Mol. Gen. Genet.* 20:220 (1985) (nucleotide sequence of *Bacillus subtilis* levansucrase gene), Pen et al., *BioTechnology* 10:292 (1992) (production of transgenic plants that express *Bacillus licheniformis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley alpha-amylase gene), and Fisher et al., *Plant Physiol.* 102:1045 (1993) (maize endosperm starch branching enzyme II).

D. Increased resistance/tolerance to water stress or drought, for example, by transforming a plant to create a plant having a modified content in ABA-Water-Stress-Ripening-Induced proteins (ARS proteins) as described in WO 01/83753 in the name of Biogemma, or by transforming a plant with a nucleotide sequence coding for a phosphoenolpyruvate carboxylase as shown in WO 02/081714. The tolerance of corn to drought can also be increased by an overexpression of phosphoenolpyruvate carboxylase (PEPC-C4), obtained, for example from sorghum.

E. Increased content of cysteine and glutathione, useful in the regulation of sulfur compounds and plant resistance against various stresses such as drought, heat or cold, by transforming a plant with a gene coding for an Adenosine 5' Phosphosulfate as shown in WO 01/49855.

F. Increased nutritional quality, for example, by introducing a zein gene which genetic sequence has been modified so that its protein sequence has an increase in lysine and proline. The increased nutritional quality can also be attained by introducing into the maize plant an albumin 2S gene from sunflower that has been modified by the addition of the KDEL peptide sequence to keep and accumulate the albumin protein in the endoplasmic reticulum.

G. Decreased phytate content: 1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., *Maydica* 35:383 (1990).

4. Genes that Control Male Sterility

A. Introduction of a deacetylase gene under the control of a tapetum-specific promoter and with the application of the chemical N—Ac-PPT. See international publication WO 01/29237.

B. Introduction of various stamen-specific promoters. See international publications WO 92/13956 and WO 92/13957.

C. Introduction of the barnase and the barstar genes. See Paul et al., *Plant Mol. Biol.* 19:611-622, 1992).

Examples of Transgenes

MON810, also known as MON810Bt or BT1, is the designation given by the Monsanto Company (St. Louis, Mo.) for the transgenic event that, when expressed in maize, produces an endotoxin that is efficacious against the European corn borer, *Ostrinia nubilalis* and certain other Lepidopteran larvae.

MON603, also known as MON603RR2, better known as NK603, is the designation for the transgenic event that, when expressed in maize, allows the use of glyphosate as a weed control agent on the crop. Another transgenic event, GA21, when expressed in maize, also allows the use of glyphosate as a weed control agent on the crop.

MON89034, a designation given by the Monsanto Company (St. Louis, Mo.) for the transgenic event that, when expressed in maize, produces an endotoxin that is efficacious against the European corn borer, *Ostrinia nubilalis*, fall armyworm, *Spodoptera frugiperda*, and certain other Lepidopteran larvae.

MON88017, also known as MON88017CCR1, is the transgenic event that, when expressed in maize, allows the use of glyphosate as a weed control agent. In addition, this event produces an endotoxin that is efficacious against the corn root worm, *Diabrotica virgifera*, and certain other Coleopteran larvae.

HERCULEX Corn Borer, better known as HX1 or TC1507, is the designation for the transgenic event that, when expressed in maize, produces an endotoxin that is efficacious against the European corn borer, *Ostrinia nubilalis*, and certain other Lepidopteran larvae. In addition, the transgenic event was developed to allow the crop to be tolerant to the use of glufosinate ammonium, the active ingredient in phosphinothricin herbicides.

HERCULEX Root Worm, or DAS59122-7, is the designation for the transgenic event that, when expressed in maize, produces an endotoxin that is efficacious against the corn root worm, *Diabrotica virgifera*, and certain other Coleopteran larvae. In addition, the transgenic event was developed to allow the crop to be tolerant to the use of glufosinate ammonium, the active ingredient in phosphinothricin herbicides.

T25 is the designation for the transgenic event that, when expressed in maize, allows the crop to be tolerant to the use of glufosinate ammonium, the active ingredient in phosphinothricin herbicides.

Methods for Corn Transformation

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer—Despite the fact the host range for *Agrobacterium*-mediated transformation is broad, some major cereal crop species and gymnosperms have generally been recalcitrant to this mode of gene transfer, even though some success has recently been achieved in rice and corn. Hiei et al., *The Plant Journal* 6:271-282 (1994) and U.S. Pat. No. 5,591,616 issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 micron. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *BioTechnology* 6:559-563 (1988), Sanford, J. C., *Physiol Plant* 7:206 (1990), Klein et al., *BioTechnology* 10:268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., *BioTechnology* 9:996 (1991). Alternatively, liposome and spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. D'Halluin et al., *Plant Cell* 4:1495-1505 (1992) and Spencer et al., *Plant Mol. Biol.* 24:51-61 (1994).

Following transformation of corn target tissues, expression of the above-described selectable marker genes allows for preferential selection of transformed cells, tissues and/or plants, using regeneration and selection methods now well known in the art.

The foregoing methods for transformation would typically be used for producing a transgenic inbred line. The transgenic inbred line could then be crossed, with another (non-transformed or transformed) inbred line, in order to produce a new transgenic inbred line. Alternatively, a genetic trait which has been engineered into a particular corn line using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term inbred corn plant is used in the context of the present invention, this also includes any inbred corn plant where one or more desired traits have been introduced through backcrossing methods, whether such trait is a naturally occurring one or a transgenic one. Backcrossing methods can be used with the present invention to improve or introduce one or more characteristic into the inbred. The term backcrossing as used herein refers to the repeated crossing of a hybrid progeny back to one of the parental corn plants for that inbred. The parental corn plant which contributes the gene or the genes for the desired characteristic is termed the nonrecurrent or donor parent. This terminology refers to the fact that the nonrecurrent parent is used one time in the backcross protocol and therefore does not recur. The parental corn plant to which the gene or genes from the nonrecurrent parent are transferred is known as the recurrent parent as it is used for several rounds in the backcrossing protocol (Fehr, 1987).

In a typical backcross protocol, the original inbred of interest (recurrent parent) is crossed to a second inbred (nonrecurrent parent) that carries the gene or genes of interest to be transferred. The resulting progeny from this cross are then crossed again to the recurrent parent and the process is repeated until a corn plant is obtained wherein all the desired morphological and physiological characteristics of the recurrent parent are recovered in the converted plant in addition to the gene or genes transferred from the nonrecurrent parent. It should be noted that some, one, two, three or more, self-pollination and growing of a population might be included between two successive backcrosses. Indeed, an appropriate selection in the population produced by the self-pollination, i.e., selection for the desired trait and physiological and morphological characteristics of the recurrent parent might be equivalent to one, two or even three additional backcrosses in a continuous series without rigorous selection, saving time, money and effort for the breeder. The backcross process could also be accelerated through a step of haploid induction together by a molecular marker screening to identify the backcross progeny plants that have the closest genetic resemblance with the recurrent line, together with the gene or genes of interest to be transferred. A non limiting example of such a protocol would be the following: a) the first generation $F_1$ produced by the cross of the recurrent parent A by the donor parent B is backcrossed to parent A, b) selection is practiced for the plants having the desired trait of parent B, c) selected plants are self-pollinated to produce a population of plants where selection is practiced for the plants having the desired trait of parent B and the physiological and morphological characteristics of parent A, d) the selected plants are backcrossed one, two, three, four, five or more times to parent A to produce selected backcross progeny plants comprising the desired trait of parent B and the physiological and morphological characteristics of parent A. Step c) may or may not be repeated and included between the backcrosses of step d. Step c) may or may not be followed by a step of haploid induction followed by molecular marker screening.

The selection of a suitable recurrent parent is an important step for a successful backcrossing procedure. The goal of a backcross protocol is to alter or substitute one or more trait(s) or characteristic(s) in the original inbred. To accomplish this, a gene or genes of the recurrent inbred is modified or substituted with the desired gene or genes from the nonrecurrent parent, while retaining essentially all of the rest of the desired genetic, and therefore the desired physiological and morphological, constitution of the original inbred. The choice of the particular nonrecurrent parent will depend on the purpose of the backcross; one of the major purposes is to add some commercially desirable, agronomically important trait(s) to the plant. The exact backcrossing protocol will depend on the characteristic(s) or trait(s) being altered to determine an appropriate testing protocol. Although backcrossing methods are simplified when the characteristic being transferred is a single gene and dominant allele, multiple genes and recessive allele(s) may also be transferred and therefore, backcross breeding is by no means restricted to character(s) governed by one or a few genes. In fact the number of genes might be less important than the identification of the character(s) in the segregating population. In this instance it may then be necessary to introduce a test of the progeny to determine if the desired characteristic(s) has been successfully transferred. Such tests encompass not only visual inspection and simple crossing, but also follow up of the characteristic(s) through genetically associated markers and molecular assisted breeding tools. For example, selection of progeny containing the transferred trait is done by direct selection, visual inspection for a trait associated with a dominant allele, while the selection of progeny for a trait that is transferred via a recessive allele, such as the waxy starch characteristic, require selfing the progeny to determine which plant carry the recessive allele(s).

Many single gene traits have been identified that are not regularly selected for in the development of a new inbred but that can be improved by backcrossing techniques. Single gene traits may or may not be transgenic, i.e., they may be naturally present in the nonrecurrent parent, examples of these traits include but are not limited to, male sterility, waxy starch, amylose starch, herbicide resistance, resistance for bacterial, fungal, or viral disease, insect resistance, male fertility, water stress tolerance, enhanced nutritional quality, industrial usage, increased digestibility, yield stability and yield enhancement. An example of this is the Rp1D gene which controls resistance to rust fungus by preventing *P. sorghi* from producing spores. The Rp1D gene is usually preferred over the other Rp genes because it is widely effective against all races of rust, but the emergence of new races has lead to the use of other Rp genes comprising, for example, the Rp1E, Rp1G, Rp1I, Rp1K or "compound" genes which combine two or more Rp genes including Rp1GI, Rp1GDJ, etc. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference. Genes related to digestibility are known to one skilled in the art, such as those described in U.S. Pat. Nos. 8,20,302, 8,143,482 and 8,088,95. Each of the references mentioned above is herein incorporated into reference by its entirety.

In 1981, the backcross method of breeding accounted for 17% of the total breeding effort for inbred line development in the United States, according to, Hallauer, A. R. et al., (1988) "Corn Breeding" in *Corn and Corn Improvement*, No. 18, pp. 463-481. The backcross breeding method provides a precise way of improving varieties that excel in a large number of attributes but are deficient in a few characteristics (Allard, 1960, *Principles of Plant Breeding*, John Wiley & Sons, Inc.). The method makes use of a series of backcrosses to the variety to be improved during which the character or the characters in which improvement is sought is maintained by selection. At the end of the backcrossing, the gene or genes being transferred unlike all other genes will be heterozygous. Selfing after the last backcross produces homozygosity for this gene pair(s) and, coupled with selection, will result in a variety with exactly the adaptation, yielding ability and quality characteristics of the recurrent parent but superior to that parent in the particular characteristic(s) for which the improvement program was undertaken. Therefore, this method provides the plant breeder with a high degree of genetic control of his work.

Backcrossing is a powerful mechanism for achieving homozygosity and any population obtained by backcrossing may rapidly converge on the genotype of the recurrent parent. When backcrossing is made the basis of a plant breeding program, the genotype of the recurrent parent will be modified with regards to genes being transferred, which are maintained in the population by selection.

Examples of successful backcrosses are the transfer of stem rust resistance from "Hope" wheat to "Bart" wheat and the transfer of bunt resistance to "Bart" wheat to create "Bart 38" which has resistance to both stem rust and bunt. Also highlighted by Allard is the successful transfer of mildew, leaf spot and wilt resistances in "California Common" alfalfa to create "Caliverde." This new "Caliverde" variety produced through the backcross process is indistinguishable from "California Common" except for its resistance to the three named diseases.

One of the advantages of the backcross method is that the breeding program can be carried out in almost every environment that will allow the development of the character being transferred. Another advantage of the backcross method is that more than one character or trait can be transferred, either through several backcrosses or through the use of transformation and then backcrossing.

The backcross technique is not only desirable when breeding for disease resistance but also for the adjustment of morphological characters, color characteristics and simply inherited quantitative characters such as earliness, plant height and seed size and shape. In this regard, a medium grain type variety, "Calady," has been produced by Jones and Davis. In dealing with quantitative characteristics, they selected the donor parent with the view of sacrificing some of the intensity of the character for which it was chosen, i.e., grain size. "Lady Wright," a long grain variety was used as the donor parent and "Coloro," a short grain one as the recurrent parent. After four backcrosses, the medium grain type variety "Calady" was produced.

DEPOSIT INFORMATION

A deposit of the inbred corn line of this invention is maintained by AgReliant Genetics, LLC, 4640 East SR32, Lebanon, Ind. 46052. AgReliant maintains the seed deposit on behalf of Limagrain Europe and KWS SART AG. In addition, a sample of the inbred corn seed of this invention has been or will be deposited with the American Type Culture Collection, 10801 University Boulevard, Manassas, Va. 20110 or the National Collections of Industrial, Food and Marine Bacteria (NCIMB), 23 St Machar Drive, Aberdeen, Scotland, AB24 3RY, United Kingdom.

To satisfy the enablement requirements of 35 U.S.C. 112, and to certify that the deposit of the isolated strain (i.e., corn inbred) of the present invention meets the criteria set forth in 37 CFR 1.801-1.809 and Manual of Patent Examining Procedure (MPEP) 2402-2411.05, Applicants hereby make the following statements regarding the deposited corn inbred line BC106 (deposited as ATCC Accession No. 124009):

If the deposit is made under the terms of the Budapest Treaty, the instant invention will be irrevocably and without restriction released to the public upon the granting of a patent.

If the deposit is made not under the terms of the Budapest Treaty, Applicant(s) provides assurance of compliance by following statements:

1. During the pendency of this application, access to the invention will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 CFR 1.807; and
5. The deposit will be replaced if it should ever become unavailable.

Access to this deposit will be available during the pendency of this application to persons determined by the Commissioner of Patents and Trademarks to be entitled thereto under 37 C.F.R. §1.14 and 35 U.S.C. §122. Upon granting of any claims in this application, all restrictions on the availability to the public of the variety will be irrevocably removed by affording access to a deposit of at least 2,500 seeds of the same variety with the ATCC or NCIMB.

INDUSTRIAL APPLICABILITY

Corn is used as human food, livestock feed, and as raw material in industry. The food uses of corn, in addition to human consumption of corn kernels, include both products of dry- and wet-milling industries. The principal products of corn dry-milling are grits, meal and flour. Corn meal is flour ground to fine, medium, and coarse consistencies from dried corn. In the United States, the finely ground corn meal is also referred to as corn flour. However, the term "corn flour" denotes corn starch in the United Kingdom. Corn meal has a long shelf life and is used to produce an assortment of products, including but not limited to tortillas, taco shells, bread, cereal and muffins.

The corn wet-milling industry can provide corn starch, corn syrups, corn sweeteners and dextrose for food use. Corn syrup is used in foods to soften texture, add volume, prevent crystallization of sugar and enhance flavor. Corn syrup is distinct from high-fructose corn syrup (HFCS), which is created when corn syrup undergoes enzymatic processing, producing a sweeter compound that contains higher levels of fructose.

Corn oil is recovered from corn germ, which is a by-product of both dry- and wet-milling industries. Corn oil which is high in mono and poly unsaturated fats, is used for reducing fat and trans fat in numerous food products.

Corn, including both grain and non-grain portions of the plant, is also used extensively as livestock feed, primarily for beef cattle, dairy cattle, hogs and poultry.

Industrial uses of corn include production of ethanol, corn starch in the wet-milling industry and corn flour in the dry-milling industry. Corn ethanol is ethanol produced from corn as a biomass through industrial fermentation, chemical processing and distillation. Corn is the main feedstock used for producing ethanol fuel in the United States. The industrial applications of corn starch and flour are based on functional properties, such as viscosity, film formation, adhesive properties, and ability to suspend particles. Corn starch and flour also have application in the paper and textile industries. Other industrial uses include applications in adhesives, building materials, foundry binders, laundry starches, explosives, oil-well muds and other mining applications.

Plant parts other than the grain of corn are also used in industry, for example, stalks and husks are made into paper and wallboard and cobs are used for fuel and to make charcoal.

The seed of inbred corn line BB202, AB8, AB18, AB19, BB84, BB85, BB95, BB98, BB201, BC106, BC137, CB20, or MN26, the plant produced from the inbred seed, the hybrid corn plant produced from the crossing of the inbred, hybrid seed, and various parts of the hybrid corn plant and transgenic versions of the foregoing, can be utilized for human food, livestock feed, and as a raw material in industry.

Tables of Field Test Trials

In the tables that follow, exemplary traits and characteristics of hybrid combinations having inbred corn line BB202, AB8, AB18, AB19, BB84, BB85, BB95, BB98, BB201, BC106, BC137, CB20, or MN26 as a parental line are given compared to other hybrids. The data collected are presented for key characteristics and traits. The field tests are experimental trials and have been made at numerous locations, with one or two replications per location under supervision of the applicant. Information about these experimental hybrids as compared to the check hybrids is presented.

Information for each pedigree includes:
1. Mean yield of the hybrid across all locations (bushels/acre) is shown in column 2.
2. A mean for the percentage moisture (H20 Grain) for the hybrid across all locations is shown in column 3.
3. A mean of the yield divided by the percentage moisture (Y/M) for the hybrid across all locations is shown in column 4.
4. A mean of the percentage of plants with stalk lodging (SL %) across all locations is shown in column 5.
5. A mean of the percentage of plants with root lodging (RL %) across all locations is shown in column 6.
6. Test weight (TW) is the grain density as measured in pounds per bushel and is shown in column 7.
7. Harvest Appearance (Asp) is a rating made by a trained person on the date of harvest. Harvest appearance is the rater's impression of the hybrid based on, but not limited to, a combination of factors to include plant intactness, tissue health appearance and ease of harvest as it relates to stalk lodging and root lodging. A scale of 1=Lowest to 9=Highest/Most Desirable is used and is listed in column 8.
8. Plant Height (PlHt) is a physical measurement taken from the ground level to the tip of the tassel. It is expressed to the nearest tenth of an inch and is shown in column 9.
9. Ear Height (EHt) is a physical measurement taken from the ground level to the node of attachment for the upper ear. It is expressed to the nearest tenth of an inch and is shown in column 10.

BB202 Field Test Trials (Tables 2A to 10A)

TABLE 2A

Overall Comparisons: First year field trials, 4 locations

| Hybrid | YLD | H2O | Y/M | SL % | RL % | TW | Asp | PlHt | EHt |
|---|---|---|---|---|---|---|---|---|---|
| BB202/MN5 | 189.4 | 22.2 | 8.5 | 5.7 | 2.8 | 55.0 | 4.4 | 9.7 | 3.0 |
| CB1/MN5 | 186.0 | 26.3 | 7.1 | 1.6 | 10.3 | 53.7 | 4.4 | 9.5 | 3.1 |
| BB14/LH287BT1CCR1 | 170.6 | 23.7 | 7.2 | 5.4 | 28.8 | 54.7 | 4.6 | | |
| BB14/MN5 | 164.2 | 24.9 | 6.6 | 3.2 | 1.0 | 54.3 | 4.9 | 8.7 | 2.8 |

TABLE 3A

Overall comparisons: Second year field trials, 9 locations

| Hybrid | YLD | H2O | Y/M | SL % | RL % | TW | Asp | PlHt | EHt |
|---|---|---|---|---|---|---|---|---|---|
| BB202/LH287BT1CCR1 | 205.3 | 28.3 | 7.2 | 1.7 | 1.5 | 51.7 | 5.9 | 9.8 | 3.6 |
| BB202/MM27BT1 | 201.9 | 27.7 | 7.3 | 0.7 | 0.8 | 52.3 | 6.3 | 9.8 | 3.6 |
| Controls | 197.2 | 28.8 | 6.8 | 1.8 | 1.4 | 51.9 | 5.9 | 9.8 | 3.7 |
| BB46/MM27BT1 | 198.2 | 29.2 | 6.8 | 2.9 | 2.2 | 52.1 | 5.8 | 10.2 | 3.9 |
| RBO1CCR1/LH287BT1-1 | 195.9 | 28.0 | 7.0 | 1.6 | 1.5 | 52.0 | 5.9 | 9.4 | 3.6 |
| BB59/LH287BT1CCR1 | 197.4 | 29.3 | 6.7 | 0.8 | 0.7 | 51.7 | 6.1 | 9.7 | 3.4 |

TABLE 4A

Overall Comparisons: Third year field trials, 10 locations

| Hybrid | YLD | H2O | Y/M | SL % | RL % | TW | Asp | PlHt | EHt |
|---|---|---|---|---|---|---|---|---|---|
| BB59/LH287RR2-1 | 198.5 | 20.7 | 9.6 | 0.5 | 1.1 | 54.6 | 6.8 | 9.2 | 3.1 |
| BB202/ML12 | 194.2 | 19.7 | 9.9 | 1.9 | 0.6 | 55.5 | 6.1 | 9.5 | 3.9 |
| HCL301RR2/HCL516 | 184.3 | 19.9 | 9.3 | 1.1 | 0.0 | 55.1 | 6.5 | 9.0 | 3.1 |
| HCL112RR2/HCL437 | 172.6 | 16.9 | 10.2 | 0.7 | 0.1 | 56.6 | 5.3 | 8.9 | 3.1 |

TABLE 5A

Overall Comparisons: Third year field trials, 6 locations

| Hybrid | YLD | H2O | Y/M | SL % | RL % | TW | Asp | PlHt | EHt |
|---|---|---|---|---|---|---|---|---|---|
| BB202/LH287BT1CCR1 | 205.6 | 19.1 | 10.7 | 0.8 | 0.9 | 54.1 | 5.2 | 9.5 | 3.3 |
| BB36/MN7CCR1 | 189.3 | 18.5 | 10.2 | 0.2 | 0.8 | 54.1 | 4.6 | 8.9 | 2.6 |
| DKC63-84 | 196.2 | 20.1 | 9.8 | 0.8 | 1.1 | 53.7 | 6.0 | 9.0 | 3.3 |
| BB38/LH287BT1CCR1 | 188.8 | 20.0 | 9.4 | 0.6 | 0.0 | 53.6 | 5.2 | 8.5 | 3.0 |
| BB38/MN7CCR1 | 180.2 | 18.3 | 9.8 | 0.2 | 0.7 | 55.2 | 5.0 | | |

TABLE 6A

Overall Comparisons: Fourth year field trials, 28 locations

| Hybrid | YLD | H2O | Y/M | SL % | RL % | TW | Asp | PlHt | EHt |
|---|---|---|---|---|---|---|---|---|---|
| BB202/ML12 | 190.4 | 20.2 | 9.4 | 0.8 | 5.3 | 56.8 | 5.4 | 9.4 | 3.8 |
| BB59/LH287BT1CCR1 | 192.9 | 22.7 | 8.5 | 0.6 | 1.8 | 55.8 | 6.2 | 9.0 | 3.3 |
| BB38/ML9 | 185.3 | 20.3 | 9.1 | 1.2 | 1.8 | 56.6 | 5.7 | 8.8 | 3.3 |
| BB59/LH287RR2-1 | 185.5 | 21.6 | 8.6 | 1.1 | 4.5 | 56.2 | 5.8 | 8.9 | 3.4 |
| DKC57-50 | 184.4 | 21.1 | 8.7 | 1.3 | 1.1 | 56.7 | 5.7 | 9.0 | 3.4 |
| R6258RMQKZ/ML8 | 181.2 | 20.3 | 8.9 | 1.1 | 1.5 | 56.2 | 5.7 | 9.3 | 4.0 |
| HCL301RR2/HCL516BT1 | 175.9 | 20.3 | 8.7 | 1.4 | 3.6 | 57.0 | 5.1 | 8.7 | 3.3 |

TABLE 7A

Overall Comparisons: Fourth year field trials, 23 locations

| Hybrid | YLD | H2O | Y/M | SL % | RL % | TW | Asp | PlHt | EHt |
|---|---|---|---|---|---|---|---|---|---|
| BB202/LH287BT1CCR1 | 191.8 | 21.2 | 9.1 | 1.8 | 3.1 | 56.6 | 5.4 | 9.6 | 3.4 |
| DKC57-50 | 189.8 | 20.6 | 9.2 | 0.5 | 1.2 | 57.1 | 5.6 | 9.3 | 3.5 |
| BB59/LH287BT1CCR1 | 191.1 | 22.4 | 8.5 | 1.5 | 2.8 | 55.8 | 5.8 | 9.2 | 3.2 |
| R6258RMQKZ/ML8 | 182.1 | 20.4 | 8.9 | 0.8 | 0.9 | 56.4 | 6.0 | 9.4 | 3.9 |
| RBO1CCR1/LH287BT1-1 | 180.7 | 21.8 | 8.3 | 0.5 | 1.9 | 56.8 | 5.5 | 9.4 | 3.3 |
| HCL301CCR1/HCL516BT1 | 169.4 | 19.7 | 8.6 | 4.5 | 2.4 | 57.5 | 4.6 | 8.9 | 3.4 |

TABLE 8A

Overall Comparisons: Fifth year field trials, 47 locations

| Hybrid | YLD | H2O | Y/M | SL % | RL % | TW | Asp | PlHt | Eht |
|---|---|---|---|---|---|---|---|---|---|
| BB202/A1555RMQKZ | 179.6 | 18.7 | 9.6 | 4.1 | 0.6 | 57.1 | | | |
| CB18/MN7RMQKZ | 179.3 | 17.5 | 10.3 | 2.3 | 0.3 | 55.6 | | | |
| BB38RMQKD/MM53 | 177.4 | 16.8 | 10.6 | 1.6 | 0.5 | 58.5 | | | |
| BB59/A1555RMQKZ | 178.4 | 18.8 | 9.5 | 0.4 | 0.9 | 56.1 | | | |
| DKC57-50 | 177.0 | 17.8 | 10.0 | 0.4 | 0.4 | 58.3 | | | |
| BB59/A1555RMQKZ | 177.8 | 19.1 | 9.3 | 0.5 | 1.8 | 56.1 | | | |
| BB59/A1555RMQKZ | 176.4 | 19.0 | 9.3 | 0.8 | 0.9 | 56.2 | | | |
| P1018AM1 | 172.2 | 18.2 | 9.5 | 1.2 | 0.8 | 58.0 | | | |

TABLE 9A

Overall Comparisons: Fifth year field trials, 23 locations

| Hybrid | YLD | H2O | Y/M | SL % | RL % | TW | Asp | PlHt | EHt |
|---|---|---|---|---|---|---|---|---|---|
| BB202/ML12 | 182.5 | 19.2 | 9.5 | 0.2 | 0.7 | 54.4 | 5.8 | 9.6 | 3.6 |
| P1018AM1 | 182.0 | 20.1 | 9.1 | 0.6 | 7.9 | 54.4 | 6.3 | 9.6 | 3.6 |
| BB59/A1555RMQKZ | 181.6 | 19.5 | 9.3 | 0.6 | 1.9 | 54.2 | 6.3 | 9.2 | 3.1 |
| BB59/LH287RR2-1 | 180.8 | 18.4 | 9.8 | 2.5 | 0.8 | 55.1 | 6.1 | 9.0 | 3.1 |
| DKC57-50 | 179.8 | 18.2 | 9.9 | 0.7 | 0.5 | 57.3 | 5.6 | 9.3 | 3.4 |
| BB38RMQKZ/MM53 | 176.5 | 17.1 | 10.3 | 1.8 | 0.5 | 57.3 | 5.7 | 9.4 | 3.4 |
| CB18/MN7RMQKZ | 172.8 | 17.6 | 9.8 | 2.1 | 0.7 | 56.4 | 5.1 | 9.1 | 3.3 |
| F4780RMQKZ × T5972Z | 172.1 | 16.7 | 10.3 | 2.4 | 0.4 | 59.2 | 5.3 | 9.3 | 3.1 |
| BB38/ML9 | 171.8 | 17.1 | 10.0 | 0.5 | 0.1 | 57.4 | 5.8 | 8.9 | 3.0 |

TABLE 10A

Overall Comparisons: Fifth year field trials, 14 locations

| Hybrid | YLD | H2O | Y/M | SL % | RL % | TW | Asp | PlHt | EHt |
|---|---|---|---|---|---|---|---|---|---|
| BB202/MN29 | 186.7 | 18.2 | 10.3 | 0.1 | 0.6 | 55.6 | 5.6 | 9.4 | 3.5 |
| BB38RMQKZ/MM53 | 184.2 | 18.1 | 10.2 | 0.0 | 1.1 | 57.0 | 5.8 | 10.0 | 3.6 |
| BB38/ML9 | 182.4 | 17.7 | 10.3 | 0.0 | 0.0 | 56.8 | 6.0 | 9.4 | 3.2 |
| CB18/MN7RMQKZ | 182.8 | 19.1 | 9.6 | 0.0 | −0.1 | 55.3 | 5.5 | 9.2 | 3.4 |
| BB59/LH287RR2-1 | 180.9 | 19.5 | 9.3 | 0.0 | 1.4 | 53.9 | 6.1 | 9.2 | 3.2 |
| BB38RMQKZ/ML9 | 178.4 | 17.3 | 10.3 | 0.2 | 0.6 | 58.2 | 5.6 | 9.3 | 3.3 |
| BB59/A1555RMQKZ | 180.1 | 21.5 | 8.4 | 0.0 | 0.0 | 53.9 | 6.5 | 9.3 | 3.1 |
| DKC57-50 | 178.5 | 19.6 | 9.1 | 0.1 | −0.1 | 56.6 | 5.7 | 9.2 | 3.4 |
| F4780RMQKZ × T5972Z | 174.5 | 17.9 | 9.8 | 0.5 | 1.1 | 58.5 | 5.4 | 9.8 | 3.7 |
| P1018AM1 | 172.5 | 20.7 | 8.3 | 0.0 | 4.1 | 55.4 | 6.1 | 10.0 | 4.1 |

AB8 Field Test Trials (Tables 2B to 9B)

TABLE 2B

Overall comparisons: Year 1 field trials, 15 reps

| Pedigree | Yld Grain | H2O | Y/M | SL % | RL % | TW | EHt | PlHt | LD | SG | Asp |
|---|---|---|---|---|---|---|---|---|---|---|---|
| P39B94 | 144.6 | 23.5 | 6.2 | 2.0 | 6.7 | 51.6 | 117.9 | 267.7 | 5.0 | 5.0 | 5.6 |
| DKC33-11 | 140.9 | 23.9 | 5.9 | 2.9 | 0.2 | 51.4 | 107.4 | 256.7 | 6.0 | 5.0 | 5.6 |
| AB8/IV2 | 143.7 | 25.0 | 5.8 | 1.0 | 2.6 | 50.6 | 98.9 | 263.7 | 7.0 | 4.0 | 5.4 |
| AB8/IV2BT1RR2 | 145.3 | 25.0 | 5.8 | 1.3 | 0.6 | 51.1 | 94.9 | 252.7 | 7.0 | 4.0 | 6.1 |
| AB7CCR1/IV2BT1 | 140.3 | 25.5 | 5.5 | 0.8 | 0.8 | 50.4 | 88.9 | 245.7 | 7.0 | 4.0 | 5.3 |
| AB7/IV2BT1 | 134.2 | 26.1 | 5.1 | 0.3 | 1.7 | 50.9 | 86.9 | 249.7 | 7.0 | 4.0 | 5.4 |
| AB7/IV2 | 134.5 | 26.2 | 5.1 | 1.5 | 2.5 | 50.3 | 85.9 | 251.7 | 7.0 | 4.0 | 4.9 |
| AB7/1V2BT1RR2 | 145.9 | 26.4 | 5.5 | 0.3 | 1.5 | 51.0 | 85.9 | 250.2 | 8.0 | 5.0 | 5.3 |

TABLE 3B

Overall Comparisons: Year 1 Field Trials/31 reps

| Pedigree | Yld Grain | H2O | Y/M | SL % | RL % | TW | EHt | PlHt | LD | SG | Asp |
|---|---|---|---|---|---|---|---|---|---|---|---|
| DKC33-11 | 139.8 | 22.8 | 6.1 | 0.9 | 0.1 | 51.5 | 111.0 | 249.8 | 6.0 | 5.0 | 5.6 |
| P39B94 | 137.8 | 22.8 | 6.0 | 1.7 | 4.6 | 52.2 | 121.0 | 265.3 | 4.0 | 3.0 | 5.4 |
| AB8/IV2BT1 | 144.4 | 23.6 | 6.1 | 1.6 | 2.6 | 50.2 | 104.0 | 262.8 | 6.0 | 4.0 | 5.6 |
| AB8/IV2BT1RR2 | 141.2 | 24.5 | 5.8 | 0.4 | 1.6 | 50.0 | 102.0 | 257.8 | 7.0 | 4.0 | 5.9 |
| DKC26-79 | 122.1 | 24.6 | 5.0 | 7.2 | 10.5 | 51.3 | 102.9 | 234.1 | 2.0 | 2.0 | 3.8 |
| AB8/IV2RR2 | 141.0 | 24.6 | 5.7 | 0.8 | 1.4 | 50.3 | 109.0 | 268.8 | 7.0 | 4.0 | 5.5 |
| AB7/IV2BT1 | 142.2 | 24.9 | 5.7 | 0.4 | 1.4 | 50.3 | 97.0 | 252.8 | 7.0 | 5.0 | 5.1 |
| AB7/IV2BT1RR2 | 139.6 | 25.0 | 5.6 | 0.6 | 0.8 | 50.5 | 96.0 | 245.8 | 7.0 | 5.0 | 5.2 |
| AB7CCR1/IV2BT1 | 133.4 | 25.1 | 5.3 | 0.5 | 2.5 | 50.1 | 92.0 | 252.3 | 7.0 | 5.0 | 5.3 |
| AB7/IV2RR2 | 140.5 | 26.5 | 5.3 | 0.8 | 1.3 | 50.2 | 92.0 | 249.8 | 7.0 | 4.0 | 5.2 |

TABLE 4B

Overall Comparisons: Year 2 Field Trials/22 reps

| Pedigree | Yld Grain | H2O | Y/M | SL % | RL % | TW | EHt | PlHt | LD | SG | Asp |
|---|---|---|---|---|---|---|---|---|---|---|---|
| P39D97 | 142.3 | 17.8 | 8.0 | 5.3 | 4.5 | 59.8 | 115.5 | 268.0 | 5.8 | 3.3 | 5.7 |
| AB8RBDHV & IV2BT1 | 152.7 | 17.8 | 8.6 | 3.9 | 0.9 | 57.9 | 106.0 | 280.5 | 5.8 | 3.9 | 6.3 |
| AB8 × IV2BT1RR2 | 147.9 | 18.0 | 8.2 | 5.1 | 1.3 | 57.6 | 109.0 | 276.0 | 5.3 | 2.8 | 6.3 |
| DKC30-20 | 141.8 | 18.1 | 7.8 | 0.5 | 0.8 | 58.9 | 104.1 | 273.0 | 6.8 | 5.1 | 6.7 |
| DKC26-79 | 124.6 | 18.2 | 6.8 | 2.1 | 7.3 | 59.6 | 92.5 | 236.5 | 4.2 | 2.6 | 5.7 |
| P39B94 | 130.9 | 18.7 | 7.0 | 2.3 | 4.3 | 59.4 | 127.0 | 281.5 | 5.8 | 5.0 | 6.5 |

TABLE 5B

Overall Comparisons: Year 2 Field Trials/33 reps

| Pedigree | Yld Grain | H2O | Y/M | SL % | RL % | TW | EHt | PlHt | LD | SG | Asp |
|---|---|---|---|---|---|---|---|---|---|---|---|
| DKC35-43 | 165.7 | 17.4 | 9.5 | 4.5 | 0.1 | 58.4 | 101.2 | 267.4 | 7.0 | 6.2 | 6.3 |
| N23K-3000GT | 171.8 | 18.1 | 9.5 | 1.9 | 2.8 | 56.5 | 93.1 | 264.3 | 5.0 | 5.4 | 6.1 |
| P8906HR | 175.1 | 18.5 | 9.5 | 0.9 | 2.1 | 56.3 | 113.6 | 291.2 | 5.0 | 6.2 | 6.4 |
| P38B14 | 168.2 | 19.1 | 8.8 | 0.9 | 1.9 | 56.0 | 124.9 | 269.3 | 6.0 | 6.8 | 6.6 |
| AB8/NP2623CBLL | 180.6 | 19.3 | 9.4 | 2.9 | 0.8 | 54.6 | 117.4 | 281.2 | 6.0 | 6.3 | 6.6 |
| DKC38-89 | 180.4 | 19.9 | 9.1 | 2.6 | 1.2 | 55.0 | 96.2 | 269.3 | 6.7 | 5.5 | 6.1 |

TABLE 6B

Overall Comparisons: Year 2 Field Trials/46 replications

| Pedigree | Yld Grain | H2O | Y/M | SL % | RL % | GS % | TW | EHt | PlHt | LD | SG | Asp |
|---|---|---|---|---|---|---|---|---|---|---|---|---|
| AB7CCR1 × 7625 | 175.7 | 15.5 | 11.3 | 2.6 | 3.0 | 0.0 | 57.1 | 100.7 | 270.5 | 5.0 | 3.5 | 4.9 |
| AB7 × 7625 | 181.6 | 16.6 | 11.0 | 1.8 | 1.0 | 0.0 | 55.9 | 96.2 | 270.2 | 5.7 | 5.8 | 5.2 |
| DKC43-27 | 178.0 | 16.7 | 10.7 | 1.3 | 0.0 | 0.0 | 56.8 | 98.5 | 253.2 | 7.0 | 6.0 | 5.6 |
| P38N88 | 180.3 | 16.9 | 10.7 | 0.1 | 1.7 | 0.0 | 57.1 | 113.7 | 270.0 | 6.3 | 5.8 | 5.6 |
| AB7CCR1 × 7627 | 175.7 | 17.0 | 10.3 | 1.3 | 2.7 | 0.0 | 56.4 | 99.2 | 265.5 | 5.0 | 6.2 | 5.3 |
| AB8RBDHV × 7625 | 187.9 | 17.3 | 10.9 | 1.1 | 1.4 | 0.0 | 55.9 | 110.0 | 286.7 | 6.7 | 5.2 | 6.0 |
| AB8RBDHV × 7627 | 186.6 | 17.5 | 10.7 | 1.5 | 0.4 | 0.0 | 56.3 | 109.6 | 271.4 | 6.0 | 5.2 | 6.2 |
| AB8 × 7625 | 185.7 | 18.3 | 10.1 | 3.7 | 3.7 | 0.0 | 55.1 | 114.0 | 287.5 | 6.3 | 6.7 | 5.9 |
| AB8 × 7627 | 188.1 | 18.4 | 10.2 | 2.2 | 2.0 | 0.0 | 55.8 | 113.0 | 275.7 | 6.0 | 5.8 | 6.2 |
| P37Y14 | 184.0 | 19.0 | 9.7 | 1.1 | 1.3 | 0.0 | 56.1 | 114.7 | 282.7 | 6.7 | 7.0 | 6.2 |
| DKC50-44 | 192.7 | 19.5 | 9.9 | 2.8 | 0.7 | 0.3 | 55.5 | 108.9 | 273.0 | 6.7 | 5.7 | 5.7 |

TABLE 7B

Overall Comparisons: Year 3 Field Trials/22 locations

| Pedigree | Yld Grain | H2O | Y/M | SL % | RL % | GS % | TW | EHt | PlHt | LD | SG | Asp |
|---|---|---|---|---|---|---|---|---|---|---|---|---|
| DKC42-72 | 170.9 | 18.9 | 9.0 | 1.2 | 0.5 | 4.1 | 55.3 | 101.1 | 246.7 | 7.0 | 8.0 | 5.8 |
| AB8RBDHV/II11 | 162.9 | 19.0 | 8.6 | 1.9 | 1.2 | 1.8 | 54.5 | 105.6 | 258.9 | 5.5 | 7.5 | 5.7 |
| P9494AM1 | 167.2 | 19.4 | 8.6 | 0.8 | 1.7 | 2.8 | 53.8 | 111.1 | 252.2 | 6.5 | 7.5 | 5.4 |
| AB8RBDHV/II11 | 161.5 | 19.7 | 8.2 | 2.4 | 0.1 | 2.0 | 54.0 | 110.0 | 257.8 | 6.0 | 6.5 | 5.8 |
| AB8/II11 | 156.1 | 19.8 | 7.9 | 3.1 | 2.0 | 2.5 | 54.1 | 110.6 | 257.8 | 4.0 | 7.5 | 5.6 |

TABLE 8B

Overall Comparisons: Year 4 Field Trials/18 locations

| Pedigree | Yld Grain | H2O | Y/M | SL % | RL % | TW | EHt | PlHt | LD | Asp |
|---|---|---|---|---|---|---|---|---|---|---|
| HCL116RR2/F7298ZNYKZ | 175.9 | 16.7 | 10.5 | 2.9 | 2.3 | 57.4 | 103.3 | 247.5 | 5.0 | 5.6 |
| HC50RR2-1/HCL422 | 167.2 | 17.1 | 9.8 | 5.4 | 0.1 | 56.7 | 106.7 | 265.9 | 5.0 | 5.8 |
| HC50BT1CCR1/HCL422 | 176.7 | 17.3 | 10.2 | 4.3 | 2.2 | 57.4 | 105.8 | 252.5 | 5.5 | 6.2 |
| T0813Z/F1513RMQKZ | 176.6 | 17.4 | 10.1 | 7.7 | 1.3 | 57.9 | 115.8 | 273.4 | 6.5 | 6.3 |
| HCL116RR2/F3632ZNYKZ | 187.6 | 17.5 | 10.7 | 7.9 | 3.0 | 57.6 | 114.5 | 258.8 | 6.5 | 5.5 |
| AB8RBDHV/7719 | 191.0 | 17.6 | 10.8 | 5.6 | 4.2 | 55.7 | 119.2 | 275.0 | 5.5 | 5.6 |
| T9305RHTTZ/A7195ZNYKZ | 179.0 | 17.6 | 10.1 | 5.7 | 1.5 | 57.4 | 104.2 | 260.0 | 6.5 | 5.9 |
| P8906HR | 186.0 | 17.8 | 10.5 | 4.4 | 1.8 | 57.1 | 101.7 | 251.7 | 5.5 | 5.8 |
| HCL116CCR1/HCL419BT1-2 | 196.7 | 18.4 | 10.7 | 3.1 | 4.5 | 58.1 | 117.5 | 272.5 | 6.5 | 6.3 |
| SGI028RBDHZ/SGI069ZKDDZ | 173.0 | 18.5 | 9.3 | 4.9 | 4.0 | 56.5 | 110.0 | 253.4 | 5.5 | 5.5 |
| DKC38-89 | 183.2 | 18.6 | 9.8 | 6.4 | 1.2 | 57.4 | 94.2 | 249.2 | 6.0 | 6.1 |

TABLE 9B

Overall Comparisons: Year 4 Field Trials/15 locations

| Pedigree | Yld Grain | H2O | Y/M | SL % | RL % | TW | Asp |
|---|---|---|---|---|---|---|---|
| AB8RBDHV/7719 | 193.7 | 17.8 | 10.9 | 3.0 | 0.9 | 55.4 | 5.3 |
| DKC39-07 | 185.8 | 17.8 | 10.4 | 1.5 | 2.8 | 56.7 | 4.9 |
| P8906AM1 | 180.9 | 17.9 | 10.1 | 0.7 | 4.5 | 55.9 | 4.7 |
| A8668RMQKZ/T0813Z | 183.4 | 18.3 | 10.0 | 0.8 | 0.2 | 56.8 | 5.2 |
| AB8/7719 | 200.8 | 18.4 | 10.9 | 1.1 | 0.2 | 54.5 | 5.7 |
| HCL116CCR1/HCL419BT1 | 180.9 | 19.0 | 9.5 | 0.1 | 1.4 | 58.0 | 4.8 |

AB18 Field Test Trials (Tables 2C to 10C)

TABLE 2C

Overall comparisons: Year 1 field trials, 8 reps

| Pedigree | Yld Grain | H2O | Y/M | SL % | RL % | TW | LD | Asp |
|---|---|---|---|---|---|---|---|---|
| HC50RR2-1 & SGI928 | 179.9 | 24.4 | 7.4 | 2.7 | 6.4 | 52.2 | 7.0 | 5.7 |
| HCL116RR2 × HCL419 | 194.2 | 25.4 | 7.7 | 1.6 | 1.6 | 51.7 | 3.0 | 6.4 |
| DKC43-27 | 184.7 | 26.4 | 7.0 | 0.3 | 0.2 | 51.4 | 7.0 | 5.7 |
| HCL116CCR1 × HCL529BT1 | 192.3 | 26.4 | 7.3 | 0.3 | 0.1 | 51.4 | 5.0 | 6.1 |
| HCL107CCR1 × HCL506BT1 | 175.4 | 27.0 | 6.5 | 1.0 | 0.1 | 51.2 | 7.0 | 6.7 |
| AB18 & NP2623CBLL | 188.8 | 27.9 | 6.8 | 0.2 | 1.9 | 51.1 | 3.0 | 6.0 |

TABLE 3C

Overall comparisons: Year 2 field trials, 11 reps

| Pedigree | Yld Grain | H2O | Y/M | SL % | RL % | TW | EHt | PlHt | LD | SG | Asp |
|---|---|---|---|---|---|---|---|---|---|---|---|
| HC50RR2-2 & SGI901 | 157.1 | 16.4 | 9.6 | 7.2 | 2.5 | 58.0 | 111.6 | 286.9 | 5.0 | 5.0 | 5.6 |
| AB18 × IV2BT1 | 167.6 | 16.6 | 10.1 | 1.5 | 9.5 | 58.2 | 96.6 | 269.9 | 4.0 | 3.2 | 5.3 |
| HC50BT1CCR1 × HCL422 | 167.1 | 17.4 | 9.6 | 1.9 | 2.5 | 56.5 | 104.6 | 273.9 | 7.0 | 5.0 | 6.2 |
| HCL116RR2 × HCL419 | 182.9 | 17.9 | 10.2 | 4.2 | 1.1 | 56.4 | 113.6 | 288.9 | 6.0 | 6.0 | 6.3 |
| P38B14 | 163.4 | 18.7 | 8.7 | 2.3 | 7.6 | 55.9 | 123.6 | 272.9 | 6.0 | 7.2 | 5.9 |
| HCL116CCR1 × HCL419BT1-2 | 186.4 | 19.1 | 9.7 | 1.9 | 2.9 | 55.7 | 109.6 | 286.9 | 8.0 | 7.2 | 6.3 |

TABLE 4C

Overall comparisons: Year 2 field trials, 13 reps

| Pedigree | Yld Grain | H2O | Y/M | SL % | RL % | TW | EHt | PlHt | LD | SG | Asp |
|---|---|---|---|---|---|---|---|---|---|---|---|
| DKC50-44 | 168.7 | 16.6 | 10.2 | 1.0 | 0.7 | 56.9 | 94.2 | 260.5 | 6.0 | 5.5 | 5.8 |
| AB18/ML9 | 183.2 | 17.4 | 10.5 | 4.3 | 4.2 | 55.2 | 108.7 | 287.2 | 5.0 | 5.5 | 6.1 |
| P37Y14 | 181.8 | 18.8 | 9.7 | 0.9 | 1.0 | 56.0 | 110.3 | 276.0 | 8.0 | 8.0 | 6.5 |
| HCL105CCR1/HCL530BT1 | 179.3 | 19.7 | 9.1 | 1.3 | 3.5 | 55.0 | 113.1 | 272.2 | 7.0 | 6.5 | 6.1 |

TABLE 5C

Overall comparisons: Year 3 field trials, 17 reps

| Pedigree | Yld Grain | H2O | Y/M | SL % | RL % | GS % | TW | EHt | PlHt | LD | SG | Asp |
|---|---|---|---|---|---|---|---|---|---|---|---|---|
| DKC30-20 | 122.3 | 19.7 | 6.2 | 1.5 | 0.5 | 7.1 | 57.2 | 92.5 | 242.6 | 6.7 | 5.0 | 5.1 |
| P8107HR | 133.1 | 20.1 | 6.6 | 3.6 | 1.5 | 0.0 | 55.8 | 105.5 | 237.6 | 5.7 | 5.5 | 4.8 |
| DKC35-43 | 130.1 | 20.2 | 6.4 | 3.2 | 0.1 | 2.8 | 56.7 | 108.4 | 257.4 | 7.3 | 7.0 | 5.8 |
| P39D97 | 135.2 | 20.3 | 6.7 | 2.0 | 14.4 | 4.6 | 56.9 | 102.5 | 241.5 | 4.7 | 5.0 | 4.9 |
| DKC26-79 | 108.9 | 21.0 | 5.2 | 14.8 | 5.4 | 2.1 | 56.4 | 82.5 | 209.0 | 4.0 | 3.0 | 3.3 |
| AB18/IV2BT1RR2 | 141.9 | 21.1 | 6.7 | 4.8 | 1.8 | 0.0 | 55.5 | 90.9 | 244.0 | 4.7 | 4.0 | 5.3 |
| DKC38-89 | 144.3 | 22.2 | 6.5 | 0.7 | 0.1 | 0.0 | 54.6 | 84.5 | 243.6 | 7.7 | 7.0 | 5.3 |

TABLE 6C

Overall comparisons: Year 3 field trials, 14 reps

| Pedigree | Yld Grain | H2O | Y/M | SL % | RL % | GS % | TW | EHt | PlHt | LD | Asp |
|---|---|---|---|---|---|---|---|---|---|---|---|
| HCL116RR2 × HCL419 | 163.7 | 20.0 | 8.2 | 13.4 | 0.6 | 2.7 | 56.9 | 112.4 | 270.6 | 7.3 | 5.2 |
| HCL116CCR1 × HCL419BT1-2 | 159.5 | 20.6 | 7.8 | 4.1 | 0.1 | 3.2 | 56.6 | 100.8 | 253.9 | 6.3 | 6.1 |
| AB18 & TR2678CBLL | 156.0 | 20.3 | 7.7 | 7.4 | 0.7 | 3.1 | 56.1 | 96.6 | 248.1 | 6.7 | 5.2 |
| DKC38-89 | 154.0 | 20.7 | 7.4 | 4.0 | 0.0 | 0.0 | 55.8 | 84.9 | 251.4 | 6.3 | 5.3 |
| P8906HR | 155.1 | 21.0 | 7.4 | 5.4 | 0.3 | 1.7 | 56.7 | 101.3 | 259.3 | 6.3 | 5.7 |
| DKC35-43 | 142.3 | 19.7 | 7.2 | 5.8 | 0.5 | 0.0 | 57.1 | 100.8 | 235.6 | 7.3 | 5.5 |

TABLE 7C

Overall comparisons: Year 3 field trials, 22 reps

| Pedigree | Yld Grain | H2O | Y/M | SL % | RL % | GS % | TW | EHt | PlHt | LD | SG | Asp |
|---|---|---|---|---|---|---|---|---|---|---|---|---|
| DKC42-72 | 169.8 | 19.1 | 8.9 | 0.8 | 0.1 | 9.0 | 54.8 | 108.9 | 248.6 | 7.0 | 8.0 | 6.1 |
| HCL116CCR1/HCL419BT1-2 | 169.5 | 19.3 | 8.8 | 3.3 | 7.2 | 15.7 | 55.4 | 107.8 | 260.2 | 7.5 | 7.5 | 5.2 |
| AB18/NP2623GTCBLL | 167.8 | 20.0 | 8.4 | 3.9 | 0.9 | 2.3 | 53.9 | 115.0 | 259.7 | 7.0 | 7.5 | 5.7 |
| P9494AM1 | 166.0 | 19.0 | 8.8 | 1.0 | 1.9 | 0.3 | 53.4 | 107.2 | 249.7 | 7.0 | 7.5 | 5.4 |
| HCL116CCR1/HCL529BT1 | 158.3 | 19.1 | 8.3 | 0.4 | 3.6 | 10.3 | 55.3 | 108.3 | 253.6 | 6.5 | 6.5 | 5.1 |

TABLE 8C

Overall comparisons: Year 3 field trials, 22 reps

| Pedigree | Yld Grain | H2O | Y/M | SL % | RL % | GS % | TW | EHt | PlHt | LD | SG | Asp |
|---|---|---|---|---|---|---|---|---|---|---|---|---|
| HC50RR2-1/HCL422 | 151.4 | 17.6 | 8.6 | 2.3 | 2.8 | 9.5 | 55.1 | 108.3 | 261.7 | 6.5 | 4.5 | 4.9 |
| HCL116RR2/HCL529 | 155.4 | 18.7 | 8.3 | 2.3 | 1.0 | 17.3 | 55.6 | 108.3 | 262.2 | 6.0 | 6.5 | 4.7 |
| HCL116RR2/HCL419 | 157.2 | 18.9 | 8.3 | 4.2 | 1.6 | 15.2 | 54.9 | 112.8 | 267.2 | 6.0 | 7.5 | 5.1 |
| DKC42-72 | 170.9 | 18.9 | 9.0 | 1.2 | 0.5 | 4.1 | 55.3 | 101.1 | 246.7 | 7.0 | 8.0 | 5.8 |

TABLE 8C-continued

Overall comparisons: Year 3 field trials, 22 reps

| Pedigree | Yld Grain | H2O | Y/M | SL % | RL % | GS % | TW | EHt | PlHt | LD | SG | Asp |
|---|---|---|---|---|---|---|---|---|---|---|---|---|
| P9494AM1 | 167.2 | 19.4 | 8.6 | 0.8 | 1.7 | 2.8 | 53.8 | 111.1 | 252.2 | 6.5 | 7.5 | 5.4 |
| HCL107RR2/HCL506 | 161.7 | 19.5 | 8.3 | 2.1 | 0.9 | 9.9 | 54.4 | 108.3 | 250.6 | 7.5 | 6.5 | 5.5 |
| HCL112RR2/HCL437 | 164.7 | 20.3 | 8.1 | 2.0 | 0.0 | 11.9 | 55.0 | 103.3 | 256.7 | 7.0 | 8.5 | 5.6 |
| AB18/II11 | 158.5 | 20.3 | 7.8 | 2.5 | 1.2 | 0.5 | 54.8 | 106.7 | 252.8 | 5.5 | 7.5 | 5.4 |
| AB18/ML9 | 172.9 | 21.6 | 8.0 | 3.0 | 5.0 | 0.6 | 53.3 | 115.6 | 276.7 | 5.5 | 7.5 | 5.6 |

TABLE 9C

Overall comparisons: Year 4 field trials, 19 reps

| Pedigree | Yld Grain | H2O | Y/M | SL % | RL % | TW | EHt | PlHt | LD | Asp |
|---|---|---|---|---|---|---|---|---|---|---|
| AB7/7719 | 197.1 | 17.3 | 11.4 | 6.2 | 0.5 | 57.1 | 100.8 | 267.5 | 5.5 | 5.6 |
| HCL116RR2/F3632ZNYKZ | 188.9 | 17.4 | 10.9 | 7.5 | 2.8 | 57.9 | 114.5 | 258.8 | 6.5 | 5.5 |
| AB8RBDHV/7719 | 191.4 | 17.5 | 10.9 | 5.4 | 4.4 | 56.1 | 119.2 | 275.0 | 5.5 | 5.6 |
| P8906HR | 186.3 | 17.7 | 10.6 | 4.2 | 1.9 | 57.4 | 101.7 | 251.7 | 5.5 | 5.8 |
| AB18/7719 | 195.6 | 18.0 | 10.9 | 4.5 | 2.3 | 57.0 | 123.3 | 277.5 | 6.0 | 5.8 |
| HCL116CCR1/HCL419BT1-2 | 197.6 | 18.2 | 10.8 | 3.0 | 4.2 | 58.4 | 117.5 | 272.5 | 6.5 | 6.4 |
| DKC38-89 | 184.7 | 18.5 | 10.0 | 6.1 | 1.1 | 57.7 | 94.2 | 249.2 | 6.0 | 6.1 |

TABLE 10C

Overall comparisons: Year 4 field trials, 48 reps

| Pedigree | Yld Grain | H2O | Y/M | SL % | RL % | TW | Asp | PlHt | EHt | LD |
|---|---|---|---|---|---|---|---|---|---|---|
| HCL116CCR1/HCL419BT1-2 | 193.0 | 17.6 | 11.0 | 1.4 | 1.2 | 59.5 | 5.8 | 270.3 | 115.0 | 5.0 |
| DKC43-27 | 189.1 | 17.7 | 10.7 | 0.3 | 0.8 | 58.6 | 5.8 | 253.6 | 101.3 | 7.0 |
| DKC42-72 | 195.3 | 17.9 | 10.9 | 0.2 | 0.9 | 58.5 | 6.1 | 254.9 | 109.2 | 7.0 |
| R2999RMQKB/A3974Z | 191.7 | 17.9 | 10.7 | 0.1 | 0.8 | 58.1 | 5.7 | 254.9 | 112.1 | 4.0 |
| P9519HR | 194.6 | 17.9 | 10.8 | 0.2 | 3.2 | 57.6 | 5.7 | 264.4 | 118.8 | 5.0 |
| HCL107CCR1/HCL506BT1 | 192.6 | 17.9 | 10.7 | 0.3 | 0.5 | 58.6 | 6.1 | 244.9 | 102.5 | 6.0 |
| AB18/7623 | 200.0 | 18.5 | 10.8 | 0.5 | 4.8 | 57.4 | 5.6 | 256.9 | 111.3 | 5.0 |
| A0241RPGJZ/HCL439 | 199.5 | 18.6 | 10.7 | 0.6 | 1.2 | 57.7 | 5.6 | 266.9 | 112.1 | 5.0 |
| HCL112RR2/A5338ZNYKZ | 193.9 | 18.9 | 10.3 | 0.3 | 0.0 | 58.1 | 6.1 | 252.8 | 112.5 | 5.0 |
| R2999RBDHZ/HCL4003BT1 | 197.8 | 18.9 | 10.4 | 0.2 | 0.4 | 57.2 | 6.4 | 267.4 | 112.5 | 5.0 |
| HCL112RR2/HCL437 | 198.1 | 19.2 | 10.3 | 0.8 | 0.6 | 57.5 | 6.5 | 259.1 | 113.1 | 8.0 |
| A0241RMQKZ/R5207LMSLZ | 199.2 | 19.8 | 10.1 | 0.4 | 1.1 | 55.6 | 6.3 | 268.4 | 112.1 | 5.0 |

AB19 Field Test Trials (Tables 2D to 7D)

TABLE 2D

Overall comparisons: First Year field trials, 11 reps
UM2307 11 Locations, 11 Reps

| Hybrid | Yield Bu/Ac | H2O Grain | Y/M | SL % | RL % | TW | Har Ap | PlHt | EHt |
|---|---|---|---|---|---|---|---|---|---|
| HCL116CCR1/HCL425BT1 | 167.1 | 25.1 | 6.7 | 0.0 | 0.0 | 53.0 | 5.3 | 98.4 | — |
| HC50BT1CCR1/HCL422 | 173.3 | 26.4 | 6.6 | 0.1 | 0.0 | 52.6 | 5.5 | 102.4 | — |
| HCL116CCR1/HCL419BT1-2 | 180.8 | 26.7 | 6.8 | 0.1 | 0.0 | 52.3 | 6.1 | 102.4 | — |
| HCL116CCR1/HCL529BT1 | 179.1 | 27.1 | 6.6 | 2.0 | 0.0 | 52.4 | 5.5 | 105.3 | — |
| HCL107CCR1/HCL506BT1 | 170.7 | 28.4 | 6.0 | 0.5 | 0.0 | 52.4 | 6.1 | 97.4 | — |
| NP2623CBLL/AB19 | 179.2 | 29.4 | 6.1 | 0.1 | 0.0 | 51.7 | 5.5 | 101.4 | — |
| HCL105CCR1/HCL530BT1 | 185.3 | 31.7 | 5.9 | 0.5 | 0.5 | 51.1 | 6.2 | 104.3 | — |
| HCL107CCR1/HCL407BT1 | 177.2 | 32.9 | 5.4 | 0.7 | 0.0 | 51.4 | 6.6 | 96.5 | — |

TABLE 3D

Overall comparisons: Second Year field trials, 15 reps
UM3303 15 Locations, 15 Reps

| Hybrid | Yield Bu/Ac | H2O Grain | Y/M | SL % | RL % | TW | Har Ap | PlHt | EHt |
|---|---|---|---|---|---|---|---|---|---|
| AB7CCR1/7457 | 173.4 | 14.8 | 11.7 | 3.9 | 1.5 | 58.2 | 5.3 | 108.5 | 39.9 |
| HCL116CCR1/HCL425BT1 | 162.6 | 15.3 | 10.7 | 2.7 | 0.0 | 59.4 | 4.6 | 93.5 | 36.4 |
| HC50BT1CCR1/HCL422 | 169.6 | 15.5 | 11.0 | 0.9 | 0.0 | 58.6 | 6.4 | 106.8 | 40.4 |
| HCL116RR2/HCL419 | 171.7 | 16.0 | 10.8 | 3.2 | 0.1 | 58.3 | 5.9 | 108.5 | 43.6 |
| DKC43-27 | 181.4 | 16.4 | 11.1 | 0.4 | 0.0 | 57.6 | 6.3 | 98.7 | 37.9 |
| HCL116CCR1/HCL529BT1 | 173.8 | 16.6 | 10.5 | 1.9 | 0.0 | 58.3 | 6.3 | 106.5 | 42.1 |
| HCL116CCR1/HCL419BT1-2 | 188.1 | 17.0 | 11.1 | 1.3 | 0.0 | 57.5 | 6.5 | 106.8 | 40.4 |
| AB7CCR1/7261 | 178.7 | 17.0 | 10.5 | 2.2 | 2.4 | 56.8 | 5.8 | 104.1 | 42.1 |
| NP2623GTCBLL/AB19 | 187.9 | 17.3 | 10.9 | 0.5 | 1.3 | 56.0 | 6.5 | 102.1 | 40.4 |
| HCL112CCR1/HCL437BT1 | 185.5 | 17.6 | 10.6 | 2.2 | 0.1 | 57.1 | 6.7 | 107.8 | 44.0 |
| HCL107CCR1/HCL407BT1 | 190.3 | 18.4 | 10.3 | 1.3 | 1.3 | 55.9 | 6.9 | 101.1 | 42.8 |
| R5207LFWMZ/A0241GJLHZ | 184.9 | 19.8 | 9.3 | 2.5 | 1.2 | 55.5 | 6.7 | 108.8 | 45.0 |
| T2142RBDHZ/HCL519BT1 | 188.8 | 20.3 | 9.3 | 1.7 | 0.4 | 55.5 | 6.9 | 103.3 | 42.3 |

TABLE 4D

Overall comparisons: Third Year field trials, 17 reps
UK4101 15 Locations, 17 Reps

| Hybrid | Yield Bu/Ac | H2O Grain | Y/M | SL % | RL % | TW | Har Ap | PlHt | EHt | GS % |
|---|---|---|---|---|---|---|---|---|---|---|
| LM3/IV2BT1RR2 | 113.5 | 19.6 | 5.8 | 1.5 | 2.2 | 56.3 | 5.1 | 90.2 | 34.1 | 3.6 |
| DKC30-20 | 122.3 | 19.7 | 6.2 | 1.5 | 0.5 | 57.2 | 5.1 | 94.9 | 36.6 | 7.1 |
| P8107HR | 133.1 | 20.1 | 6.6 | 3.6 | 1.5 | 55.8 | 4.8 | 92.9 | 41.7 | 0.0 |
| DKC35-43 | 130.1 | 20.2 | 6.4 | 3.2 | 0.1 | 56.7 | 5.8 | 101.4 | 42.7 | 2.8 |
| HC37RR2-1/SGI901 | 129.1 | 20.2 | 6.4 | 1.7 | 0.1 | 56.8 | 5.5 | 103.0 | 41.7 | 1.9 |
| P39D97 | 135.2 | 20.3 | 6.7 | 2.0 | 14.4 | 56.9 | 5.0 | 95.1 | 40.4 | 4.6 |
| (TR2040RR2 & TR3026RR2) & TR1914 | 130.7 | 20.3 | 6.4 | 2.9 | 5.9 | 56.7 | 4.8 | 92.2 | 36.4 | 1.2 |
| R5927RBDHZ × F3745ZKDDZ | 127.8 | 20.3 | 6.3 | 0.8 | 0.2 | 57.7 | 5.7 | 92.8 | 35.1 | 4.2 |
| A9587RBDHZ × A2268ZNYKZ | 135.3 | 20.5 | 6.6 | 0.4 | 0.9 | 56.2 | 6.0 | 94.8 | 37.7 | 0.2 |
| HCL116CCR1/HCL425BT1 | 138.6 | 20.8 | 6.6 | 1.9 | 0.1 | 56.7 | 5.2 | 94.2 | 33.8 | 1.5 |
| DKC26-79 | 108.9 | 21.0 | 5.2 | 14.8 | 5.4 | 56.4 | 3.3 | 82.3 | 32.5 | 2.1 |
| TR2097RR2/TR1957BT1 | 97.4 | 21.1 | 4.6 | 21.8 | 0.1 | 56.2 | 3.3 | 87.6 | 35.4 | 3.2 |
| IV2RR2/AB19 | 137.3 | 21.2 | 6.5 | 2.3 | 5.5 | 54.6 | 5.4 | 94.5 | 34.8 | 2.9 |
| DKC38-89 | 144.3 | 22.2 | 6.5 | 0.7 | 0.1 | 54.6 | 5.3 | 95.3 | 33.5 | 0.0 |

TABLE 5D

Overall comparisons: Fourth Year field trials, 6 reps
NET 1 U.S. 6 Locations, 6 Reps

| Hybrid | Yield Bu/Ac | H2O Grain | Y/M | SL % | RL % | TW | Har Ap | PlHt | EHt |
|---|---|---|---|---|---|---|---|---|---|
| LM3/IV2BT1RR2 | 121.9 | 13.2 | 9.2 | 10.0 | | 59.2 | | | |
| P39D97 | 137.9 | 13.8 | 10.0 | 15.0 | | 59.3 | | | |
| DKC30-20 | 125.8 | 13.9 | 9.0 | 15.0 | | 58.2 | | | |
| A9587RHTTZ × A2268ZNYKZ | 141.0 | 14.2 | 9.9 | 5.0 | | 57.1 | | | |
| IV2BT1RR2/AB19 | 139.6 | 14.3 | 9.8 | 0.0 | | 56.4 | | | |
| R5927RBDHZ × A3498ZKDDZ | 141.1 | 14.3 | 9.9 | 5.0 | | 58.3 | | | |
| SGI044RHTTZ/SGI045ZNYKZ | 128.2 | 14.4 | 8.9 | 5.0 | | 58.2 | | | |
| R5927RBDHZ × A3498ZKDDZ | 134.1 | 14.4 | 9.3 | 5.0 | | 57.2 | | | |
| R5927RBDHZ × A3498ZKDDZ | 144.2 | 14.6 | 9.9 | 5.0 | | 57.7 | | | |
| HCL116RR2/F7298ZNYKZ | 143.4 | 14.7 | 9.8 | 5.0 | | 56.2 | | | |
| R4168RMQKZ/R5407Z | 135.5 | 14.8 | 9.2 | 5.0 | | 58.6 | | | |

TABLE 6D

Overall comparisons: Fourth Year field trials, 14 reps
UK5101 West Only 7 Locations, 14 Reps

| Hybrid | Yield Bu/Ac | H2O Grain | Y/M | SL % | RL % | TW | Har Ap | PlHt | EHt |
|---|---|---|---|---|---|---|---|---|---|
| IV2BT1RR2/AB19 | 160.3 | 14.1 | 11.3 | 0.4 | 3.2 | 60.2 | 4.7 | 106.0 | 45.0 |
| LM3/IV2BT1RR2 | 140.7 | 14.3 | 9.8 | 4.5 | 3.0 | 62.6 | 3.3 | 99.8 | 39.5 |
| R5927RBDHZ/A3498ZKDDZ | 166.9 | 14.3 | 11.7 | 2.7 | 0.8 | 61.4 | 4.5 | 103.4 | 46.6 |
| A9587RHTTZ × A2268ZNYKZ | 160.8 | 14.4 | 11.2 | 2.3 | 0.6 | 61.3 | 4.5 | 102.4 | 44.8 |
| SGI044RHTTZ/SGI045ZNYKZ | 152.7 | 14.4 | 10.6 | 1.6 | 1.4 | 61.4 | 5.0 | 106.3 | 48.2 |
| DKC30-20 | 136.8 | 14.4 | 9.5 | 0.8 | 3.2 | 61.1 | 4.7 | 105.0 | 48.2 |
| P39D97 | 152.6 | 14.5 | 10.5 | 3.4 | 4.5 | 60.3 | 4.0 | 102.4 | 46.6 |
| HCL116RR2/F7298ZNYKZ | 165.0 | 14.5 | 11.4 | 2.6 | 1.4 | 60.2 | 4.8 | 103.0 | 45.9 |
| P8107HR | 172.4 | 14.6 | 11.8 | 1.5 | 2.1 | 60.6 | 4.5 | 101.1 | 45.8 |

TABLE 7D

Overall comparisons: Fourth Year field trials, 19 reps
UK4201 19 Locations, 19 Reps

| Hybrid | Yield Bu/Ac | H2O Grain | Y/M | SL % | RL % | TW | Har Ap | PlHt | EHt |
|---|---|---|---|---|---|---|---|---|---|
| HCL116RR2/F7298ZNYKZ | 174.9 | 16.6 | 10.5 | 2.7 | 2.2 | 57.8 | 5.6 | 97.4 | 40.7 |
| HC50RR2-1/HCL422 | 165.2 | 17.0 | 9.7 | 5.1 | 0.0 | 57.1 | 5.9 | 104.7 | 42.0 |
| HC50BT1CCR1/HCL422 | 175.9 | 17.1 | 10.3 | 4.1 | 2.1 | 57.8 | 6.2 | 99.4 | 41.7 |
| F1513RMQKZ/T0813Z | 175.3 | 17.3 | 10.1 | 7.3 | 1.2 | 58.3 | 6.4 | 107.6 | 45.6 |
| HCL116RR2/F3632ZNYKZ | 188.9 | 17.4 | 10.9 | 7.5 | 2.8 | 57.9 | 5.6 | 102.8 | 45.3 |
| T9305RHTTZ/A7195ZNYKZ | 178.6 | 17.5 | 10.2 | 5.4 | 1.4 | 57.7 | 6.0 | 102.4 | 41.0 |
| P8906HR | 186.3 | 17.7 | 10.6 | 4.2 | 1.9 | 57.4 | 5.8 | 99.1 | 40.0 |
| 7719/AB19 | 199.5 | 18.0 | 11.1 | 4.0 | 1.3 | 56.2 | 5.9 | 104.3 | 41.7 |
| HCL116CCR1/HCL419BT1-2 | 197.6 | 18.2 | 10.8 | 3.0 | 4.2 | 58.4 | 6.4 | 107.3 | 46.3 |
| SGI028RBDHZ/SGI069ZKDDZ | 173.0 | 18.3 | 9.4 | 4.7 | 3.7 | 56.8 | 5.6 | 99.7 | 43.3 |
| DKC38-89 | 184.7 | 18.5 | 10.0 | 6.1 | 1.1 | 57.7 | 6.2 | 98.1 | 37.1 |
| 7623/AB19 | 203.7 | 18.6 | 11.0 | 1.4 | 2.4 | 55.8 | 6.0 | 102.0 | 43.0 |

BB84 Field Test Trials (Tables 2E to 4E)

TABLE 2E

Overall Comparisons: Year 1 field trials, 47 locations

| Trial | Pedigree | Yld Grain | H2O | SL % | RL % | TW | Eco $/€3 |
|---|---|---|---|---|---|---|---|
| UA6601 | BB85/A1555RMQKZ | 185.5 | 18.2 | 4.2 | 1.2 | 55.9 | $1,466 |
| UA6601 | BB38RMQKZ/MN29 | 181.9 | 17.1 | 4.7 | 0.5 | 57.7 | $1,444 |
| UA6601 | BB84/MM27RMQKZ | 181.6 | 18.8 | 1.2 | 0.7 | 56.3 | $1,432 |
| UA6601 | CB20/A1555RMQKZ | 180.7 | 18.4 | 1.9 | 0.9 | 56.4 | $1,427 |
| UA6601 | CB18/MN7RMQKZ | 179.3 | 17.5 | 2.3 | 0.3 | 55.6 | $1,422 |
| UA6601 | BB202/A1555RMQKZ | 179.6 | 18.7 | 4.1 | 0.6 | 57.1 | $1,417 |
| UA6601 | BB85/MN7RMQKZ | 178.1 | 17.4 | 4.2 | 1.0 | 55.0 | $1,412 |
| UA6601 | BB38RMQKD/MM53 | 177.4 | 16.8 | 1.6 | 0.5 | 58.5 | $1,409 |
| UA6601 | BB59/A1555RMQKZ | 178.4 | 18.8 | 0.4 | 0.9 | 56.1 | $1,407 |
| UA6601 | BC137/MN7RMQKZ | 177.0 | 17.1 | 3.1 | 1.5 | 54.9 | $1,405 |
| UA6601 | BC106/MM27RMQKZ | 178.3 | 19.0 | 1.8 | 2.2 | 57.1 | $1,405 |
| UA6601 | CB18/A1555RMQKZ | 177.4 | 18.3 | 3.8 | 1.2 | 56.6 | $1,402 |
| UA6601 | DKC57-50 | 177.0 | 17.8 | 0.4 | 0.4 | 58.3 | $1,401 |
| UA6601 | BB95/A1555RMQKZ | 175.5 | 17.9 | 4.7 | 1.5 | 57.2 | $1,389 |
| UA6601 | P1018AM1 | 172.2 | 18.2 | 1.2 | 0.8 | 58.0 | $1,361 |
| UA6601 | BC129/MN7RMQKZ | 171.0 | 17.3 | 1.8 | 0.5 | 54.8 | $1,356 |
| UA6601 | BB95/MN7RMQKZ | 169.0 | 17.0 | 4.7 | 1.6 | 56.3 | $1,342 |

TABLE 3E

Overall Comparisons: Year 1 field trials, 60 Replications

| Trial | Pedigree | Yld Grain | H2O | SL % | RL % | TW | EHt | PlHt | Asp | Eco $8/¢ 3 |
|---|---|---|---|---|---|---|---|---|---|---|
| US5601 | CB20/A1555RMQKZ | 190.6 | 19.9 | 0.9 | 1.3 | 53.6 | 3.1 | 8.5 | 6.1 | $1,497 |
| US5601 | BB46/MM27RMQKZ | 190.1 | 20.0 | 0.7 | 0.7 | 53.5 | 3.3 | 8.9 | 6.0 | $1,493 |
| US5601 | BB84/MM27RMQKZ | 190.5 | 20.8 | 0.9 | 0.0 | 53.2 | 3.4 | 8.5 | 6.1 | $1,491 |
| US5601 | BB95/MN7RMQKZ | 184.0 | 17.9 | 0.9 | 0.1 | 55.7 | 3.3 | 8.7 | 5.2 | $1,456 |
| US5601 | BC137/MN7RMQKZ | 184.2 | 18.2 | 0.6 | 0.6 | 54.6 | 3.2 | 8.7 | 5.7 | $1,456 |
| US5601 | DKC57-50 | 184.8 | 19.2 | 0.8 | 0.0 | 55.7 | 3.1 | 8.3 | 5.7 | $1,455 |
| US5601 | CB18/A1555RMQKZ | 184.2 | 19.7 | 0.4 | 2.3 | 53.8 | 2.7 | 8.0 | 5.9 | $1,448 |
| US5601 | BB38RMQKZ/MN29 | 181.5 | 17.8 | 2.6 | 0.1 | 56.7 | 3.2 | 9.0 | 5.6 | $1,436 |
| US5601 | CB18/MN7RMQKZ | 181.5 | 18.7 | 0.1 | 0.3 | 55.3 | 2.9 | 8.1 | 5.5 | $1,432 |
| US5601 | BB95/A1555RMQKZ | 181.2 | 19.0 | 3.8 | 0.7 | 55.1 | 3.0 | 8.7 | 5.6 | $1,428 |
| US5601 | BC106/MM27RMQKZ | 181.7 | 20.8 | 0.0 | 0.9 | 53.6 | 3.0 | 8.4 | 5.7 | $1,422 |
| US5601 | BB202/A1555RMQKZ | 180.4 | 19.5 | 1.2 | 0.6 | 54.5 | 3.0 | 8.5 | 6.0 | $1,419 |
| US5601 | BB85/MN7RMQKZ | 180.1 | 19.3 | 0.7 | 0.8 | 52.9 | 3.1 | 8.8 | 5.7 | $1,418 |
| US5601 | BB85/A1555RMQKZ | 180.0 | 19.4 | 4.2 | 0.5 | 53.8 | 2.9 | 8.4 | 5.6 | $1,416 |
| US5601 | BC129/A1555RMQKZ | 179.5 | 20.8 | 3.3 | 4.5 | 53.2 | 3.5 | 9.0 | 5.8 | $1,405 |
| US5601 | BB38RMQKZ/MM53 | 177.3 | 18.3 | 0.9 | 0.3 | 55.7 | 3.2 | 8.8 | 5.7 | $1,401 |
| US5601 | BB59/A1555RMQKZ | 178.0 | 20.7 | 0.2 | 0.2 | 52.6 | 2.9 | 8.5 | 6.4 | $1,394 |
| US5601 | BC129/MN7RMQKZ | 175.7 | 18.5 | 1.0 | 0.4 | 54.7 | 3.4 | 8.8 | 5.7 | $1,387 |
| US5601 | P1018AM1 | 176.3 | 20.3 | 1.7 | 1.3 | 55.1 | 3.3 | 8.7 | 6.0 | $1,382 |

TABLE 4E

Overall Comparisons: Year 1 field trials, 22 Locations

| Trial | Pedigree | Yld Grain | H2O | SL % | RL % | TW | EHt | PlHt | Asp | Eco $8/¢ 3 |
|---|---|---|---|---|---|---|---|---|---|---|
| UV4706 | 1958/MM69 | 188.6 | 18.1 | 3.0 | 2.3 | 56.3 | 3.5 | 9.6 | 5.3 | $1,491 |
| UV4706 | BB38/LH287RR2-1 | 188.8 | 18.6 | 0.7 | 1.2 | 55.1 | 3.2 | 9.0 | 6.0 | $1,490 |
| UV4706 | BB36RMQKZ/MM59 | 189.0 | 19.7 | 1.3 | 3.1 | 53.6 | 3.3 | 9.2 | 5.9 | $1,486 |
| UV4706 | BB84/MM27RMQKZ | 186.7 | 19.5 | 2.8 | 0.0 | 53.6 | 3.4 | 9.1 | 6.1 | $1,469 |
| UV4706 | DKC62-97 | 185.6 | 18.3 | 0.1 | 0.0 | 56.0 | 3.7 | 9.3 | 6.0 | $1,467 |
| UV4706 | BB38/A1555RMQKZ | 184.6 | 19.7 | 1.2 | 0.3 | 54.3 | 3.5 | 9.2 | 6.3 | $1,451 |
| UV4706 | BB87/A1555RMQKZ | 183.7 | 20.1 | 0.4 | 0.9 | 54.3 | 3.4 | 9.2 | 6.4 | $1,441 |
| UV4706 | BB36RMQKZ/ML22 | 182.0 | 18.1 | 1.7 | 3.6 | 55.3 | 3.2 | 9.1 | 6.0 | $1,439 |
| UV4706 | BB36/A1555RMQKZ | 183.2 | 20.0 | 1.0 | 2.0 | 53.4 | 2.9 | 9.4 | 6.0 | $1,438 |
| UV4706 | BB46/MM27RMQKZ | 182.0 | 18.9 | 1.2 | 0.6 | 55.2 | 3.3 | 9.2 | 5.8 | $1,435 |
| UV4706 | BB46RMQKZ/MM65 | 182.6 | 19.8 | 1.5 | 2.2 | 54.7 | 3.7 | 9.2 | 5.9 | $1,434 |
| UV4706 | BB14RMQKZ/MM53 | 179.7 | 16.1 | 1.3 | 0.8 | 58.2 | 3.5 | 9.1 | 4.9 | $1,431 |
| UV4706 | BB36RMQKZ/MN26 | 181.4 | 19.1 | 0.5 | 0.4 | 54.7 | 3.5 | 9.6 | 6.3 | $1,429 |
| UV4706 | CB30/A1555RMQKZ | 181.6 | 20.3 | 3.9 | 0.7 | 53.1 | 2.9 | 9.1 | 6.4 | $1,424 |
| UV4706 | CB15/A1555RMQKZ | 181.2 | 20.9 | 0.8 | 1.2 | 53.9 | 3.2 | 8.9 | 6.0 | $1,417 |
| UV4706 | BB38RMQKZ/MM67 | 179.7 | 19.1 | 2.7 | 0.0 | 54.3 | 3.3 | 9.3 | 6.0 | $1,416 |
| UV4706 | P1395AM1 | 180.3 | 20.7 | 2.6 | 2.5 | 54.7 | 3.3 | 9.9 | 6.2 | $1,412 |
| UV4706 | BB59/A1555RMQKZ | 179.0 | 19.5 | 0.1 | 0.9 | 54.1 | 3.3 | 9.0 | 6.3 | $1,408 |
| UV4706 | CB18/MN7RMQKZ | 177.0 | 17.0 | 0.9 | 0.1 | 56.2 | 3.3 | 9.0 | 5.2 | $1,405 |
| UV4706 | CB18/A1555RMQKZ | 178.1 | 18.6 | 0.4 | 1.3 | 53.9 | 3.3 | 9.2 | 5.8 | $1,405 |
| UV4706 | BB46RMQKZ/MN26 | 174.5 | 18.3 | 4.9 | 0.0 | 56.0 | 3.5 | 9.5 | 5.5 | $1,379 |
| UV4706 | BB14RMQKZ/MM67 | 171.8 | 16.3 | 2.3 | 0.0 | 57.7 | 3.5 | 9.1 | 4.5 | $1,367 |
| UV4706 | BB36RMQKZ/MM63 | 170.5 | 18.9 | 4.5 | 1.1 | 55.0 | 3.4 | 9.3 | 5.6 | $1,344 |
| UV4706 | BB38RMQKZ/MM70 | 168.6 | 16.3 | 2.6 | 0.0 | 57.5 | 3.6 | 9.2 | 5.0 | $1,342 |
| UV4706 | BB36RMQKZ/ML21 | 170.4 | 19.7 | 3.9 | 1.0 | 54.5 | 3.6 | 9.4 | 7.1 | $1,340 |

BB85 Field Test Trials (Tables 2F to 3F)

TABLE 2F

Overall Comparisons: Year 1 field trials, 47 locations

| Trial | Pedigree | Yld Grain | H2O | SL % | RL % | TW | Eco $8/¢ 3 |
|---|---|---|---|---|---|---|---|
| UA6601 | BB85/A1555RMQKZ | 185.5 | 18.2 | 4.2 | 1.2 | 55.9 | $1,466 |
| UA6601 | BB38RMQKZ/MN29 | 181.9 | 17.1 | 4.7 | 0.5 | 57.7 | $1,444 |
| UA6601 | BB84/MM27RMQKZ | 181.6 | 18.8 | 1.2 | 0.7 | 56.3 | $1,432 |
| UA6601 | CB20/A1555RMQKZ | 180.7 | 18.4 | 1.9 | 0.9 | 56.4 | $1,427 |
| UA6601 | CB18/MN7RMQKZ | 179.3 | 17.5 | 2.3 | 0.3 | 55.6 | $1,422 |
| UA6601 | BB202/A1555RMQKZ | 179.6 | 18.7 | 4.1 | 0.6 | 57.1 | $1,417 |

TABLE 2F-continued

Overall Comparisons: Year 1 field trials, 47 locations

| Trial | Pedigree | Yld Grain | H2O | SL % | RL % | TW | Eco $8/¢3 |
|---|---|---|---|---|---|---|---|
| UA6601 | BB85/MN7RMQKZ | 178.1 | 17.4 | 4.2 | 1.0 | 55.0 | $1,412 |
| UA6601 | BB38RMQKD/MM53 | 177.4 | 16.8 | 1.6 | 0.5 | 58.5 | $1,409 |
| UA6601 | BB59/A1555RMQKZ | 178.4 | 18.8 | 0.4 | 0.9 | 56.1 | $1,407 |
| UA6601 | BC137/MN7RMQKZ | 177.0 | 17.1 | 3.1 | 1.5 | 54.9 | $1,405 |
| UA6601 | BC106/MM27RMQKZ | 178.3 | 19.0 | 1.8 | 2.2 | 57.1 | $1,405 |
| UA6601 | CB18/A1555RMQKZ | 177.4 | 18.3 | 3.8 | 1.2 | 56.6 | $1,402 |
| UA6601 | DKC57-50 | 177.0 | 17.8 | 0.4 | 0.4 | 58.3 | $1,401 |
| UA6601 | BB95/A1555RMQKZ | 175.5 | 17.9 | 4.7 | 1.5 | 57.2 | $1,389 |
| UA6601 | P1018AM1 | 172.2 | 18.2 | 1.2 | 0.8 | 58.0 | $1,361 |
| UA6601 | BC129/MN7RMQKZ | 171.0 | 17.3 | 1.8 | 0.5 | 54.8 | $1,356 |
| UA6601 | BB95/MN7RMQKZ | 169.0 | 17.0 | 4.7 | 1.6 | 56.3 | $1,342 |

TABLE 3F

Overall Comparisons: Year 1 field trials, 15 locations

| Trial | Pedigree | Yld Grain | H2O | SL % | RL % | TW | Asp | Eco $8/¢3 |
|---|---|---|---|---|---|---|---|---|
| UNB501 | BB85/MN7RMQKZ | 193.4 | 13.0 | 5.5 | 0.0 | 58.4 | 5.4 | $1,559 |
| UNB501 | RBO1RMQKZ/MM53 | 187.6 | 12.9 | 2.0 | 0.0 | 60.0 | 5.4 | $1,512 |
| UNB501 | BC129/MN7RMQKZ | 187.2 | 12.9 | 3.9 | 0.0 | 59.0 | 5.4 | $1,510 |
| UNB501 | CB20/MN7RMQKZ | 186.5 | 12.2 | 2.7 | 0.0 | 60.2 | 5.0 | $1,508 |
| UNB501 | BB38RMQKZ/MN29 | 187.3 | 13.3 | 4.6 | 0.0 | 60.3 | 5.4 | $1,508 |
| UNB501 | BB38RMQKZ/MM53 | 186.5 | 13.4 | 3.5 | 0.0 | 60.4 | 5.4 | $1,501 |
| UNB501 | BB202/A1555RMQKZ | 185.3 | 14.3 | 3.2 | 0.0 | 59.1 | 6.3 | $1,486 |
| UNB501 | BB14RMQKZ/MM53 | 183.2 | 12.6 | 1.5 | 0.0 | 60.8 | 5.0 | $1,479 |
| UNB501 | BB201/MN7RMQKZ | 182.0 | 11.9 | 8.1 | 0.0 | 60.7 | 5.1 | $1,473 |
| UNB501 | DKC57-50 | 182.6 | 13.9 | 4.8 | 0.0 | 59.3 | 5.6 | $1,467 |
| UNB501 | BB95/A1555RMQKZ | 181.6 | 13.4 | 5.1 | 0.0 | 60.0 | 5.3 | $1,461 |
| UNB501 | CB20/A1555RMQKZ | 180.3 | 12.3 | 5.2 | 0.0 | 60.1 | 5.1 | $1,457 |
| UNB501 | BC137/MN7RMQKZ | 179.7 | 12.6 | 3.9 | 0.0 | 59.5 | 5.1 | $1,450 |
| UNB501 | CB18/MN7RMQKZ | 178.5 | 12.7 | 3.7 | 0.0 | 59.7 | 5.0 | $1,440 |
| UNB501 | BB95/MN7RMQKZ | 178.1 | 12.3 | 4.2 | 0.0 | 60.3 | 4.6 | $1,439 |
| UNB501 | BB201/A1555RMQKZ | 178.7 | 13.5 | 4.8 | 0.0 | 59.5 | 5.1 | $1,438 |

BB95 Field Test Trials (Tables 2G to 3G)

TABLE 2

Overall Comparisons: Year 1 field trials, 60 Replications

| Trial | Pedigree | Yld Grain | H2O | SL % | RL % | TW | EHt | PlHt | Asp | Eco $8/¢3 |
|---|---|---|---|---|---|---|---|---|---|---|
| US5601 | CB20/A1555RMQKZ | 190.6 | 19.9 | 0.9 | 1.3 | 53.6 | 3.1 | 8.5 | 6.1 | $1,497 |
| US5601 | BB46/MM27RMQKZ | 190.1 | 20.0 | 0.7 | 0.7 | 53.5 | 3.3 | 8.9 | 6.0 | $1,493 |
| US5601 | BB84/MM27RMQKZ | 190.5 | 20.8 | 0.9 | 0.0 | 53.2 | 3.4 | 8.5 | 6.1 | $1,491 |
| US5601 | BB95/MN7RMQKZ | 184.0 | 17.9 | 0.9 | 0.1 | 55.7 | 3.3 | 8.7 | 5.2 | $1,456 |
| US5601 | BC137/MN7RMQKZ | 184.2 | 18.2 | 0.6 | 0.6 | 54.6 | 3.2 | 8.7 | 5.7 | $1,456 |
| US5601 | DKC57-50 | 184.8 | 19.2 | 0.8 | 0.0 | 55.7 | 3.1 | 8.3 | 5.7 | $1,455 |
| US5601 | CB18/A1555RMQKZ | 184.2 | 19.7 | 0.4 | 2.3 | 53.8 | 2.7 | 8.0 | 5.9 | $1,448 |
| US5601 | BB38RMQKZ/MN29 | 181.5 | 17.8 | 2.6 | 0.1 | 56.7 | 3.2 | 9.0 | 5.6 | $1,436 |
| US5601 | CB18/MN7RMQKZ | 181.5 | 18.7 | 0.1 | 0.3 | 55.3 | 2.9 | 8.1 | 5.5 | $1,432 |
| US5601 | BB95/A1555RMQKZ | 181.2 | 19.0 | 3.8 | 0.7 | 55.1 | 3.0 | 8.7 | 5.6 | $1,428 |
| US5601 | BC106/MM27RMQKZ | 181.7 | 20.8 | 0.0 | 0.9 | 53.6 | 3.0 | 8.4 | 5.7 | $1,422 |
| US5601 | BB202/A1555RMQKZ | 180.4 | 19.5 | 1.2 | 0.6 | 54.5 | 3.0 | 8.5 | 6.0 | $1,419 |
| US5601 | BB85/MN7RMQKZ | 180.1 | 19.3 | 0.7 | 0.8 | 52.9 | 3.1 | 8.8 | 5.7 | $1,418 |
| US5601 | BB85/A1555RMQKZ | 180.0 | 19.4 | 4.2 | 0.5 | 53.8 | 2.9 | 8.4 | 5.6 | $1,416 |
| US5601 | BC129/A1555RMQKZ | 179.5 | 20.8 | 3.3 | 4.5 | 53.2 | 3.5 | 9.0 | 5.8 | $1,405 |
| US5601 | BB38RMQKZ/MM53 | 177.3 | 18.3 | 0.9 | 0.3 | 55.7 | 3.2 | 8.8 | 5.7 | $1,401 |
| US5601 | BB59/A1555RMQKZ | 178.0 | 20.7 | 0.2 | 0.2 | 52.6 | 2.9 | 8.5 | 6.4 | $1,394 |
| US5601 | BC129/MN7RMQKZ | 175.7 | 18.5 | 1.0 | 0.4 | 54.7 | 3.4 | 8.8 | 5.7 | $1,387 |
| US5601 | P1018AM1 | 176.3 | 20.3 | 1.7 | 1.3 | 55.1 | 3.3 | 8.7 | 6.0 | $1,382 |

TABLE 3

Overall Comparisons: Year 1 field trials, 55 Replications

| Trial | Pedigree | Yld Grain | H2O | SL % | RL % | TW | EHt | PlHt | Asp | Eco $/¢3 |
|---|---|---|---|---|---|---|---|---|---|---|
| UR5501 | BB38RMQKZ/MN29 | 190.1 | 19.1 | 3.0 | 2.8 | 56.2 | 3.2 | 8.5 | 5.9 | $1,498 |
| UR5501 | CB20/MN7RMQKZ | 189.3 | 19.7 | 0.8 | 0.6 | 54.8 | 3.3 | 8.3 | 5.9 | $1,488 |
| UR5501 | BB201/A1555RMQKZ | 184.0 | 19.0 | 3.3 | 9.1 | 56.2 | 3.2 | 8.3 | 5.6 | $1,450 |
| UR5501 | BB201/MN7RMQKZ | 181.4 | 17.5 | 1.7 | 3.5 | 56.4 | 3.3 | 8.5 | 5.5 | $1,438 |
| UR5501 | BB95/MN7RMQKZ | 180.7 | 19.0 | 1.4 | 1.1 | 55.8 | 3.3 | 8.6 | 5.6 | $1,424 |
| UR5501 | RBO1RMQKZ/MM53 | 179.1 | 18.2 | 2.2 | 4.9 | 55.9 | 3.2 | 8.8 | 5.8 | $1,416 |
| UR5501 | DKC53-78 | 175.3 | 16.8 | 0.4 | 0.5 | 58.9 | 2.8 | 7.8 | 5.4 | $1,393 |
| UR5501 | BC115/II11 | 176.2 | 18.2 | 0.0 | 3.1 | 57.0 | 3.2 | 7.6 | 5.8 | $1,393 |
| UR5501 | BB51RMQKZ/ML9 | 173.9 | 16.8 | 0.2 | 11.2 | 57.7 | 3.4 | 8.2 | 5.3 | $1,382 |
| UR5501 | P0115AM1 | 172.8 | 16.9 | 0.6 | 7.1 | 58.8 | 3.3 | 7.7 | 5.3 | $1,373 |
| UR5501 | BB208/MN7RMQKZ | 173.0 | 18.3 | 2.1 | 0.7 | 56.1 | 3.3 | 8.3 | 5.1 | $1,367 |
| UR5501 | BB36RMQKZ/II11 | 172.3 | 18.6 | 0.0 | 3.0 | 57.0 | 2.9 | 7.8 | 6.2 | $1,360 |
| UR5501 | AB17/ML9 | 169.7 | 16.6 | 1.7 | 6.7 | 58.4 | 3.2 | 8.3 | 5.7 | $1,349 |
| UR5501 | BB38RMQKZ/ML9 | 169.9 | 17.9 | 1.8 | 3.5 | 56.8 | 3.2 | 8.1 | 6.1 | $1,344 |
| UR5501 | RBO1RMQKZ/ML9 | 169.2 | 17.8 | 0.0 | 6.2 | 56.7 | 3.2 | 8.5 | 5.9 | $1,340 |
| UR5501 | BC110/ML9 | 167.1 | 17.7 | 0.8 | 4.1 | 56.0 | 2.8 | 8.1 | 5.9 | $1,324 |
| UR5501 | BB93/A1555RMQKZ | 168.0 | 21.1 | 1.1 | 9.2 | 54.0 | 3.3 | 8.4 | 5.8 | $1,313 |
| UR5501 | BC110RHTTZ/ML9 | 164.3 | 17.3 | 1.7 | 4.1 | 57.2 | 2.9 | 8.3 | 5.8 | $1,303 |

BB98 Field Test Trials (Tables 2H to 7H)

TABLE 2H

Overall Comparisons: First year field trials, 6 locations

| Hybrid | YLD | H2O | Y/M | SL % | RL % | TW | PlHt | EHt | Asp |
|---|---|---|---|---|---|---|---|---|---|
| BB98/LH287BT1-1 | 212.2 | 24.6 | 8.6 | 0.3 | 6.6 | 52.4 | 9.0 | 3.4 | 6.1 |
| BB14/LH287BT1-1 | 199.5 | 24.3 | 8.2 | 0.8 | 2.2 | 53.1 | 9.0 | 3.6 | 5.1 |
| RBO1/LH287BT1-1 | 187.6 | 24.4 | 7.7 | 0.0 | 3.2 | 53.6 | 8.7 | 2.8 | 5.7 |
| RBO1/LH185BT1-2 | 186.0 | 22.7 | 8.2 | 0.0 | 2.6 | 54.4 | 8.9 | 3.4 | 5.9 |
| DeKalb DKC52-45 | 165.5 | 17.8 | 9.3 | 2.1 | 0.7 | 56.7 | 7.9 | 3.1 | 3.5 |

TABLE 3H

Overall Comparisons: Second year field trials, 24 locations

| Hybrid | YLD | H2O | Y/M | SL % | RL % | TW | Asp | PlHt | EHt |
|---|---|---|---|---|---|---|---|---|---|
| BB98/LH287BT1CCR1 | 203.1 | 24.3 | 8.3 | 3.0 | 8.9 | 53.3 | 6.9 | 10.1 | 3.7 |
| RBO1CCR1/MM27 | 195.8 | 23.3 | 8.4 | 2.5 | 3.4 | 53.8 | 6.1 | 9.7 | 3.5 |
| BB33/MN8 | 194.4 | 19.6 | 9.9 | 4.2 | 2.0 | 56.5 | 5.6 | 9.9 | 3.7 |
| HCL301CCR1/HCL516BT | 192.3 | 20.3 | 9.5 | 6.0 | 10.1 | 55.9 | 5.8 | 9.6 | 3.5 |
| DeKalb DKC52-59 | 188.9 | 18.0 | 10.5 | 5.0 | 3.9 | 57.3 | 5.5 | 9.0 | 3.6 |
| HCL205CCR/HCL607BT | 188.5 | 20.6 | 9.1 | 5.3 | 5.0 | 56.0 | 6.2 | 10.2 | 4.0 |
| HCL105CCR/HCL530BT | 185.8 | 19.3 | 9.6 | 2.1 | 8.9 | 57.1 | 5.1 | 9.4 | 3.8 |
| HCL107CCR/HCL407BT | 175.4 | 17.6 | 10.0 | 2.5 | 2.8 | 57.8 | 5.3 | 9.0 | 3.6 |

TABLE 4H

Overall Comparisons: Third year field trials, 9 locations

| Hybrid | YLD | H2O | Y/M | SL % | RL % | TW | Asp |
|---|---|---|---|---|---|---|---|
| BB59/LH287BT1CCR1 | 217.3 | 24.2 | 9.0 | 0.6 | 1.2 | 52.6 | 6.3 |
| BB98/MN8 | 203.8 | 20.9 | 9.8 | 3.9 | 2.3 | 54.0 | 5.8 |
| BB38/MN7 | 207.3 | 24.6 | 8.4 | 0.0 | 1.4 | 51.9 | 4.9 |
| Controls | 206.0 | 24.9 | 8.3 | 0.3 | 2.6 | 52.3 | 6.2 |
| BB38/LH287BT1CCR1 | 207.5 | 26.0 | 8.0 | 0.1 | 0.9 | 51.9 | 6.7 |
| CB11/MM27BT1 | 204.5 | 25.2 | 8.1 | 0.2 | 1.2 | 52.5 | 7.0 |
| BB46/MM27BT1 | 193.4 | 24.7 | 7.8 | 0.7 | 8.6 | 52.6 | 6.0 |

TABLE 5H

Overall Comparisons: Third year field trials, 21 locations

| Hybrid | YLD | H2O | Y/M | SL % | RL % | TW | Asp | PlHt | EHt |
|---|---|---|---|---|---|---|---|---|---|
| BB98/LH287BTCCR | 227.0 | 21.2 | 10.7 | 1.2 | 1.2 | 53.3 | 5.8 | 7.9 | 3.0 |
| BB36/LH287BTCCR | 232.4 | 23.8 | 9.8 | 0.4 | 0.9 | 53.0 | 6.2 | 7.8 | 2.7 |
| Pioneer 33N58 | 220.0 | 22.1 | 10.0 | 0.9 | 0.7 | 54.4 | 6.3 | 8.0 | 3.2 |
| BB38/LH287BTCCR | 224.7 | 23.7 | 9.5 | 0.2 | 1.7 | 53.5 | 5.8 | 7.7 | 2.8 |
| DeKalb DKC64-24 | 218.8 | 22.5 | 9.7 | 1.1 | 1.7 | 53.8 | 5.4 | 7.3 | 2.7 |
| BB38/LH287RR2 | 214.5 | 22.6 | 9.5 | 1.8 | 0.3 | 53.6 | 5.9 | 7.6 | 2.7 |
| BB98/MN7 | 208.2 | 20.5 | 10.2 | 0.5 | −0.2 | 53.9 | 4.9 | 7.7 | 3.1 |
| BB36/MN7 | 214.7 | 23.4 | 9.2 | 1.1 | 0.6 | 53.4 | 5.3 | 7.8 | 2.7 |

TABLE 6H

Overall Comparisons: Fourth year field trials, 26 locations

| Hybrid | YLD | H2O | Y/M | SL % | RL % | TW | Asp | PlHt | EHt |
|---|---|---|---|---|---|---|---|---|---|
| BB98/LH287BT1CCR1 | 193.0 | 20.1 | 9.6 | 5.2 | 4.4 | 54.1 | 6.6 | 9.8 | 3.6 |
| RBO1BT1CCR1/ML9 | 183.2 | 16.7 | 11.0 | 1.0 | 2.3 | 56.4 | 6.3 | 9.7 | 3.7 |
| DeKalb DKC61-69 | 188.8 | 19.7 | 9.6 | 5.0 | 4.6 | 55.3 | 5.8 | 9.7 | 3.8 |
| BB59/LH287BT1CCR1 | 189.7 | 20.9 | 9.1 | 2.9 | 3.5 | 54.5 | 6.8 | 9.5 | 3.3 |
| RBO1CCR1/LH287BT1-1 | 184.8 | 19.8 | 9.4 | 3.0 | 0.7 | 55.2 | 5.9 | 9.8 | 3.1 |
| T5056RMQKZ/T8147Z | 187.7 | 21.8 | 8.6 | 1.5 | 0.8 | 54.7 | 6.6 | 9.4 | 3.4 |
| HCL301CCR1/HCL516BT1 | 176.9 | 18.0 | 9.8 | 4.9 | 1.7 | 55.9 | 5.6 | 9.3 | 3.3 |

TABLE 7H

Overall Comparisons: Fifth year field trials, 25 locations

| Hybrid | YLD | H2O | Y/M | SL % | RL % | TW | Asp | PlHt | EHt |
|---|---|---|---|---|---|---|---|---|---|
| BB38/LH287BT1CCR1 | 210.3 | 20.7 | 10.1 | 1.6 | 4.4 | 57.0 | 6.3 | 9.7 | 3.4 |
| BB87/LH287BT1CCR1 | 209.6 | 20.6 | 10.2 | 3.6 | 6.3 | 56.3 | 6.2 | 9.6 | 3.6 |
| BB36/LH287BT1CCR1 | 203.0 | 21.0 | 9.7 | 0.5 | 5.0 | 56.9 | 6.1 | 9.3 | 3.4 |
| BB59/LH287BT1CCR1 | 197.7 | 19.6 | 10.1 | 1.0 | 4.3 | 56.6 | 6.2 | 9.6 | 3.6 |
| BB98/LH287BT1CCR1 | 199.7 | 19.9 | 10.0 | 2.5 | 5.2 | 56.2 | 6.0 | 9.6 | 3.5 |
| BB36/LH287BT1CCR1 | 202.3 | 21.6 | 9.4 | 0.9 | 4.8 | 56.7 | 6.3 | 9.7 | 3.4 |
| CB15/LH287BT1CCR1 | 203.5 | 22.1 | 9.2 | 1.0 | 7.0 | 56.7 | 6.1 | 9.3 | 3.4 |
| BB59/LH287BT1CCR1 | 194.9 | 19.4 | 10.1 | 0.8 | 3.7 | 56.7 | 6.1 | 9.5 | 3.5 |
| DeKalb DKC63-84 | 190.5 | 19.4 | 9.8 | 1.6 | 3.1 | 56.8 | 6.5 | 9.9 | 3.7 |
| Pioneer 1184XR | 188.9 | 19.7 | 9.6 | 0.4 | 3.1 | 58.8 | 6.6 | 9.5 | 3.9 |
| Pioneer 33D49 | 195.7 | 21.9 | 8.9 | 0.2 | 3.2 | 57.7 | 6.2 | 9.5 | 3.6 |

BB201 Field Test Trials (Tables 2I to 19I)

TABLE 2I

Overall Comparisons: First year field trials, 4 locations

| Hybrid | YLD | H2O | Y/M | SL % | RL % | TW | Asp | PlHt | EHt |
|---|---|---|---|---|---|---|---|---|---|
| DeKalb DKC58-16 | 191.6 | 19.7 | 9.7 | 3.1 | 31.4 | 56.7 | 3.2 | | |
| CB1/MN5 | 195.4 | 24.3 | 8.1 | 5.1 | 6.5 | 54.5 | 4.0 | 9.7 | 3.9 |
| BB14/LH287BT1CCR1 | 189.6 | 22.4 | 8.4 | 3.8 | 7.7 | 56.1 | 3.5 | 9.4 | 3.3 |
| BC5/LH287BT1CCR1 | 179.7 | 23.8 | 7.6 | 1.7 | 22.7 | 55.0 | 4.5 | 9.4 | 3.4 |
| BB201/MN5 | 182.5 | 21.6 | 8.4 | 3.8 | 1.5 | 56.7 | 5.0 | 9.8 | 3.4 |
| HCL301CCR1/HCL516BT1 | 167.4 | 19.2 | 8.7 | 19.7 | 2.7 | 57.9 | 3.5 | 8.4 | 3.1 |
| BB14/MN5 | 173.8 | 23.5 | 7.4 | 6.8 | 0.2 | 55.2 | 4.5 | 9.2 | 3.1 |

TABLE 3I

| Overall Comparisons: Second year field trials, 7 locations | | | | | | | | |
|---|---|---|---|---|---|---|---|---|
| Hybrid | YLD | H2O | Y/M | SL % | RL % | TW | Asp | PlHt | EHt |
| BB201/ML8 | 194.8 | 22.4 | 8.7 | 1.0 | 1.2 | 53.8 | 5.0 | 9.7 | 4.2 |
| RBO1CCR1/ML8 | 183.7 | 25.4 | 7.2 | 0.8 | 2.1 | 52.4 | 5.0 | 10.2 | 3.9 |
| HCL301RR2/HCL516 | 178.1 | 27.2 | 6.6 | 0.4 | 1.6 | 52.2 | 6.0 | 9.8 | 4.0 |
| HCL107RR2/HCL405 | 167.6 | 23.3 | 7.2 | 0.2 | 0.0 | 53.5 | 4.7 | 9.0 | 3.8 |
| HCL105RR2/HCL531 | 158.3 | 24.6 | 6.4 | 1.2 | 0.2 | 53.3 | 4.7 | 9.4 | 3.7 |

TABLE 4I

| Overall Comparisons: Second year field trials, 7 locations | | | | | | | | |
|---|---|---|---|---|---|---|---|---|
| Hybrid | YLD | H2O | Y/M | SL % | RL % | TW | Asp | PlHt | EHt |
| BB201/ML9 | 194.3 | 24.3 | 8.0 | 0.2 | 0.4 | 52.5 | 5.3 | 9.8 | 4.0 |
| HCL301RR2/HCL516 | 191.9 | 28.4 | 6.8 | 0.0 | 0.0 | 52.2 | 5.7 | 10.0 | 3.7 |
| HCL107RR2/HCL405 | 169.5 | 23.3 | 7.3 | 2.1 | 0.2 | 53.4 | 5.3 | 9.3 | 3.8 |
| HCL105RR2/HCL531 | 166.7 | 24.4 | 6.8 | 0.4 | 1.0 | 53.2 | 5.0 | 9.8 | 3.9 |

TABLE 5I

| Overall Comparisons: Third year field trials, 7 locations | | | | | | | | |
|---|---|---|---|---|---|---|---|---|
| Hybrid | YLD | H2O | Y/M | SL % | RL % | TW | Asp | PlHt | EHt |
| BB201/ML8 | 181.5 | 19.2 | 9.5 | 0.9 | 0.3 | 56.8 | 6.5 | 9.8 | 3.6 |
| HCL301RR2/HCL516 | 168.3 | 20.6 | 8.2 | 1.3 | 0.0 | 57.9 | 7.0 | 10.0 | 3.9 |
| HCL112RR2/HCL437 | 151.7 | 17.8 | 8.5 | 0.4 | 0.0 | 58.6 | 6.0 | 9.7 | 3.1 |

TABLE 6I

| Overall Comparisons: Third year field trials, 10 locations | | | | | | | | |
|---|---|---|---|---|---|---|---|---|
| Hybrid | YLD | H2O | Y/M | SL % | RL % | TW | Asp | PlHt | EHt |
| BB59/LH287RR2-1 | 198.4 | 20.7 | 9.6 | 0.5 | 1.1 | 54.6 | 6.8 | 9.2 | 3.1 |
| BB201/MN7CCR1 | 189.5 | 17.9 | 10.6 | 0.2 | 0.3 | 54.8 | 6.1 | 9.4 | 3.8 |
| BB201/MM27CCR1 | 188.2 | 19.7 | 9.5 | 1.3 | 0.0 | 54.1 | 5.9 | 9.2 | 3.6 |
| HCL301RR2/HCL516 | 184.2 | 19.8 | 9.3 | 1.1 | 0.0 | 55.1 | 6.5 | 9.0 | 3.1 |
| HCL112RR2/HCL437 | 172.5 | 16.9 | 10.2 | 0.7 | 0.1 | 56.6 | 5.3 | 8.9 | 3.1 |

TABLE 7I

| Overall Comparisons: Fourth year field trials, 21 locations | | | | | | | | |
|---|---|---|---|---|---|---|---|---|
| Hybrid | YLD | H2O | Y/M | SL % | RL % | TW | Asp | PlHt | EHt |
| RBO1BT1CCR1/ML9 | 187.0 | 18.1 | 10.3 | 2.1 | 4.6 | 57.3 | 5.6 | 8.8 | 3.0 |
| BB201/ML12 | 186.9 | 18.0 | 10.4 | 1.4 | 14.0 | 56.7 | 5.2 | 9.4 | 3.8 |
| HCL301RR2/HCL516BT1 | 184.4 | 19.3 | 9.6 | 1.4 | 6.1 | 57.0 | 4.8 | 8.6 | 3.3 |
| NP2660GT/NP2727 | 184.6 | 19.7 | 9.3 | 0.9 | 5.3 | 56.9 | 6.0 | 9.5 | 3.9 |
| 1958/ML8 | 186.3 | 20.6 | 9.0 | 2.8 | 2.3 | 55.8 | 5.7 | 9.2 | 3.8 |
| NP2660GTCBLLRW/NP2727 | 184.7 | 20.2 | 9.1 | 0.8 | 7.0 | 56.9 | 5.7 | 9.2 | 3.6 |
| DeKalb DKC52-59 | 174.3 | 17.4 | 10.0 | 8.2 | 0.0 | 57.2 | 4.4 | 8.5 | 3.5 |

TABLE 8I

| Overall Comparisons: Fourth year field trials, 23 locations | | | | | | | | | |
|---|---|---|---|---|---|---|---|---|---|
| Hybrid | YLD | H2O | Y/M | SL % | RL % | TW | Asp | PlHt | EHt |
| BB201/MN7CCR1 | 182.1 | 17.1 | 10.7 | 1.3 | 2.8 | 56.7 | 4.6 | 9.1 | 3.6 |
| DeKalb DKC57-50 | 184.8 | 21.1 | 8.8 | 1.2 | 0.0 | 57.2 | 5.7 | 8.8 | 3.5 |
| BB59/LH287BT1CCR1 | 182.8 | 21.4 | 8.6 | 1.0 | 4.1 | 56.8 | 5.8 | 9.0 | 3.5 |
| RBO1CCR1/LH287BT1-1 | 182.0 | 21.9 | 8.3 | 1.2 | 5.4 | 57.3 | 5.6 | 9.4 | 3.4 |
| 1958/ML8 | 179.6 | 21.2 | 8.5 | 0.7 | 1.0 | 56.7 | 5.9 | 9.2 | 3.9 |
| BB59/A1555RMQKZ | 179.6 | 21.5 | 8.3 | 1.7 | 1.7 | 56.8 | 5.8 | 8.7 | 3.1 |
| HCL301CCR1/HCL516BT1 | 176.0 | 19.9 | 8.9 | 3.3 | 1.3 | 57.9 | 4.8 | 8.9 | 3.4 |

TABLE 9I

| Overall Comparisons: Fifth year field trials, 45 locations | | | | | | | | | |
|---|---|---|---|---|---|---|---|---|---|
| Hybrid | YLD | H2O | Y/M | SL % | RL % | TW | Asp | PlHt | Eht |
| SGI104RMQKZ × SGI105 | 166.4 | 16.9 | 10.32 | 2.4 | 2.7 | 57.4 | | | |
| BB201 × MN7RMQKZ | 165.2 | 17.0 | 10.52 | 1.9 | 2.8 | 54.3 | | | |
| A0241RMQKZ × R8919Z | 164.4 | 15.4 | 10.97 | 1.9 | 2.0 | 58.2 | | | |
| NP2643GT × NP2727CBLLRW | 162.2 | 18.0 | 9.43 | 1.1 | 1.1 | 55.5 | | | |
| RBO1RMQKZ × MM53 | 160.8 | 17.3 | 9.78 | 2.9 | 1.4 | 56.0 | | | |
| RBO1RMQKZ × ML9 | 160.0 | 17.2 | 9.84 | 1.0 | 2.2 | 56.2 | | | |
| Dekalb DKC53-78RIB | 159.1 | 16.2 | 10.28 | 2.3 | 1.0 | 57.4 | | | |
| NP2660GTCBLLRW × NP2727 | 157.7 | 17.6 | 9.28 | 2.0 | 5.3 | 56.4 | | | |
| Pioneer P0115AM1 | 155.3 | 16.0 | 10.06 | 3.4 | 5.0 | 57.9 | | | |
| 1958 × ML8 | 153.8 | 18.3 | 8.90 | 2.2 | 0.2 | 55.6 | | | |

TABLE 10I

| Overall Comparisons: Fifth year field trials, 28 locations | | | | | | | | | |
|---|---|---|---|---|---|---|---|---|---|
| Hybrid | YLD | H2O | Y/M | SL % | RL % | TW | Asp | PlHt | EHt |
| SGI104RMQKZ × SGI105 | 186.8 | 18.5 | 10.1 | 2.1 | 4.4 | 57.3 | 5.6 | 7.9 | 3.1 |
| BB201/A1555RM QKZ | 184.0 | 19.0 | 9.7 | 3.3 | 9.1 | 56.2 | 5.6 | 8.3 | 3.2 |
| BB201/MN7RM QKZ | 181.4 | 17.5 | 10.4 | 1.7 | 3.5 | 56.4 | 5.5 | 8.5 | 3.3 |
| NP2643GT × NP2727CBLLRW | 182.3 | 19.8 | 9.2 | 0.4 | 4.1 | 54.1 | 6.8 | 9.0 | 3.6 |
| RBO1RMQKZ/MM53 | 179.1 | 18.2 | 9.8 | 2.2 | 4.9 | 55.9 | 5.8 | 8.8 | 3.2 |
| DeKalb DKC53-78 | 175.3 | 16.8 | 10.4 | 0.4 | 0.5 | 58.9 | 5.4 | 7.8 | 2.8 |
| 1958/ML8 | 176.9 | 19.9 | 8.9 | 0.3 | 1.2 | 55.1 | 6.2 | 8.7 | 3.7 |
| Pioneer P0115AM1 | 172.8 | 16.9 | 10.2 | 0.6 | 7.1 | 58.8 | 5.3 | 7.7 | 3.3 |

BC106 Field Test Trials (Tables 2J to 13J)

TABLE 2J

| Overall Comparisons: First year field trials, 6 locations | | | | | | | | | |
|---|---|---|---|---|---|---|---|---|---|
| Hybrid | Yld Grain | H2O | Y/M | SL % | RL % | TW | EHt | PlHt | Asp |
| BC106 × LH287BT1-1 | 224.4 | 18.2 | 7.6 | 1.1 | 7.1 | 57.4 | 3.1 | 10.2 | 5.6 |
| P33P67 | 206.4 | 19.1 | 6.8 | 3.5 | 1.3 | 57.2 | 3.4 | 9.8 | 5.0 |
| CB1 × LH287BT1-1 | 201.9 | 19.2 | 6.4 | 0.9 | 11.7 | 56.8 | 3.1 | 9.5 | 5.4 |
| RBO1 × LH287BT1-1 | 196.1 | 16.8 | 7.3 | 2.0 | 4.5 | 58.6 | 3.3 | 9.5 | 5.0 |
| RBO1 × LH287 | 194.3 | 16.6 | 7.1 | 2.2 | 0.9 | 58.6 | 3.1 | 9.5 | 4.6 |
| KW4773 × LH287BT1-1 | 193.7 | 19.0 | 6.3 | 2.4 | 23.0 | 56.9 | 3.3 | 9.5 | 4.8 |

TABLE 3J

Overall Comparisons: Second year field trials, 8 locations

| Hybrid | Yld Grain | H2O | Y/M | SL % | RL % | TW | EHt | PlHt | Asp |
|---|---|---|---|---|---|---|---|---|---|
| BC106 × LH287BT1RR2 | 220.1 | 20.9 | 10.7 | 1.4 | 0.5 | 55.3 | 3.5 | 10.1 | 6.7 |
| CB1 × UNW1 | 204.4 | 20.5 | 10.1 | 0.8 | 0.2 | 55.6 | 3.1 | 9.4 | 5.7 |
| P33P67 | 204.2 | 21.2 | 9.8 | 4.6 | 0.8 | 55.5 | 4.2 | 10.6 | 5.1 |
| DKC63-79 | 203.9 | 20.8 | 10.0 | 3.6 | 0.0 | 55.6 | 3.7 | 9.7 | 5.4 |
| Controls | 201.5 | 20.9 | 9.9 | 4.1 | 0.9 | 55.5 | 3.5 | 9.8 | 5.2 |
| CB1 × LH287BT1-1 | 197.8 | 21.9 | 9.4 | 6.6 | 3.4 | 54.9 | 3.1 | 9.6 | 5.1 |
| BC5 × LH287BT1-1 | 197.3 | 19.8 | 10.1 | 5.0 | 0.0 | 55.8 | 3.4 | 9.5 | 4.7 |

TABLE 4J

Overall Comparisons: Second year field trials, 8 locations

| Hybrid | Yld Grain | H2O | Y/M | SL % | RL % | TW | EHt | PlHt | Asp |
|---|---|---|---|---|---|---|---|---|---|
| BC106 × MN5 | 220.4 | 19.6 | 11.5 | 0.8 | 0.0 | 55.9 | 4.0 | 9.7 | 6.2 |
| DKC63-79 | 217.2 | 19.8 | 11.2 | 1.1 | 0.0 | 56.2 | 3.9 | 9.4 | 5.8 |
| P34A16 | 216.9 | 18.6 | 11.8 | 1.4 | 0.0 | 56.9 | 3.4 | 9.5 | 5.5 |
| BC5 × LH287 | 208.1 | 18.6 | 11.4 | 3.7 | 0.3 | 56.3 | 3.4 | 8.9 | 5.5 |
| CC2 × MN5 | 207.3 | 18.4 | 11.6 | 1.5 | 1.5 | 56.7 | 4.0 | 9.9 | 5.7 |
| RBO1 × LH287BT1-1 | 206.1 | 18.7 | 11.3 | 0.0 | 0.0 | 56.6 | 2.9 | 9.0 | 5.8 |

TABLE 5J

Overall Comparisons: Third year field trials, 18 locations

| Hybrid | Yld Grain | H2O | Y/M | SL % | RL % | TW | EHt | PlHt | Asp |
|---|---|---|---|---|---|---|---|---|---|
| CB1 × LH287BT1CRW2-1 | 217.8 | 19.8 | 11.3 | 3.8 | 10.1 | 55.3 | 2.9 | 9.2 | 6.0 |
| BC106 × LH287BT1CRW2-1 | 213.7 | 18.9 | 11.5 | 0.9 | 11.9 | 55.5 | 3.0 | 9.0 | 5.9 |
| BC5 × LH287BT1CRW2-1 | 210.5 | 18.4 | 11.6 | 0.7 | 7.7 | 56.0 | 3.0 | 9.0 | 5.9 |
| LH287 × SGI890HX1-1 | 206.7 | 20.5 | 10.2 | 1.5 | 10.2 | 54.9 | 3.7 | 9.9 | 6.5 |
| Controls | 204.2 | 20.1 | 10.4 | 2.1 | 6.8 | 55.3 | 3.4 | 9.4 | 6.1 |
| DKC63-79 | 199.0 | 19.9 | 10.5 | 1.6 | 5.2 | 56.0 | 3.6 | 9.0 | 5.9 |
| HC53RR2-1 × LH324BT1CRW2 | 196.7 | 20.3 | 9.9 | 0.2 | 4.6 | 55.2 | 3.4 | 9.0 | 6.4 |
| P32B29 | 194.7 | 21.9 | 9.1 | 4.7 | 2.7 | 54.6 | 4.0 | 10.3 | 5.7 |

TABLE 6J

Overall Comparisons: Fourth year field trials, 25 locations

| Hybrid | Yld Grain | H2O | Y/M | SL % | RL % | TW | EHt | PlHt | Asp |
|---|---|---|---|---|---|---|---|---|---|
| BC5/LH287BT1CCR1 | 218.3 | 19.9 | 11.3 | 3.4 | 6.7 | 54.0 | 3.6 | 9.2 | 5.3 |
| BC106/MN20BT1 | 215.4 | 19.9 | 11.3 | 0.7 | 1.0 | 54.7 | 3.5 | 8.9 | 6.7 |
| CB1/LH287BT1CCR1 | 215.3 | 21.2 | 10.6 | 6.7 | 3.1 | 53.5 | 3.1 | 9.4 | 6.0 |
| P33F88 | 212.5 | 21.0 | 10.5 | 9.0 | 4.0 | 54.3 | 3.6 | 9.8 | 5.8 |
| Controls | 210.3 | 19.9 | 10.9 | 6.0 | 4.8 | 54.5 | 3.5 | 9.4 | 5.6 |
| CB1/UNW1BT1 | 209.7 | 19.4 | 11.1 | 2.1 | 7.0 | 54.9 | 3.5 | 9.2 | 5.7 |
| HCL307CCR1/HCL603BT1 | 207.6 | 20.0 | 10.7 | 11.0 | 5.1 | 54.6 | 3.7 | 9.2 | 4.8 |
| LH331/UNW1 | 198.1 | 18.2 | 11.2 | 4.1 | 2.9 | 56.0 | 3.7 | 9.5 | 6.1 |

TABLE 7J

Overall Comparisons: Fourth year field trials, 40 locations

| Hybrid | Yld Grain | H2O | Y/M | SL % | RL % | TW |
|---|---|---|---|---|---|---|
| BB38/LH287BT1CCR1 | 216.4 | 19.8 | 11.1 | 1.8 | 3.2 | 55.6 |
| BC106/LH287BT1CCR1 | 211.9 | 19.7 | 11.0 | 3.4 | 9.0 | 55.0 |
| CC1/LH287BT1CCR1 | 211.2 | 21.3 | 10.1 | 0.8 | 1.9 | 55.4 |
| CB1/LH287BT1CCR1 | 210.7 | 20.1 | 10.7 | 2.5 | 5.7 | 54.9 |
| DKC61-69 | 209.9 | 17.7 | 12.0 | 4.0 | 3.5 | 57.5 |
| DKC63-42 | 208.7 | 19.2 | 11.1 | 4.8 | 2.5 | 57.1 |
| BB46/LH287BT1CCR1 | 208.1 | 18.5 | 11.5 | 4.7 | 8.2 | 55.2 |
| BC5/LH287BT1CCR1 | 204.9 | 19.0 | 11.0 | 4.2 | 6.1 | 54.5 |
| P33F88 | 203.7 | 20.0 | 10.3 | 3.1 | 2.5 | 57.5 |

TABLE 8J

Overall Comparisons: Fifth year field trials, 30 locations

| Hybrid | Yld Grain | H2O | Y/M | SL % | RL % | TW | EHt | PlHt | Asp |
|---|---|---|---|---|---|---|---|---|---|
| BB36/MN7 | 222.7 | 24.2 | 9.5 | 1.1 | 0.9 | 53.0 | 2.9 | 8.2 | 5.6 |
| BC106/MM27 | 222.0 | 22.8 | 10.0 | 0.7 | 3.8 | 53.5 | 2.8 | 7.8 | 5.7 |
| CB11/MM27 | 221.9 | 23.4 | 9.7 | 0.6 | 2.6 | 53.3 | 3.0 | 8.1 | 5.9 |
| BB38/LH287BT1-1 | 219.7 | 24.2 | 9.3 | 1.3 | 1.0 | 53.1 | 3.0 | 8.0 | 5.9 |
| DKC63-42 | 219.5 | 23.6 | 9.7 | 1.2 | 0.9 | 53.7 | 3.2 | 7.8 | 6.2 |
| CB11/MM27BT1 | 217.9 | 24.1 | 9.3 | 0.7 | 4.2 | 53.3 | 3.2 | 8.2 | 6.1 |
| P33W84 | 214.2 | 23.0 | 9.5 | 0.0 | 0.5 | 54.2 | 2.8 | 8.2 | 6.2 |
| DKC61-69 | 213.9 | 21.8 | 10.1 | 1.5 | 3.6 | 54.5 | 3.2 | 7.8 | 5.2 |

TABLE 9J

Overall Comparisons: Sixth year field trials, 18 locations

| Hybrid | Yld Grain | H2O | Y/M | SL % | RL % | TW | EHt | PlHt | Asp |
|---|---|---|---|---|---|---|---|---|---|
| BB59/LH287BT1CCR1 | 195.8 | 21.3 | 9.7 | 1.0 | 3.2 | 55.1 | 3.6 | 9.7 | 6.7 |
| BC106/MM27BT1 | 192.0 | 21.1 | 9.5 | 2.3 | 2.0 | 55.4 | 3.9 | 9.8 | 6.7 |
| AGR1981/ML8 | 191.8 | 19.2 | 10.6 | 3.5 | 1.5 | 55.4 | 3.9 | 10.1 | 6.5 |
| DKC61-69 | 191.3 | 19.7 | 10.1 | 3.2 | 0.6 | 55.3 | 3.8 | 9.7 | 5.9 |
| BB38/MN7CCR1 | 190.1 | 21.4 | 9.5 | 1.8 | 0.6 | 55.2 | 3.5 | 9.9 | 6.1 |
| DKC59-35 | 190.1 | 21.9 | 9.1 | 2.4 | 0.0 | 54.8 | 3.9 | 9.9 | 6.8 |
| Controls | 189.9 | 20.6 | 9.7 | 2.9 | 1.0 | 55.3 | 3.7 | 9.9 | 6.4 |
| BB38/LH287RR2-1 | 189.1 | 21.5 | 9.2 | 2.5 | 0.8 | 55.2 | 3.8 | 10.1 | 6.6 |
| RB01CCR1/LH287BT1-1 | 185.7 | 20.5 | 9.5 | 7.4 | 0.5 | 56.0 | 3.6 | 10.0 | 6.3 |
| BB59/LH287RR2-1 | 185.2 | 19.4 | 10.0 | 1.2 | 0.8 | 55.4 | 3.6 | 9.6 | 6.4 |

TABLE 10J

Overall Comparisons: Seventh year field trials, 20 locations

| Hybrid | Yld Grain | H2O | Y/M | SL % | RL % | TW | EHt | PlHt | Asp |
|---|---|---|---|---|---|---|---|---|---|
| BB38/LH287BT1CCR1 | 205.2 | 20.2 | 10.4 | 0.9 | 1.0 | 57.4 | 3.7 | 9.5 | 6.4 |
| BB36/LH287BT1CCR1 | 203.2 | 20.7 | 10.0 | 0.3 | 3.4 | 56.8 | 3.3 | 9.6 | 6.3 |
| BC106/MM27RMQKZ | 202.1 | 19.0 | 10.8 | 0.7 | 0.6 | 57.0 | 3.8 | 9.8 | 6.0 |
| BB59/LH287BT1CCR1 | 199.9 | 19.2 | 10.7 | 0.3 | 1.6 | 56.9 | 3.4 | 9.5 | 6.1 |
| DKC63-84 | 195.5 | 19.0 | 10.5 | 1.5 | 0.5 | 57.1 | 3.6 | 9.7 | 6.8 |
| BB36RR2/A1555ZNYKZ | 193.7 | 20.7 | 9.6 | 0.4 | 0.6 | 57.5 | 3.2 | 9.7 | 6.0 |
| BB36/LH287RR2-1 | 192.7 | 19.9 | 9.9 | 1.1 | 1.2 | 57.4 | 3.4 | 9.9 | 5.9 |
| P1184XR | 191.5 | 19.2 | 10.2 | 0.3 | 1.4 | 59.3 | 4.2 | 9.8 | 6.6 |

TABLE 11J

Overall Comparisons: Eight year field trials, 21 locations

| Hybrid | Yld Grain | H2O | Y/M | SL % | RL % | TW | EHt | PlHt | Asp |
|---|---|---|---|---|---|---|---|---|---|
| BB38/ML9 | 186.8 | 16.7 | 11.2 | 0.1 | 0.7 | 58.0 | 3.2 | 9.0 | 5.6 |
| BC106RHTTZ/MM27 | 187.9 | 20.7 | 9.1 | 0.0 | 0.2 | 53.3 | 3.1 | 8.7 | 6.4 |
| BC106/MM27RMQKZ | 185.0 | 20.4 | 9.1 | 0.2 | 2.4 | 54.0 | 3.6 | 9.3 | 6.0 |
| DKC57-50 | 182.9 | 18.6 | 9.8 | 0.3 | 0.0 | 56.3 | 3.6 | 9.4 | 5.8 |
| P1018AM1 | 176.7 | 19.4 | 9.1 | 1.2 | 8.3 | 56.3 | 3.8 | 9.6 | 6.2 |
| BB59/A1555RMQKZ | 174.6 | 19.4 | 9.0 | 0.4 | 2.5 | 53.9 | 3.0 | 9.4 | 6.1 |

TABLE 12J

Overall Comparisons: Eight year field trials, 24 locations

| Hybrid | Yld Grain | H2O | Y/M | SL % | RL % | TW | EHt | PlHt | Asp |
|---|---|---|---|---|---|---|---|---|---|
| CB18/MN7RMQKZ | 186.2 | 18.0 | 10.3 | 2.0 | 0.8 | 54.9 | 3.0 | 8.0 | 5.5 |
| DKC57-50 | 184.5 | 18.2 | 10.1 | 1.1 | 0.3 | 56.9 | 3.0 | 8.2 | 5.6 |
| BB59/A1555RMQKZ | 184.0 | 20.3 | 9.1 | 1.0 | 3.6 | 52.4 | 2.9 | 8.6 | 6.5 |
| BC106/MM27RMQKZ | 182.7 | 20.8 | 8.8 | 0.2 | 1.0 | 53.8 | 3.0 | 8.4 | 6.2 |
| P1018AM1 | 177.6 | 19.7 | 9.0 | 3.7 | 2.8 | 54.2 | 3.3 | 8.8 | 5.9 |
| BB38RMQKZ/ML9 | 174.5 | 16.7 | 10.4 | 1.1 | 2.0 | 57.9 | 2.9 | 8.4 | 5.8 |

TABLE 13J

Overall Comparisons: Eight year field trials, 30 locations

| Hybrid | Yld Grain | H2O | Y/M | SL % | RL % | TW | EHt | PlHt | Asp |
|---|---|---|---|---|---|---|---|---|---|
| DKC57-50 | 184.8 | 19.2 | 9.6 | 0.8 | 0.0 | 55.7 | 3.1 | 8.3 | 5.7 |
| CB18/MN7RMQKZ | 181.5 | 18.7 | 9.7 | 0.1 | 0.3 | 55.3 | 2.9 | 8.1 | 5.5 |
| BC106/MM27RMQKZ | 181.7 | 20.8 | 8.7 | 0.0 | 0.9 | 53.6 | 3.0 | 8.4 | 5.7 |
| BB38RMQKZ/MM53 | 177.3 | 18.3 | 9.7 | 0.9 | 0.7 | 55.7 | 3.2 | 8.8 | 5.7 |
| BB59/A1555RMQKZ | 178.0 | 20.7 | 8.6 | 0.2 | 0.2 | 52.6 | 2.9 | 8.5 | 6.4 |
| P1018AM1 | 176.3 | 20.3 | 8.7 | 1.7 | 1.3 | 55.1 | 3.3 | 8.7 | 6.0 |

BC137 Field Test Trials (Tables 2K to 9K)

TABLE 2K

Overall Comparisons: First year field trials, 5 locations

| Hybrid | YLD | H2O | Y/M | SL % | RL % | TW |
|---|---|---|---|---|---|---|
| BC137/MM27BT1 | 182.6 | 27.5 | 6.7 | 0.0 | 7.7 | 49.7 |
| BB14/LH287BT1-1 | 180.7 | 30.3 | 6.0 | 1.4 | 0.0 | 50.3 |
| HCL301RR2/HCL516BT1 | 163.0 | 26.2 | 6.2 | 0.7 | 1.5 | 50.8 |

TABLE 3K

Overall Comparisons: Second year field trials, 21 locations

| Hybrid | YLD | H2O | Y/M | SL % | RL % | TW | Asp | EHt | PlHt |
|---|---|---|---|---|---|---|---|---|---|
| BB14BT1CCR1/ML9 | 192.9 | 18.8 | 10.3 | 2.1 | 0.8 | 55.4 | 6.5 | 3.6 | 9.2 |
| BC137/MN7CCR1 | 194.8 | 19.2 | 10.1 | 1.7 | 3.7 | 54.8 | 5.7 | 3.3 | 9.6 |
| RBO1BT1CCR1/ML9 | 188.7 | 17.5 | 10.8 | 1.3 | 1.4 | 56.0 | 6.5 | 3.4 | 9.2 |
| HCL301CCR1/HCL516BT1 | 186.1 | 18.5 | 10.0 | 6.3 | 0.7 | 55.8 | 5.6 | 3.5 | 9.3 |
| DKC52-59 | 176.6 | 16.6 | 10.6 | 6.5 | 0.1 | 56.3 | 5.7 | 3.4 | 8.8 |
| HCL301CCR1/HCL418BT1 | 175.5 | 18.3 | 9.6 | 5.1 | 2.6 | 55.7 | 5.6 | 3.2 | 9.4 |

TABLE 4K

Overall Comparisons: Second year field trials, 11 locations

| Hybrid | YLD | H2O | Y/M | SL % | RL % | TW | Asp | EHt | PlHt |
|---|---|---|---|---|---|---|---|---|---|
| HCL301CCR1/HCL516BT1 | 181.8 | 18.1 | 10.0 | 5.9 | 3.9 | 55.7 | 6.1 | 3.3 | 9.3 |
| BC137/MM27CCR1 | 181.3 | 18.0 | 10.1 | 5.1 | 4.5 | 55.2 | 6.4 | 3.3 | 9.1 |
| RBO1BT1CCR1/ML9 | 177.4 | 16.0 | 11.1 | 1.8 | 3.4 | 56.6 | 6.3 | 3.2 | 9.3 |
| DKC52-59 | 169.6 | 16.0 | 10.6 | 5.0 | 0.1 | 56.3 | 6.4 | 3.4 | 8.7 |
| HCL301CCR1/HCL418BT1 | 156.2 | 17.1 | 9.1 | 4.0 | 7.0 | 56.6 | 5.9 | 3.6 | 9.5 |

TABLE 5K

Overall Comparisons: Third year field trials, 19 locations

| Hybrid | YLD | H2O | Y/M | SL % | RL % | TW | Asp | EHt | PlHt |
|---|---|---|---|---|---|---|---|---|---|
| BB59/LH287BT1CCR1 | 191.3 | 23.2 | 8.2 | 1.0 | 1.2 | 55.1 | 6.0 | 3.4 | 9.0 |
| BC137/MN7CCR1 | 175.1 | 20.4 | 8.6 | 1.3 | 2.9 | 55.0 | 5.0 | 3.5 | 8.8 |
| 1958/ML8 | 179.6 | 21.0 | 8.6 | 0.8 | 1.7 | 55.1 | 5.9 | 3.8 | 9.4 |
| RBO1CCR1/LH287BT1-1 | 171.3 | 22.8 | 7.5 | 0.7 | 0.5 | 55.6 | 5.5 | 3.2 | 9.1 |
| HCL301CCR1/HCL516BT1 | 171.8 | 19.6 | 8.8 | 2.9 | 2.1 | 55.9 | 5.1 | 3.3 | 8.7 |

TABLE 6K

Overall Comparisons: Third year field trials, 24 locations

| Hybrid | YLD | H2O | Y/M | SL % | RL % | TW | Asp | EHt | PlHt |
|---|---|---|---|---|---|---|---|---|---|
| BC137/LH287BT1CCR1 | 181.6 | 21.9 | 8.3 | 3.3 | 3.8 | 56.5 | 5.5 | 3.4 | 9.1 |
| DKC57-50 | 183.7 | 21.3 | 8.6 | 1.2 | 0.0 | 56.9 | 5.7 | 3.5 | 8.8 |
| BB59/LH287BT1CCR1 | 181.1 | 21.6 | 8.4 | 0.9 | 4.0 | 56.4 | 5.8 | 3.5 | 9.0 |
| RBO1CCR1/LH287BT1-1 | 180.6 | 22.0 | 8.2 | 1.4 | 5.0 | 57.2 | 5.5 | 3.4 | 9.3 |
| 1958/ML8 | 177.8 | 21.3 | 8.3 | 0.6 | 1.0 | 56.3 | 5.9 | 3.8 | 9.2 |
| HCL301CCR1/HCL516BT1 | 174.7 | 20.1 | 8.7 | 3.3 | 1.2 | 57.4 | 4.8 | 3.4 | 8.9 |

TABLE 7K

| Hybrid | YLD | H2O | Y/M | SL % | RL % | TW | Asp | EHt | PlHt |
|---|---|---|---|---|---|---|---|---|---|
| BC137/MM53 | 186.8 | 18.8 | 9.9 | 3.4 | 9.3 | 54.6 | 4.7 | 3.8 | 9.7 |
| RBO1BT1CCR1/ML9 | 184.7 | 18.7 | 9.9 | 0.9 | 2.4 | 55.9 | 5.7 | 3.6 | 9.4 |
| HCL301RR2/HCL516BT1 | 179.5 | 20.1 | 8.9 | 1.6 | 1.7 | 56.6 | 5.0 | 3.5 | 8.9 |
| BC110/ML9 | 179.2 | 19.0 | 9.5 | 2.1 | 3.6 | 55.3 | 5.4 | 3.7 | 9.2 |
| DKC52-59 | 172.7 | 17.4 | 9.9 | 4.2 | 0.3 | 56.6 | 4.4 | 3.6 | 8.5 |
| R6258RMQKZ/R2683LMSLZ | 172.1 | 19.5 | 8.8 | 1.4 | 3.9 | 56.8 | 5.1 | 3.8 | 9.6 |
| P0463XR | 172.8 | 19.8 | 8.7 | 1.7 | 3.2 | 57.1 | 5.6 | 3.6 | 8.8 |
| NP2660GT/NP2727 | 169.3 | 20.3 | 8.3 | 1.2 | 6.0 | 56.2 | 5.9 | 4.0 | 9.8 |

TABLE 8K

Overall Comparisons: Third year field trials, 25 locations

| Hybrid | YLD | H2O | Y/M | SL % | RL % | TW | Asp | EHt | PlHt |
|---|---|---|---|---|---|---|---|---|---|
| RBO1BT1CCR1/ML9 | 186.8 | 18.2 | 10.3 | 1.4 | 6.3 | 56.2 | 5.7 | 3.5 | 9.2 |
| BC137/ML9 | 186.1 | 19.0 | 9.8 | 1.2 | 9.1 | 55.7 | 5.3 | 3.6 | 9.2 |
| DKC52-59 | 178.1 | 17.5 | 10.2 | 3.5 | 1.2 | 56.6 | 4.9 | 3.5 | 8.4 |
| HCL301RR2/HCL516BT1 | 177.2 | 20.0 | 8.9 | 2.3 | 2.5 | 56.9 | 5.7 | 3.5 | 9.0 |
| NP2660GT/NP2727 | 175.5 | 20.2 | 8.7 | 1.0 | 8.0 | 56.3 | 5.7 | 3.8 | 9.6 |
| R6258RMQKZ/R2683LMSLZ | 176.5 | 19.5 | 9.0 | 1.5 | 4.6 | 57.0 | 5.5 | 3.6 | 9.2 |
| P0463XR | 175.0 | 20.2 | 8.6 | 0.8 | 7.1 | 57.4 | 5.7 | 3.6 | 8.9 |
| BC110/ML9 | 176.6 | 19.2 | 9.2 | 0.7 | 2.4 | 55.3 | 5.5 | 3.4 | 9.2 |
| HCL107RR2/HCL407 | 172.1 | 17.3 | 9.9 | 0.4 | 2.6 | 57.4 | 4.8 | 3.5 | 8.4 |

TABLE 9K

| Overall Comparisons: Fourth year field trials, 30 locations | | | | | | | | | |
|---|---|---|---|---|---|---|---|---|---|
| Hybrid | YLD | H2O | Y/M | SL % | RL % | TW | Asp | EHt | PlHt |
| DKC57-50 | 184.8 | 19.2 | 9.6 | 0.8 | 0.0 | 55.7 | 5.7 | 3.1 | 8.3 |
| BC137/MN7RMQKZ | 184.2 | 18.2 | 10.1 | 0.6 | 0.6 | 54.6 | 5.7 | 3.2 | 8.7 |
| CB18/MN7RMQKZ | 181.5 | 18.7 | 9.7 | 0.1 | 0.3 | 55.3 | 5.5 | 2.9 | 8.1 |
| BB59/A1555RMQKZ | 178.0 | 20.7 | 8.6 | 0.2 | 0.2 | 52.6 | 6.4 | 2.9 | 8.5 |
| BB38RMQKZ/MM53 | 177.3 | 18.3 | 9.7 | 0.9 | 0.3 | 55.7 | 5.7 | 3.2 | 8.8 |
| P1018AM1 | 176.3 | 20.3 | 8.7 | 1.7 | 1.3 | 55.1 | 6.0 | 3.3 | 8.7 |

CB20 Field Test Trials (Tables 2L to 4L)

TABLE 2L

| Overall Comparisons: Year 1 field trials, 60 Replications | | | | | | | | | | |
|---|---|---|---|---|---|---|---|---|---|---|
| Trial | Pedigree | Yld Grain | H2O | SL % | RL % | TW | EHt | PlHt | Asp | Eco $8/C3 |
| US5601 | CB20/A1555RMQKZ | 190.6 | 19.9 | 0.9 | 1.3 | 53.6 | 3.1 | 8.5 | 6.1 | $1,497 |
| US5601 | BB46/MM27RMQKZ | 190.1 | 20.0 | 0.7 | 0.7 | 53.5 | 3.3 | 8.9 | 6.0 | $1,493 |
| US5601 | BB84/MM27RMQKZ | 190.5 | 20.8 | 0.9 | 0.0 | 53.2 | 3.4 | 8.5 | 6.1 | $1,491 |
| US5601 | BB95/MN7RMQKZ | 184.0 | 17.9 | 0.9 | 0.1 | 55.7 | 3.3 | 8.7 | 5.2 | $1,456 |
| US5601 | BC137/MN7RMQKZ | 184.2 | 18.2 | 0.6 | 0.6 | 54.6 | 3.2 | 8.7 | 5.7 | $1,456 |
| US5601 | DKC57-50 | 184.8 | 19.2 | 0.8 | 0.0 | 55.7 | 3.1 | 8.3 | 5.7 | $1,455 |
| US5601 | CB18/A1555RMQKZ | 184.2 | 19.7 | 0.4 | 2.3 | 53.8 | 2.7 | 8.0 | 5.9 | $1,448 |
| US5601 | BB38RMQKZ/MN29 | 181.5 | 17.8 | 2.6 | 0.1 | 56.7 | 3.2 | 9.0 | 5.6 | $1,436 |
| US5601 | CB18/MN7RMQKZ | 181.5 | 18.7 | 0.1 | 0.3 | 55.3 | 2.9 | 8.1 | 5.5 | $1,432 |
| US5601 | BB95/A1555RMQKZ | 181.2 | 19.0 | 3.8 | 0.7 | 55.1 | 3.0 | 8.7 | 5.6 | $1,428 |
| US5601 | BC106/MM27RMQKZ | 181.7 | 20.8 | 0.0 | 0.9 | 53.6 | 3.0 | 8.4 | 5.7 | $1,422 |
| US5601 | BB202/A1555RMQKZ | 180.4 | 19.5 | 1.2 | 0.6 | 54.5 | 3.0 | 8.5 | 6.0 | $1,419 |
| US5601 | BB85/MN7RMQKZ | 180.1 | 19.3 | 0.7 | 0.8 | 52.9 | 3.1 | 8.8 | 5.7 | $1,418 |
| US5601 | BB85/A1555RMQKZ | 180.0 | 19.4 | 4.2 | 0.5 | 53.8 | 2.9 | 8.4 | 5.6 | $1,416 |
| US5601 | BC129/A1555RMQKZ | 179.5 | 20.8 | 3.3 | 4.5 | 53.2 | 3.5 | 9.0 | 5.8 | $1,405 |
| US5601 | BB38RMQKZ/MM53 | 177.3 | 18.3 | 0.9 | 0.3 | 55.7 | 3.2 | 8.8 | 5.7 | $1,401 |
| US5601 | BB59/A1555RMQKZ | 178.0 | 20.7 | 0.2 | 0.2 | 52.6 | 2.9 | 8.5 | 6.4 | $1,394 |
| US5601 | BC129/MN7RMQKZ | 175.7 | 18.5 | 1.0 | 0.4 | 54.7 | 3.4 | 8.8 | 5.7 | $1,387 |
| US5601 | P1018AM1 | 176.3 | 20.3 | 1.7 | 1.3 | 55.1 | 3.3 | 8.7 | 6.0 | $1,382 |

TABLE 3L

| Overall Comparisons: Year 1 field trials, 55 Replications | | | | | | | | | | |
|---|---|---|---|---|---|---|---|---|---|---|
| Trial | Pedigree | Yld Grain | H2O | SL % | RL % | TW | EHt | PlHt | Asp | Eco $8/C3 |
| UR5501 | BB38RMQKZ/MN29 | 190.1 | 19.1 | 3.0 | 2.8 | 56.2 | 3.2 | 8.5 | 5.9 | $1,498 |
| UR5501 | CB20/MN7RMQKZ | 189.3 | 19.7 | 0.8 | 0.6 | 54.8 | 3.3 | 8.3 | 5.9 | $1,488 |
| UR5501 | BB201/A1555RMQKZ | 184.0 | 19.0 | 3.3 | 9.1 | 56.2 | 3.2 | 8.3 | 5.6 | $1,450 |
| UR5501 | BB201/MN7RMQKZ | 181.4 | 17.5 | 1.7 | 3.5 | 56.4 | 3.3 | 8.5 | 5.5 | $1,438 |
| UR5501 | BB95/MN7RMQKZ | 180.7 | 19.0 | 1.4 | 1.1 | 55.8 | 3.3 | 8.6 | 5.6 | $1,424 |
| UR5501 | RBO1RMQKZ/MM53 | 179.1 | 18.2 | 2.2 | 4.9 | 55.9 | 3.2 | 8.8 | 5.8 | $1,416 |
| UR5501 | DKC53-78 | 175.3 | 16.8 | 0.4 | 0.5 | 58.9 | 2.8 | 7.8 | 5.4 | $1,393 |
| UR5501 | BC115/II11 | 176.2 | 18.2 | 0.0 | 3.1 | 57.0 | 3.2 | 7.6 | 5.8 | $1,393 |
| UR5501 | BB51RMQKZ/ML9 | 173.9 | 16.8 | 0.2 | 11.2 | 57.7 | 3.4 | 8.2 | 5.3 | $1,382 |
| UR5501 | P0115AM1 | 172.8 | 16.9 | 0.6 | 7.1 | 58.8 | 3.3 | 7.7 | 5.3 | $1,373 |
| UR5501 | BB208/MN7RMQKZ | 173.0 | 18.3 | 2.1 | 0.7 | 56.1 | 3.3 | 8.3 | 5.1 | $1,367 |
| UR5501 | BB36RMQKZ/II11 | 172.3 | 18.6 | 0.0 | 3.0 | 57.0 | 2.9 | 7.8 | 6.2 | $1,360 |
| UR5501 | AB17/ML9 | 169.7 | 16.6 | 1.7 | 6.7 | 58.4 | 3.2 | 8.3 | 5.7 | $1,349 |
| UR5501 | BB38RMQKZ/ML9 | 169.9 | 17.9 | 1.8 | 3.5 | 56.8 | 3.2 | 8.1 | 6.1 | $1,344 |
| UR5501 | RBO1RMQKZ/ML9 | 169.2 | 17.8 | 0.0 | 6.2 | 56.7 | 3.2 | 8.5 | 5.9 | $1,340 |
| UR5501 | BC110/ML9 | 167.1 | 17.7 | 0.8 | 4.1 | 56.0 | 2.8 | 8.1 | 5.9 | $1,324 |
| UR5501 | BB93/A1555RMQKZ | 168.0 | 21.1 | 1.1 | 9.2 | 54.0 | 3.3 | 8.4 | 5.8 | $1,313 |
| UR5501 | BC110RHTTZ/ML9 | 164.3 | 17.3 | 1.7 | 4.1 | 57.2 | 2.9 | 8.3 | 5.8 | $1,303 |

TABLE 4

Overall Comparisons: Year 1 field trials, 15 Replications

| Trial | Pedigree | Yld Grain | H2O | SL % | RL % | TW | EHt | PlHt | Asp | Eco $8/¢ 3 |
|---|---|---|---|---|---|---|---|---|---|---|
| UC4609 | DKC57-50 | 177.6 | 20.8 | 0.1 | 0.0 | 55.8 | 3.1 | 8.6 | 6.1 | $1,389 |
| UC4609 | CB20/A1555RMQKZ | 176.3 | 20.4 | 1.1 | 0.0 | 53.8 | 3.4 | 8.5 | 5.8 | $1,382 |
| UC4609 | BB38RMQKZ/MM53 | 173.6 | 18.9 | 0.3 | 0.2 | 55.9 | 3.3 | 9.0 | 5.1 | $1,368 |
| UC4609 | CB18/MN7RMQKZ | 172.5 | 20.5 | 0.5 | 0.2 | 54.0 | 3.1 | 8.6 | 5.4 | $1,352 |
| UC4609 | BB95/A1555RMQKZ | 166.1 | 20.8 | 1.4 | 0.5 | 55.8 | 3.3 | 8.9 | 5.8 | $1,300 |
| UC4609 | RB01RMQKZ/MM53 | 164.2 | 19.5 | 0.6 | 0.0 | 54.4 | 3.1 | 8.8 | 5.4 | $1,291 |
| UC4609 | DKC53-78 | 160.6 | 17.4 | 0.1 | 0.0 | 58.0 | 2.7 | 9.1 | 4.7 | $1,273 |
| UC4609 | BB59/A1555RMQKZ | 158.2 | 22.5 | 0.0 | 0.0 | 53.4 | 3.1 | 8.9 | 6.1 | $1,230 |

MN26 Field Test Trials (Tables 2M to 8M)

TABLE 2M

Overall Comparisons: Second year field trials, 18 locations

| HYBRID | YLD | H2O | Y/M | SL % | RL % | TW | Asp | EHt | PlHt |
|---|---|---|---|---|---|---|---|---|---|
| DKC61-69 | 216.4 | 25.6 | 8.4 | 1.9 | 5.9 | 51.7 | 5.1 | 3.6 | 8.6 |
| BB14BT1CCR1/MN7 | 210.5 | 25.2 | 8.3 | 0.5 | 0.0 | 51.4 | 5.2 | 3.5 | 8.5 |
| BB14BT1CCR1/MN26 | 207.1 | 23.5 | 8.8 | 1.8 | 0.0 | 52.3 | 5.6 | 3.2 | 8.6 |
| RBO1CCR1/MM27BT1 | 202.9 | 27.1 | 7.5 | 1.3 | 0.4 | 50.6 | 5.4 | 3.4 | 8.5 |
| BB14CCR1/MM27BT1 | 202.5 | 24.9 | 8.1 | 0.8 | 0.1 | 51.5 | 5.9 | 3.4 | 8.6 |
| HCL301CCR1/HCL516BT1 | 201.9 | 23.8 | 8.5 | 1.7 | 0.1 | 52.6 | 4.8 | 3.4 | 8.5 |

TABLE 3M

Overall Comparisons: Third year field trials, 8 locations

| HYBRID | YLD | H2O | Y/M | SL % | RL % | TW | Asp | EHt | PlHt |
|---|---|---|---|---|---|---|---|---|---|
| BB14BT1CCR1/MN26 | 199.7 | 22.2 | 9.0 | 5.4 | 0.0 | 56.9 | 7.5 | 3.8 | 9.1 |
| R6258RMQKZ/R2683LMSLZ | 194.6 | 19.3 | 10.1 | 2.2 | 6.2 | 58.0 | 6.0 | 3.8 | 9.8 |
| BB33/MN8 | 189.5 | 18.3 | 10.3 | 2.3 | 0.0 | 58.6 | 7.0 | 3.8 | 9.7 |
| HCL301CCR1/HCL516BT1 | 185.5 | 18.7 | 9.9 | 1.5 | 1.7 | 58.1 | 7.0 | 3.6 | 9.5 |

TABLE 4M

Overall Comparisons: Third year field trials, 28 locations

| HYBRID | YLD | H2O | Y/M | SL % | RL % | TW | Asp | EHt | PlHt |
|---|---|---|---|---|---|---|---|---|---|
| NP2660GTCBLLRW/NP2727 | 189.2 | 19.6 | 9.7 | 1.4 | 1.3 | 55.7 | 6.9 | 3.7 | 8.8 |
| BB14BT1CCR1/MN26 | 186.0 | 21.7 | 8.6 | 2.7 | 0.3 | 55.5 | 6.5 | 3.1 | 8.4 |
| RBO1BT1CCR1/ML9 | 184.4 | 17.3 | 10.6 | 2.9 | 0.5 | 56.3 | 6.4 | 3.2 | 8.3 |
| HCL301CCR1/HCL516BT1 | 182.8 | 18.7 | 9.8 | 3.0 | 2.5 | 55.8 | 5.8 | 3.1 | 8.2 |
| DKC52-59 | 180.9 | 16.6 | 10.9 | 2.6 | 1.1 | 56.3 | 5.8 | 3.3 | 7.8 |
| P35F44 | 181.0 | 20.2 | 9.0 | 0.6 | 0.6 | 56.0 | 6.5 | 3.1 | 7.9 |
| R6258RMQKZ/R2683LMSLZ | 175.6 | 19.0 | 9.2 | 3.3 | 1.5 | 55.8 | 6.1 | 3.5 | 8.6 |
| DKC50-44 | 175.7 | 17.6 | 10.0 | 5.8 | 1.9 | 56.3 | 5.1 | 3.3 | 7.9 |

TABLE 5M

Overall Comparisons: Third year field trials, 26 locations

| HYBRID | YLD | H2O | Y/M | SL % | RL % | TW | Asp | EHt | PlHt |
|---|---|---|---|---|---|---|---|---|---|
| BB36/MN26 | 186.8 | 20.4 | 9.2 | 3.7 | 2.8 | 55.2 | 6.4 | 3.4 | 10.1 |
| BB59/LH287RR2-1 | 188.0 | 19.1 | 9.8 | 1.6 | 0.3 | 55.3 | 6.2 | 3.3 | 9.3 |
| BB14/MM27 | 181.0 | 18.6 | 9.7 | 2.7 | 0.9 | 55.4 | 5.6 | 3.1 | 9.2 |
| DKC61-69 | 183.1 | 19.5 | 9.4 | 3.3 | 2.3 | 55.4 | 5.8 | 3.7 | 9.5 |

TABLE 5M-continued

Overall Comparisons: Third year field trials, 26 locations

| HYBRID | YLD | H2O | Y/M | SL % | RL % | TW | Asp | EHt | PlHt |
|---|---|---|---|---|---|---|---|---|---|
| RBO1RR2/LH287 | 177.7 | 19.3 | 9.2 | 2.1 | 2.5 | 55.5 | 5.5 | 3.1 | 9.1 |
| BB38/ML9 | 177.8 | 18.7 | 9.5 | 1.1 | 0.3 | 55.4 | 6.3 | 3.1 | 9.4 |
| HCL301RR2/HCL516BT1 | 171.5 | 17.8 | 9.6 | 3.7 | 2.7 | 55.9 | 5.7 | 3.3 | 9.5 |

TABLE 6M

Overall Comparisons: Fourth year field trials, 25 locations

| HYBRID | YLD | H2O | Y/M | SL % | RL % | TW | Asp | EHt | PlHt |
|---|---|---|---|---|---|---|---|---|---|
| BB59/LH287BT1CCR1 | 193.9 | 22.6 | 8.6 | 0.6 | 3.5 | 55.3 | 6.1 | 3.6 | 9.1 |
| DKC57-50 | 181.8 | 20.7 | 8.8 | 0.4 | 1.0 | 55.9 | 5.6 | 3.6 | 9.0 |
| BB87/MN26 | 185.3 | 21.6 | 8.6 | 0.3 | 0.8 | 55.8 | 5.7 | 3.7 | 9.4 |
| BB38/MN26 | 179.2 | 21.9 | 8.2 | 0.9 | 0.0 | 56.3 | 5.9 | 3.6 | 9.3 |
| BB38/ML9 | 180.7 | 20.4 | 8.9 | 0.9 | 2.3 | 55.8 | 5.4 | 3.3 | 8.9 |
| BB59/LH287RR2-1 | 179.8 | 21.6 | 8.3 | 1.4 | 2.7 | 55.5 | 5.6 | 3.1 | 8.9 |
| HCL301RR2/HCL516BT1 | 173.7 | 20.2 | 8.6 | 1.5 | 3.1 | 56.7 | 4.8 | 3.3 | 9.0 |

TABLE 7M

Overall Comparisons: Fifth year field trials, 14 locations

| HYBRID | YLD | H2O | Y/M | SL % | RL % | TW | Asp | EHt | PlHt |
|---|---|---|---|---|---|---|---|---|---|
| CB27/MN26 | 187.9 | 20.9 | 9.0 | 0.0 | 0.0 | 54.0 | 6.4 | 3.8 | 9.4 |
| BB38RMQKZ/MM53 | 184.2 | 18.1 | 10.2 | 0.0 | 1.1 | 57.0 | 5.8 | 3.6 | 10.0 |
| CB18/MN7RMQKZ | 182.8 | 19.1 | 9.6 | 0.0 | 0.0 | 55.3 | 5.5 | 3.4 | 9.2 |
| BB59/A1555RMQKZ | 180.1 | 21.5 | 8.4 | 0.0 | 0.0 | 53.9 | 6.5 | 3.1 | 9.3 |
| DKC57-50 | 178.5 | 19.6 | 9.1 | 0.1 | 0.0 | 56.6 | 5.7 | 3.4 | 9.2 |
| P1018AM1 | 172.5 | 20.7 | 8.3 | 0.0 | 4.1 | 55.4 | 6.1 | 4.1 | 10.0 |

TABLE 8M

Overall Comparisons: Fifth year field trials, 22 locations

| HYBRID | YLD | H2O | Y/M | SL % | RL % | TW | Asp | EHt | PlHt |
|---|---|---|---|---|---|---|---|---|---|
| DKC62-97 | 185.6 | 18.3 | 10.2 | 0.1 | 0.0 | 56.0 | 6.0 | 3.7 | 9.3 |
| BB38/A1555RMQKZ | 184.6 | 19.7 | 9.4 | 1.2 | 0.3 | 54.3 | 6.3 | 3.5 | 9.2 |
| BB87/A1555RMQKZ | 183.7 | 20.1 | 9.2 | 0.4 | 0.9 | 54.3 | 6.4 | 3.4 | 9.2 |
| BB36/A1555RMQKZ | 183.2 | 20.0 | 9.2 | 1.0 | 2.0 | 53.4 | 6.0 | 2.9 | 9.4 |
| BB36RMQKZ/MN26 | 181.4 | 19.1 | 9.5 | 0.5 | 0.4 | 54.7 | 6.3 | 3.5 | 9.6 |
| CB15/A1555RMQKZ | 181.2 | 20.9 | 8.7 | 0.8 | 1.2 | 53.9 | 6.0 | 3.2 | 8.9 |
| P1395AM1 | 180.3 | 20.7 | 8.7 | 2.6 | 2.5 | 54.7 | 6.2 | 3.3 | 9.9 |
| BB59/A1555RMQKZ | 179.0 | 19.5 | 9.2 | 0.1 | 0.9 | 54.1 | 6.3 | 3.3 | 9.3 |
| CB18/MN7RMQKZ | 177.0 | 17.0 | 10.4 | 0.9 | 0.1 | 56.2 | 5.2 | 3.3 | 9.0 |

The foregoing detailed description has been given for clearness of understanding only and no unnecessary limitations should be understood there from as modifications will be obvious to those skilled in the art.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A seed of inbred corn line designated BC106, wherein a representative sample of seed of said line was deposited under ATCC Accession No. PTA-124009.

2. A corn plant, or a part thereof, produced by growing the seed of claim 1.

3. A corn plant, or a part thereof, having all the physiological and morphological characteristics of inbred line BC106, wherein a representative sample of seed of said line was deposited under ATCC Accession No. PTA-124009.

4. A tissue culture of cells produced from the plant of claim 2.

5. A corn plant regenerated from the tissue culture of claim 4, wherein the regenerated plant has all the morphological and physiological characteristics of inbred line BC106, wherein a representative sample of seed of said line was deposited under ATCC Accession No. PTA-124009.

6. A method for producing a hybrid corn seed wherein the method comprises crossing the plant of claim 2 with a different corn plant and harvesting the resultant hybrid corn seed.

7. A hybrid corn seed produced by the method of claim 6.

8. An F1 hybrid corn plant, or part thereof, produced by growing the seed of claim 7, wherein said part comprises at least one plant cell of the hybrid corn plant.

9. A method for producing inbred corn line BC106, wherein a representative sample of seed of said line was deposited under ATCC Accession No. PTA-124009, wherein the method comprises:
   a) planting a collection of seeds comprising seed of a hybrid, one of whose parents is inbred line BC106, said collection also comprising seed of said inbred;
   b) growing plants from said collection of seeds;
   c) identifying the plants having the physiological and morphological characteristics of inbred corn line BC106, as inbred parent plants;
   d) controlling pollination of said inbred parent plants in a manner which preserves the homozygosity of said inbred parent plant; and
   e) harvesting the resultant seed and thereby producing an inbred corn line having all of the physiological and morphological characteristics of inbred corn line BC106.

10. The method of claim 9 wherein step (c) comprises identifying plants with decreased vigor compared to the other plants grown from the collection of seeds.

11. A method for producing a corn plant that contains in its genetic material one or more transgenes, wherein the method comprises crossing the corn plant of claim 2 with either a second plant of another corn line which contains a transgene or a transformed corn plant of the inbred corn line BC106, so that the genetic material of the progeny plant that results from the cross contains the transgene(s) operably linked to a regulatory element and wherein the transgene is selected from the group consisting of male sterility, male fertility, herbicide resistance, insect resistance, disease resistance, water stress tolerance, and increased digestibility.

12. A corn plant, or a part thereof, produced by the method of claim 11, wherein the corn plant containing the transgenes and otherwise all of the physiological and morphological characteristics of inbred corn line BC106, wherein a representative sample of seed of said line was deposited under ATCC Accession No. PTA-124009, and wherein said part comprises at least one plant cell of the corn plant.

13. The corn plant of claim 12, wherein the transgene confers resistance to an herbicide selected from the group consisting of imidazolinone, sulfonylurea, glyphosate, glufosinate, L-phosphinothricin, triazine and benzonitrile.

14. The corn plant of claim 12, wherein the transgene encodes a *Bacillus thuringiensis* protein.

15. The corn plant of claim 12, wherein the transgene confers disease resistance.

16. The corn plant of claim 12, wherein the transgene confers water stress tolerance.

17. The corn plant of claim 12, wherein the transgene confers increased digestibility.

18. A method for producing a hybrid corn seed wherein the method comprises crossing the plant of claim 12 with a different corn plant and harvesting the resultant hybrid corn seed.

19. A method of producing a corn plant with increased waxy starch or increased amylose starch wherein the method comprises transforming the corn plant of claim 2 with a transgene that modifies waxy starch or amylose starch metabolism, thereby producing a corn plant with increased waxy starch or amylose starch metabolism.

20. A corn plant produced by the method of claim 19.

21. A method of introducing one or more desired traits into inbred corn line BC106, wherein the method comprises:
   a) crossing the inbred line BC106 plants grown from the inbred line BC106 seed, wherein a representative sample of seed of said line was deposited under ATCC Accession No. PTA-124009, with plants of another corn line that comprise one or more desired traits to produce progeny plants, wherein the one or more desired traits are selected from the group consisting of male sterility, male fertility, herbicide resistance, insect resistance, disease resistance, waxy starch, water stress tolerance, increased amylose starch and increased digestibility;
   b) selecting progeny plants that have the one or more desired traits to produce selected progeny plants;
   c) crossing the selected progeny plants with the inbred corn line BC106 plants to produce backcross progeny plants;
   d) selecting for backcross progeny plants that have the one or more desired traits and physiological and morphological characteristics of inbred corn line BC106, wherein a representative sample of seed of said line was deposited under ATCC Accession No. PTA-124009, to produce selected backcross progeny plants; and
   e) repeating steps (c) and (d) one or more times in succession to produce selected second or higher backcross progeny plants that comprise the desired one or more traits and all of the physiological and morphological characteristics of inbred corn line BC106 as listed in Table 1J.

22. A corn plant produced by the method of claim 21, wherein the plant has the one or more desired traits and all of the physiological and morphological characteristics of inbred corn line BC106, wherein a representative sample of seed of said line was deposited under ATCC Accession No. PTA-124009.

23. A method for producing inbred corn line BC106 seed, wherein a representative sample of seed of said line was deposited under ATCC Accession No. PTA-124009, wherein the method comprises crossing a first inbred parent corn plant with a second inbred parent corn plant and harvesting the resultant corn seed, wherein both said first and second inbred corn plant are the corn plant of claim 2.

24. A method for producing inbred corn line BC106, wherein a representative sample of seed of said line was deposited under ATCC Accession No. PTA-124009, wherein the method comprises:
  a) planting the inbred corn seed of claim 1;
  b) growing a plant from said seed;
  c) controlling pollination in a manner that the pollen produced by the grown plant pollinates the ovules produced by the grown plant; and
  d) harvesting the resultant seed and thereby producing an inbred corn line having all of the physiological and morphological characteristics of inbred corn line BC106.

25. A method for producing a hybrid corn seed wherein the method comprises crossing the plant of claim 22 with a different corn plant and harvesting the resultant hybrid corn seed.

26. A hybrid corn seed produced by the method of claim 25.

27. A method of producing a corn product, said method comprising milling the inbred seed of claim 1, thereby producing the corn product.

28. The method of claim 27, wherein the corn product is selected from the group consisting of corn meal, corn flour, corn starch, corn syrup, corn sweetener and corn oil.

29. A method of producing a corn product, said method comprising milling the hybrid seed of claim 7, thereby producing the corn product.

30. The method of claim 29, wherein the corn product is selected from the group consisting of corn meal, corn flour, corn starch, corn syrup, corn sweetener and corn oil.

* * * * *